US012562248B2

(12) United States Patent
Lafauci et al.

(10) Patent No.: US 12,562,248 B2
(45) Date of Patent: Feb. 24, 2026

(54) SYSTEMS AND METHODS FOR TRACKING ITEMS

(71) Applicant: Midas Healthcare Solutions, Inc., Center Moriches, NY (US)

(72) Inventors: Michael A. Lafauci, Center Moriches, NY (US); Jeffrey R. Wahl, Beachwood, OH (US); Jonathan Pinsky, Bedford, NY (US)

(73) Assignee: MIDAS Healthcare Solutions, Inc., Center Moriches, NY (US)

( * ) Notice: Subject to any disclaimer, the term of this patent is extended or adjusted under 35 U.S.C. 154(b) by 243 days.

(21) Appl. No.: 18/230,482

(22) Filed: Aug. 4, 2023

(65) Prior Publication Data

US 2024/0212815 A1 Jun. 27, 2024

Related U.S. Application Data

(63) Continuation of application No. PCT/US2022/015595, filed on Feb. 8, 2022.
(Continued)

(51) Int. Cl.
*G16H 20/10* (2018.01)
(52) U.S. Cl.
CPC .................................. *G16H 20/10* (2018.01)
(58) Field of Classification Search
CPC ........ G16H 20/10; G16H 20/13; G16H 40/20; G16H 40/67
See application file for complete search history.

(56) References Cited

U.S. PATENT DOCUMENTS 5,813,009 A * 9/1998 Johnson .................. G06F 16/40
707/916
9,283,321 B2 3/2016 Nelson et al.
(Continued)

FOREIGN PATENT DOCUMENTS

CN 118405390 A 7/2024
EP 1941411 B1 9/2011
(Continued)

OTHER PUBLICATIONS

U.S. Appl. No. 17/492,058 Office Action dated Nov. 1, 2023.
(Continued)

*Primary Examiner* — Joshua B Blanchette
(74) *Attorney, Agent, or Firm* — Wilson Sonsini Goodrich & Rosati

(57) ABSTRACT

The present disclosure provides a module for monitoring handling of various item(s). In some embodiments, the item(s) can include medications, e.g., leftover or unused medications. In an aspect, the present disclosure provides a method for monitoring medication wasting. The method can comprise generating a digital communication between a medication monitoring module and at least one sensor of a user device. The method can comprise directing, by the medication monitoring module, the at least one sensor to: (i) record disposal of a medication to a medication waste unit by a user, wherein the medication waste unit is not a part of the user device; and (ii) record the user prior to, during, or subsequent to the disposal of the medication by the user. The method can further comprise generating a plurality of digital data representative of the disposal and the user.

23 Claims, 30 Drawing Sheets

Related U.S. Application Data

(60) Provisional application No. 63/290,959, filed on Dec. 17, 2021, provisional application No. 63/187,577, filed on May 12, 2021, provisional application No. 63/146,935, filed on Feb. 8, 2021.

(56) References Cited

U.S. PATENT DOCUMENTS

| | | | |
|---|---|---|---|
| 9,662,062 | B2 | 5/2017 | De Guia et al. |
| 2006/0200365 | A1 | 9/2006 | Mallett et al. |
| 2008/0195247 | A1 | 8/2008 | Mallett et al. |
| 2008/0198021 | A1 | 8/2008 | Flood |
| 2009/0014461 | A1 | 1/2009 | Omura et al. |
| 2012/0059911 | A1 | 3/2012 | Randhawa et al. |
| 2012/0065999 | A1 | 3/2012 | Takatoku et al. |
| 2012/0210252 | A1* | 8/2012 | Fedoseyeva ..... G06Q 10/06398 715/753 |
| 2012/0226447 | A1 | 9/2012 | Nelson et al. |
| 2013/0046555 | A1 | 2/2013 | Hyde et al. |
| 2013/0282392 | A1 | 10/2013 | Wurm |
| 2013/0325727 | A1 | 12/2013 | MacDonell et al. |
| 2014/0190845 | A1 | 7/2014 | Maness |
| 2014/0318078 | A1 | 10/2014 | Kondo et al. |
| 2015/0144012 | A1 | 5/2015 | Frybarger |
| 2017/0255760 | A1 | 9/2017 | Lee et al. |
| 2018/0300994 | A1 | 10/2018 | Nelson et al. |
| 2019/0244699 | A1 | 8/2019 | Loebig et al. |
| 2020/0365244 | A1 | 11/2020 | Shah et al. |
| 2021/0027259 | A1* | 1/2021 | Burgess .............. G06Q 50/265 |
| 2022/0254470 | A1 | 8/2022 | Lafauci et al. |

FOREIGN PATENT DOCUMENTS

| | | | |
|---|---|---|---|
| EP | 2866163 | A2 | 4/2015 |
| EP | 2866163 | B1 | 9/2018 |
| JP | 2012138086 | A | 7/2012 |
| WO | WO1998050840 | A2 * | 11/1998 |
| WO | WO-2015131038 | A2 | 12/2015 |
| WO | WO-2017066652 | A1 | 4/2017 |
| WO | WO-2018051186 | A2 | 4/2018 |
| WO | WO-2020018577 | A1 | 1/2020 |
| WO | WO-2020172471 | A1 | 8/2020 |
| WO | WO-2020206154 | A1 | 10/2020 |
| WO | WO-2022170236 | A1 | 8/2022 |

OTHER PUBLICATIONS

EP20783942.4 Extended Search Report dated Nov. 11, 2022.

PCT/US2020/026434 International Search Report with Written Opinion dated Jul. 21, 2020.

PCT/US2022/015595 International Search Report and Written Opinion dated Jun. 21, 2022.

EP20220750569.0 Extended European Search Report dated Oct. 25, 2024.

PCT/US2024/051588 International Search Report and Written Opinion dated Dec. 17, 2024.

U.S. Appl. No. 17/492,058 Office Action dated Jan. 10, 2025.

U.S. Appl. No. 17/492,058 Office Action dated May 22, 2024.

U.S. Appl. No. 17/492,058 Office Action dated Sep. 5, 2024.

* cited by examiner

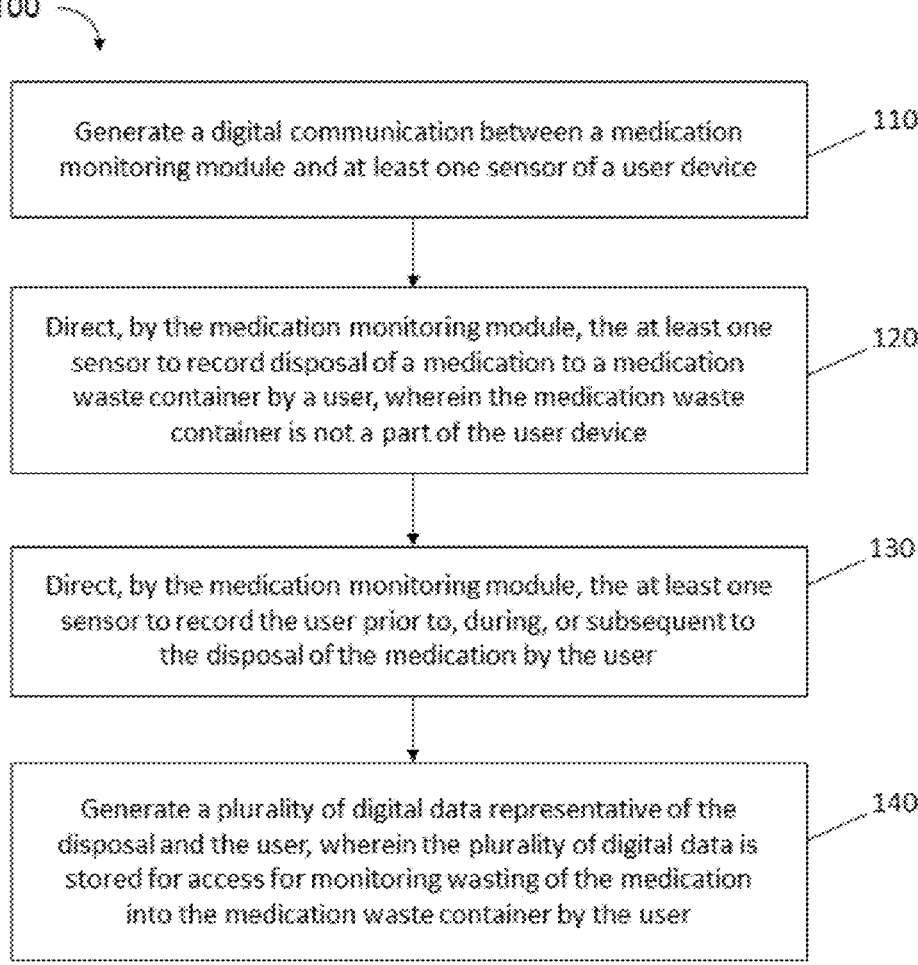

100

Generate a digital communication between a medication
monitoring module and at least one sensor of a user device                     110

Direct, by the medication monitoring module, the at least one
sensor to record disposal of a medication to a medication
waste container by a user, wherein the medication waste
container is not a part of the user device                                     120

Direct, by the medication monitoring module, the at least one
sensor to record the user prior to, during, or subsequent to
the disposal of the medication by the user                                     130

Generate a plurality of digital data representative of the
disposal and the user, wherein the plurality of digital data is
stored for access for monitoring wasting of the medication
into the medication waste container by the user                                140

*FIG. 1*

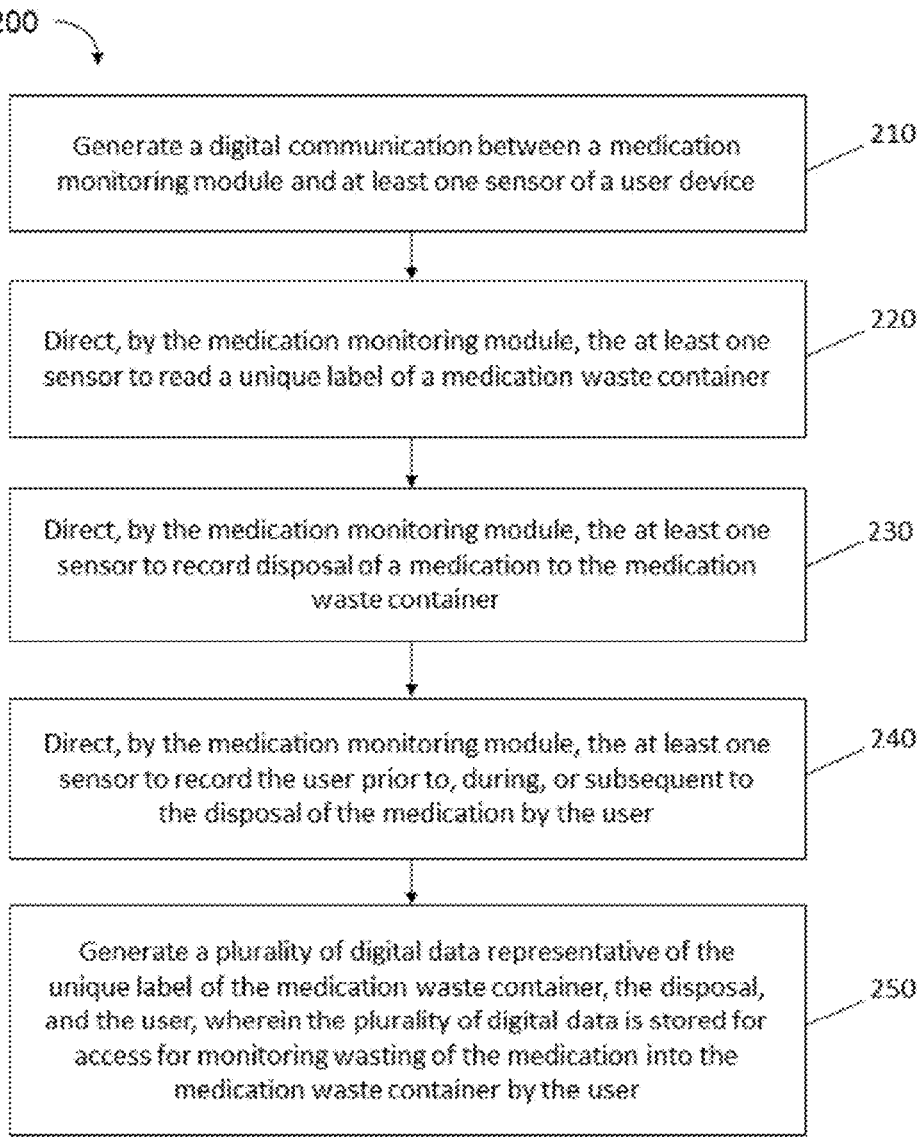

200

Generate a digital communication between a medication monitoring module and at least one sensor of a user device — 210

Direct, by the medication monitoring module, the at least one sensor to read a unique label of a medication waste container — 220

Direct, by the medication monitoring module, the at least one sensor to record disposal of a medication to the medication waste container — 230

Direct, by the medication monitoring module, the at least one sensor to record the user prior to, during, or subsequent to the disposal of the medication by the user — 240

Generate a plurality of digital data representative of the unique label of the medication waste container, the disposal, and the user, wherein the plurality of digital data is stored for access for monitoring wasting of the medication into the medication waste container by the user — 250

*FIG. 2*

Device and App can:
• scan Rx barcode
• show medication
• show consumer's face
• AI can count pills
• AI can recognize pills
• RVC matches code

Tamper-evident return bag
(examples only)

Or meds can be destroyed in bag on camera

Bed mount for witnessing administration of meds

Device and App can:
• scan barcode
• show patient band
• show medication
• show caregiver face
• match RVC code

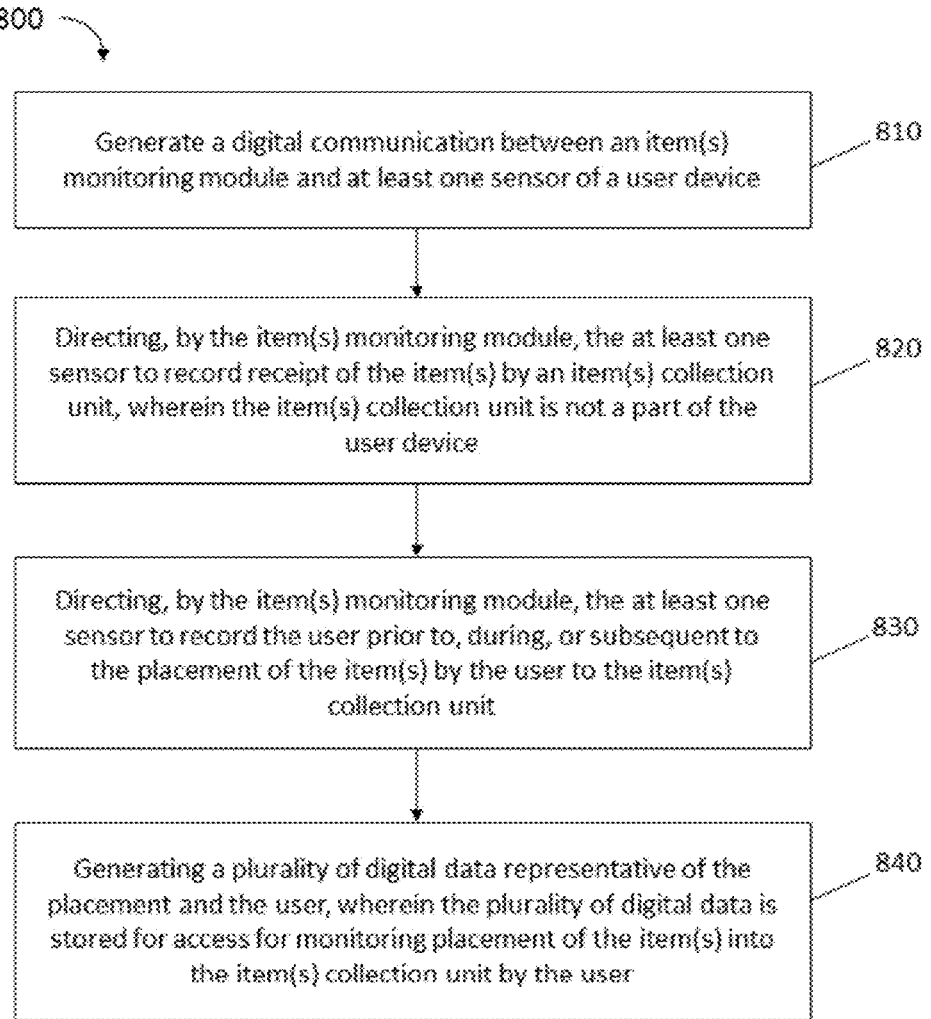

800

Generate a digital communication between an item(s) monitoring module and at least one sensor of a user device — 810

Directing, by the item(s) monitoring module, the at least one sensor to record receipt of the item(s) by an item(s) collection unit, wherein the item(s) collection unit is not a part of the user device — 820

Directing, by the item(s) monitoring module, the at least one sensor to record the user prior to, during, or subsequent to the placement of the item(s) by the user to the item(s) collection unit — 830

Generating a plurality of digital data representative of the placement and the user, wherein the plurality of digital data is stored for access for monitoring placement of the item(s) into the item(s) collection unit by the user — 840

*FIG. 8*

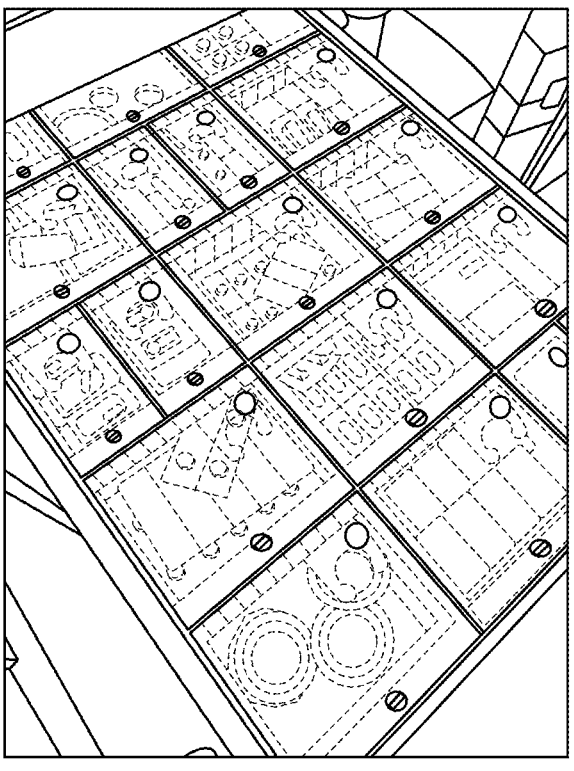
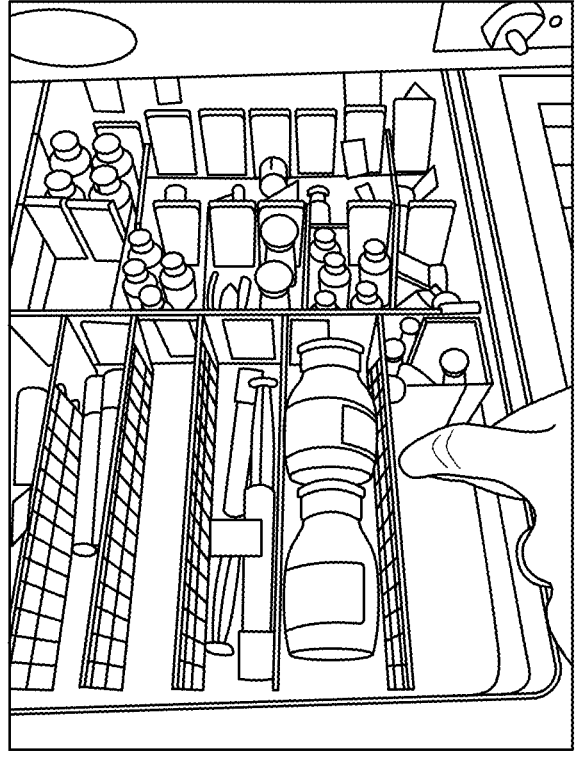
FIG. 12

Waste medication
confirmation camera(s)
(e.g., 4k, high-speed)

Camera(s) with
facial recognition

Medication
disposal
container

Moving unit
(e.g., wheel(s))

Collection (e.g.,
random collection)
for central
pharmacy assay

Additional device(s)
for virtual witness or
data review/analysis

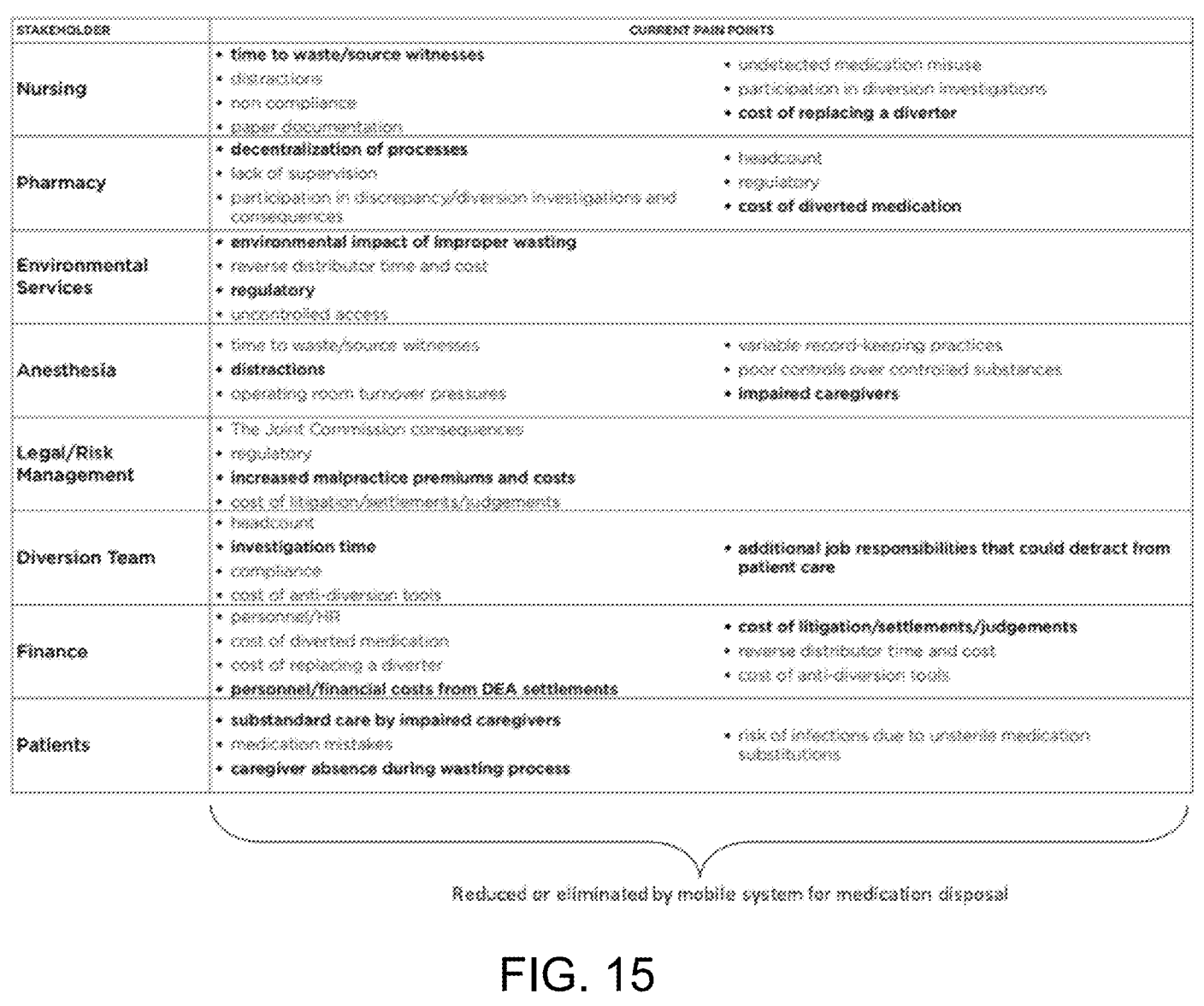

| STAKEHOLDER | | CURRENT PAIN POINTS |
| --- | --- | --- |
| Nursing | • time to waste/source witnesses <br> • distractions <br> • non-compliance <br> • theft/compromise <br> • decentralization of processes <br> • lack of automation <br> • participation in diversion/diversion investigation and complaints | • unsolicited medication misuse <br> • participation in diversion investigations <br> • cost of replacing a diverter |
| Pharmacy | • environmental impact of improper wasting <br> • reverse distributor time and cost <br> • regulatory <br> • unprotected actors | • headcount <br> • regulatory <br> • cost of diverted medication |
| Environmental Services | • time to waste/source witnesses <br> • distractions <br> • ongoing recurring turnover processes | |
| Anesthesia | • The Joint Commission consequences <br> • regulatory <br> • increased malpractice premiums and costs <br> • cost of litigation/settlements/judgements <br> • headcount | • console record-keeping practices <br> • poor controls over controlled substances <br> • impaired caregivers |
| Legal/Risk Management | • investigation time <br> • compliance <br> • cost of anti-diversion tools <br> • personnel/fill | • additional job responsibilities that could detract from patient care |
| Diversion Team | • cost of diverted medication <br> • cost of replacing a diverter <br> • personnel/financial costs from DEA settlements | • cost of litigation/settlements/judgements <br> • reverse distributor time and cost <br> • cost of anti-diversion tools |
| Finance | • substandard care by impaired caregivers <br> • medication toxicities <br> • caregiver absence during wasting process | • risk of infections due to unsterile medication substitutions |
| Patients | | |

Reduced or eliminated by mobile system for medication disposal

FIG. 15

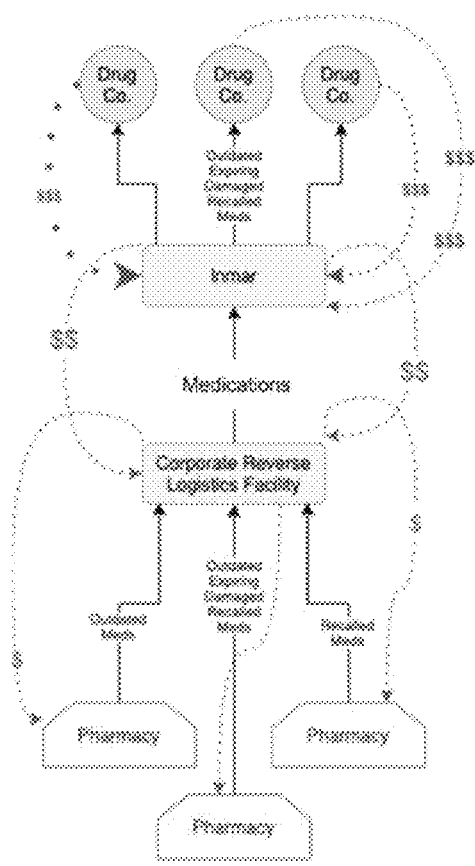
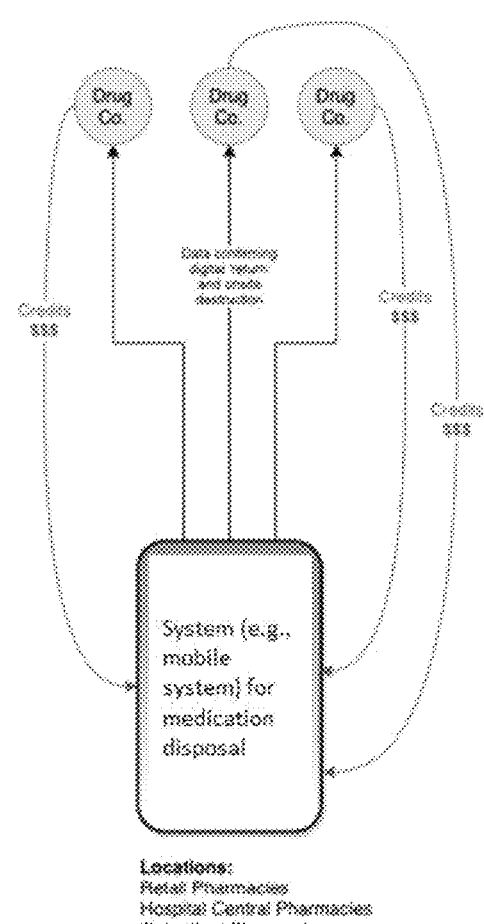
*FIG. 17*

Username
Password
*FIG. 21A*
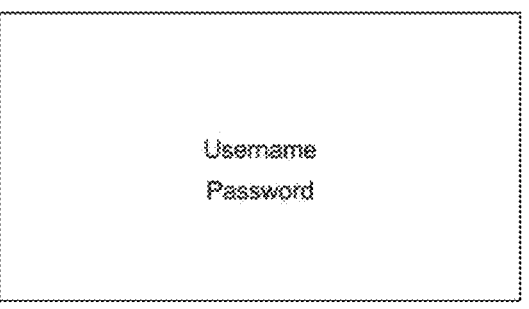
*FIG. 21B*
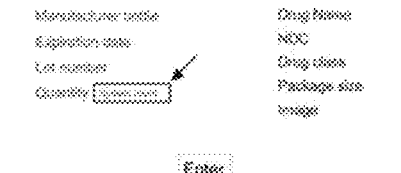
Scan product 2D barcode of contracted solid
*FIG. 21C*
Outcome if Hazardous
Slot 1    Slot 2    Slot 3
*FIG. 21D*
Outcome if Non-hazardous
Place product into
Slot 1    Slot 2    Slot 3
*FIG. 21E*
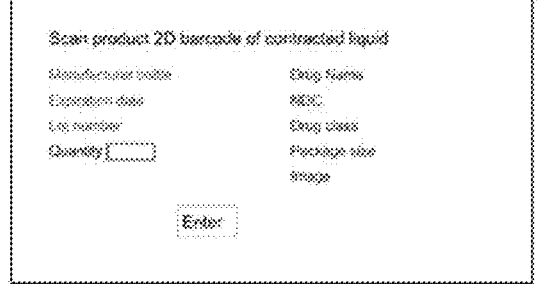
Scan product 2D barcode of contracted liquid
Enter
*FIG. 21F*
Outcome for Hazardous
Place product into
Slot 1    Slot 2    Slot 3
*FIG. 21G*
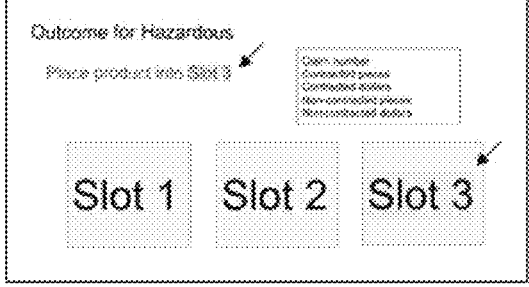
Outcome if Non-hazardous
Place product into
Slot 1    Slot 2    Slot 3
*FIG. 21H*
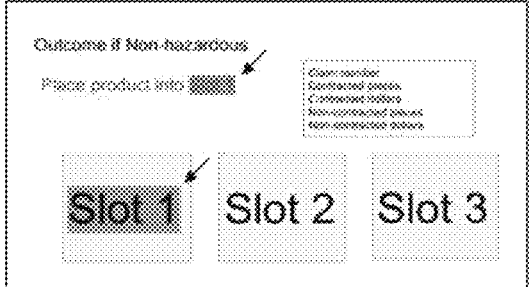
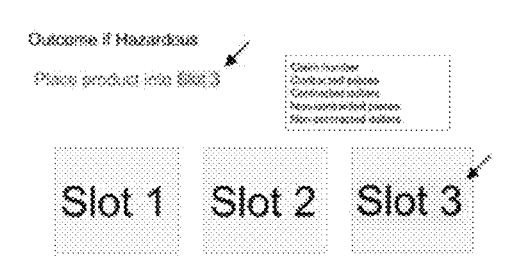

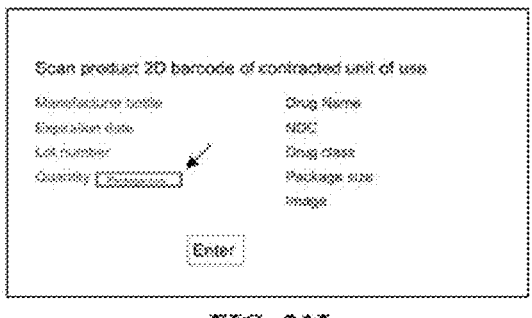
*FIG. 21I*
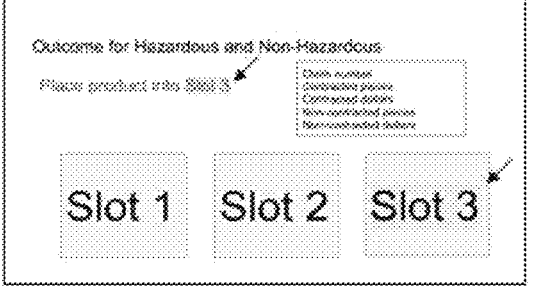
*FIG. 21J*
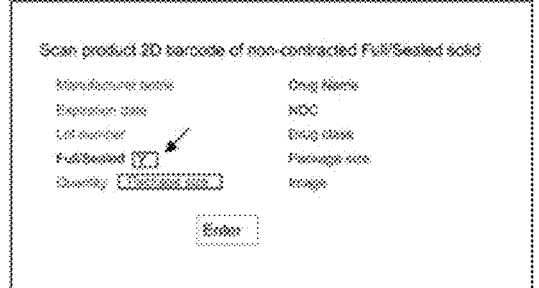
*FIG. 21K*
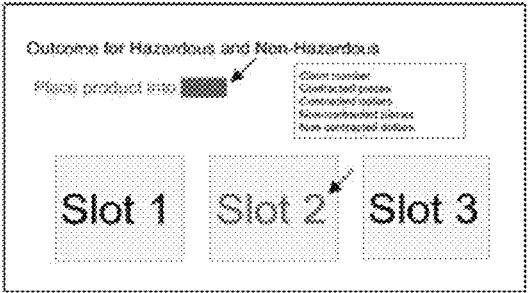
*FIG. 21L*
*FIG. 21M*
*FIG. 21N*
*FIG. 21O*
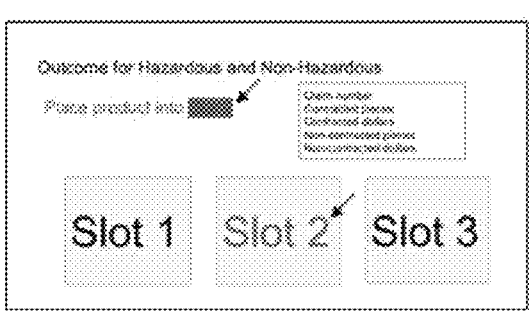
*FIG. 21P*

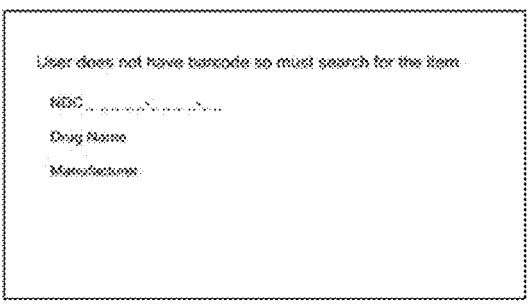
*FIG. 21Y*
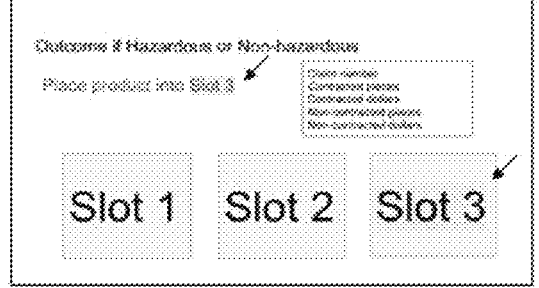
*FIG. 21CC*
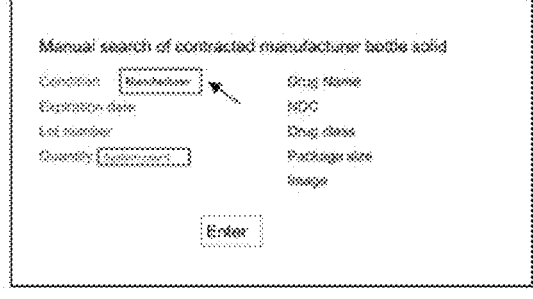
*FIG. 21Z*
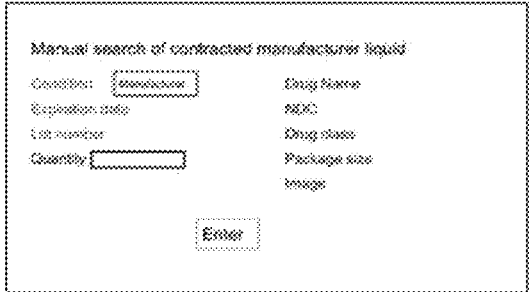
*FIG. 21DD*
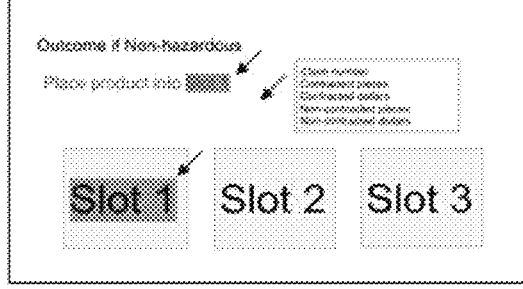
*FIG. 21AA*
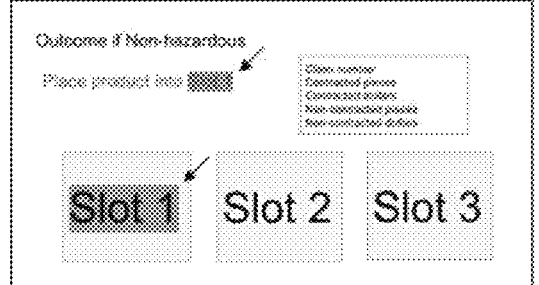
*FIG. 21EE*
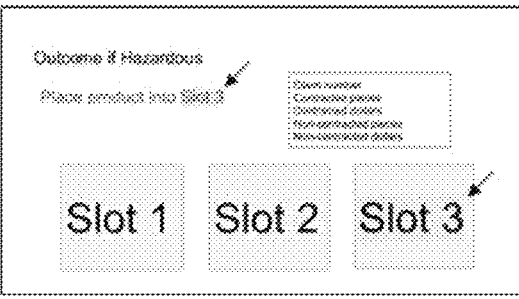
*FIG. 21BB*
*FIG. 21FF*

| Claim Number | Claim Date | User | Contracted pieces | Contracted dollars | Non-contracted pieces | Non-contracted dollars |
|---|---|---|---|---|---|---|
| | | | | | | |
| | | | | | | |
| | | | | | | |

*FIG. 21UU*

Claim number, Claim date, User

| | | | | | | | | | | | | | |
|---|---|---|---|---|---|---|---|---|---|---|---|---|---|
| | | | | | | | | | | | | | |
| | | | | | | | | | | | | | |
| | | | | | | | | | | | | | |
| | | | | | | | | | | | | | |
| | | | | | | | | | | | | | |
| | | | | | | | | | | | | | |

*FIG. 21VV*

No credit reason codes

| 1 | Manufacturer does not take returns |
| 2 | Manufacturer does not take NDC |
| 3 | Manufacturer does not accept partials |
| 4 | Partial minimum not met |
| 5 | Amber vial/Amber bottles not accepted |
| 6 | Manufacturer seal required |
| 7 | Vendor off invoice allowance |
| 8 | Lot number not eligible for credit |
| 9 | Consignment item |
| 10 | Past expiration policy/returned too late |

*FIG. 21WW*

Company name
Store number
Address
Telephone
DEA Number

Process New Claim    Processed Claims    Credit Status

*FIG. 21XX*

SYSTEMS AND METHODS FOR TRACKING ITEMS

CROSS-REFERENCE

This application is a continuation of International Patent Application No. PCT/US22/15595, filed Feb. 8, 2022, which claims the benefit of U.S. Provisional Patent Application No. 63/146,935, filed Feb. 8, 2021, U.S. Provisional Patent Application No. 63/187,577, filed May 12, 2021, and U.S. Provisional Patent Application No. 63/290,959, filed Dec. 17, 2021, each of which is entirely incorporated herein by reference.

BACKGROUND

Subjects (e.g., patients, healthcare providers, etc.) can have unused or leftover medications (e.g., prescribed medications or over-the-counter medications). For example, a patient can be prescribed more than an adequate or clinically necessary amount of the medications (i.e., overprescription). In another example, a healthcare provider (e.g., a nurse) can have leftover medications (e.g., in a syringe) subsequent to distribution or administration of medications to a patient in need thereof. Yet in a different example, a healthcare provider (e.g., a pharmacist) can have leftover medications (e.g., in a medication distribution packaging or container) subsequent to distribution of medications into prescribed portions. In some cases, a patient may refuse medication.

The subjects can be instructed to discard (e.g., flush in the toilet, discard as trash, etc.) any unused medications or return the unused medications to a drug take-back location (e.g., into a drug collection unit at a pharmacy). In some cases, the patients can return the unused medications on a Drug Enforcement Administration (DEA) Prescription Drug Take Back Day. However, improper discarding or return of the unused medications can expose the medications to third-party access (e.g., medication diversion, addiction, etc.), misuses and related outcomes (e.g., addictions), adverse effects on the environment (e.g., unconsumed medications in the water supply), and/or accidental exposures (e.g., to children). In some cases, two major sources of misused prescription medications (e.g., pain relievers) can include (i) prescription from healthcare providers, and (ii) a friend or family member.

In other cases, medications can be lost or misplaced (intentionally or unintentionally) during transfer thereof (e.g., shipping from a manufacturing factory to a pharmacy) and/or during medication inventory (e.g., stocking medications in a storage room or into an automated dispensing machine (ADM)). For example, medications can be misplaced. In another example, incorrect amount (e.g., number) of medications can be stocked.

In yet other different cases, medications can be lost or misplaced (intentionally or unintentionally) during dispensing of the medications, e.g., from an ADM based on a patient's medication. For example, a healthcare provider can accidentally retrieve medication A, when a patient's prescription recited medication B. Alternatively or in addition to, medications in the ADM can expire or expire shortly (e.g., in a few days or weeks) without the healthcare provider knowing, and this could result in, for example, accidental prescription of medications that have already expired or that will expire during use of the medications by the patient.

SUMMARY

Recognized herein is a need for methods and systems for monitoring medications, e.g., wasting of medications (e.g., controlled or non-controlled) that, in some examples, encourages and promotes medication users (e.g., patients) or healthcare providers (e.g., nurses, advance practice nurses, nurse anesthetists, physicians, physicians assistants, etc.) to manage medications properly during disposal of any unused or leftover medications after use. In some cases, the returned unused/leftover medications can be collected (e.g., at a centralized collection site) for destruction. In some cases, the returned unused/leftover medications may be a single dose wasting process or bulk dose wasting process. In some cases, unsellable medications (e.g., due to recall) can be collected for destruction.

In some embodiments, the systems and methods disclosed herein can monitor a user's disposal of unused or leftover medications to any container (e.g., a medication wasting container) by using a user device (e.g., a mobile phone, a tablet, or smart glasses). In some cases, the user device can comprise a medication monitoring module (e.g., a mobile application) usable for monitoring the medication disposal by the user. In some cases, digital data collected by the medication monitoring module can be stored and accessed to track medication wasting by the user and/or award the user for the disposal of the medication.

In some embodiments, the systems and methods for medical management herein can be implemented, for example, in homes, medication rooms (i.e., med rooms), patient rooms, emergency rooms, and/or surgery rooms.

In some aspects, the present disclosure provides a method for monitoring medication wasting, comprising: (a) generating a digital communication between a medication monitoring module and at least one sensor of a user device; (b) directing, by the medication monitoring module, the at least one sensor to: (i) record disposal of a medication to a medication waste unit by a user, wherein the medication waste unit is not a part of the user device; and (ii) record the user prior to, during, or subsequent to the disposal of the medication by the user; and (c) generating a plurality of digital data representative of the disposal and the user, wherein the plurality of digital data is stored for access for monitoring wasting of the medication into the medication waste unit by the user.

In some aspects, the present disclosure provides a method for monitoring medication wasting, comprising: (a) generating a digital communication between a medication monitoring module and at least one sensor of a user device; (b) directing, by the medication monitoring module, the at least one sensor to: (i) read an identifier of a medication waste unit; (ii) record disposal of a medication to the medication waste unit; and (iii) record the user prior to, during, or subsequent to the disposal of the medication by the user; and (c) generating a plurality of digital data representative of the identifier of the medication waste unit, the disposal, and the user, wherein the plurality of digital data is stored for access for monitoring wasting of the medication into the medication waste unit by the user.

In some embodiments of any one of the methods or systems disclosed herein, the identifier is a machine readable code. In some embodiments, the machine readable code comprises a reconstructable visual code.

In some embodiments of any one of the methods or systems disclosed herein, the method further comprises providing the identifier for labeling the medication waste unit.

In some embodiments of any one of the methods or systems disclosed herein, the user device is releasably coupled to the medication waste unit.

In some embodiments of any one of the methods or systems disclosed herein, the method further comprises using at least a portion of the plurality of digital data to identify the medication or the user. In some embodiments, identification data for the identification of the medication or the user is stored for access by the medication monitoring module.

In some embodiments of any one of the methods or systems disclosed herein, the medication monitoring module is a graphical user interface.

In some embodiments of any one of the methods or systems disclosed herein, the medication monitoring module is a mobile application.

In some embodiments of any one of the methods or systems disclosed herein, the user device comprises a personal computer, mobile device, or a smart wearable device.

In some embodiments of any one of the methods or systems disclosed herein, the user device comprises a robot. In some embodiments, the robot may be fully or at least partially autonomous.

In some embodiments of any one of the methods or systems disclosed herein, the at least one sensor comprises multiple sensors. In some embodiments, the at least one sensor comprises a sensor operable in low-light settings. In some embodiments, the at least one sensor comprises an IR sensor. In some embodiments, the at least one sensor comprises an IR camera.

In some embodiments of any one of the methods or systems disclosed herein, the at least one sensor is at least one camera. In some embodiments, the at least one camera comprises two cameras on different sides of the user device. In some embodiments, the at least one camera is movable with respect to a housing of the user device. In some embodiments, the at least one camera is operatively coupled to an optics assembly of the user device, wherein the optics assembly is configured to (i) move with respect to a housing of the user device or (ii) receive two or more lights from two or more directions and direct the two or more lights to the at least one camera.

In some embodiments of any one of the methods or systems disclosed herein, the medication waste unit is a container. In some embodiments, the container may comprise a sealable opening that, if tampered, is configured to leave a tamper mark.

In some aspects, the present disclosure provides a system for monitoring medication wasting, comprising: a medication monitoring module configured to perform the method of any one of the preceding claims; and one or more of: (i) a coupling unit configured generate a coupling between (1) a user device comprising at least one sensor and (2) a medication waste unit, wherein the medication monitoring module is configured to digitally communicate with the at least one sensor of the user device; (ii) an identifier configured to couple to the medication waste unit; or (iii) a database in digital communication with the medication monitoring module, wherein the database is configured to store digital data generated by the medication monitoring module.

In some embodiments of any one of the methods or systems disclosed herein, the system comprises the coupling unit. In some embodiments of any one of the methods or systems disclosed herein, the coupling is a releasable coupling.

In some embodiments of any one of the methods or systems disclosed herein, the system comprises the identifier.

In some embodiments of any one of the methods or systems disclosed herein, the system comprises the database.

In some embodiments of any one of the methods or systems disclosed herein, the system comprises two or more of (i) through (iii).

In some embodiments of any one of the methods or systems disclosed herein, the system comprises (i), (ii), and (iii).

Also recognized herein is a need for methods and systems for monitoring transfer of medications and/or medication inventory (e.g., stocking medications in a storage room or into an ADM). The systems and methods disclosed herein can monitor a user's performance during such transfer or inventory to, e.g., discourage, prevent, or reduce a chance of losing, misplacing the medications. The systems and methods disclosed herein can monitor the medication that is being transferred and stored to, e.g., confirm identity of the medication, assess expiration date of the medication, or assess a location of placement of the medication.

Also recognized herein is a need for methods and systems for monitoring dispensing of medications, e.g., from an ADM based on a patient's medication. The systems and methods disclosed herein can monitor a user's performance during such dispensing to, e.g., discourage, prevent, or reduce a change of losing, misplacing, or mis-prescribing the medications. The systems and methods disclosed herein can monitor the medication that is being dispensed to, e.g., confirm a match between identity of the medication and what has been prescribed (e.g., to a patient), assess expiration date of the medication, or assess a location of the medication prior to the dispensing (e.g., location of the medication within the ADM).

In some aspects, the present disclosure provides a method for monitoring medication inventory, comprising: (a) generating a digital communication between a medication monitoring module and at least one sensor of a user device; (b) directing, by the medication monitoring module, the at least one sensor to: (i) record inventory of a medication to a medication storage unit, wherein the medication storage unit is not a part of the user device; and (ii) record the user prior to, during, or subsequent to the inventory of the medication by the user; and (c) generating a plurality of digital data representative of the inventory and the user, wherein the plurality of digital data is stored for access for monitoring medication inventory into the medication storage unit by the user.

In some aspects, the present disclosure provides a method for monitoring medication dispensing, comprising: (a) generating a digital communication between a medication monitoring module and at least one sensor of a user device; (b) directing, by the medication monitoring module, the at least one sensor to: (i) record dispensing of a medication from a medication storage unit, wherein the medication storage unit is not a part of the user device; and (ii) record the user prior to, during, or subsequent to the dispensing of the medication by the user; and (c) generating a plurality of digital data representative of the dispensing and the user, wherein the plurality of digital data is stored for access for monitoring medication dispensing from the medication storage unit by the user.

In some embodiments of any one of the methods or systems disclosed herein, the medication storage unit is a shelf.

In some embodiments of any one of the methods or systems disclosed herein, the medication storage unit is an automated dispensing machine.

In some embodiments of any one of the methods or systems disclosed herein, the at least one sensor comprises two or more cameras. In some embodiments, the two or more cameras have different optical axes. In some embodiments, the at least one sensor is capable has an angle of view of at least about 90, 120, 150, 180, 210, 240, 270, 300, 330, 345, 350, 355, 356, 357, 358, 359, 360 degrees. In some embodiments, the angle of view is measured horizontally. In some embodiments, the at least one sensor is at least one camera.

In some embodiments of any one of the methods or systems disclosed herein, the method further comprises (1) directing, by the medication monitoring module, the at least one sensor to record an additional inventory of an existing medication in the medication storage unit, and (2) generating an additional digital data representative of the additional inventory. In some embodiments, the method further comprises, based at least in part on the additional digital data, determining if the medication is (A) expired or (B) about to expire within a pre-determined time period. In some embodiments, the pre-determined time period is between about 1 day and about 2 weeks. In some embodiments, the pre-determined time period is between about 1 day and about 1 week. In some embodiments, upon the determining, alerting that the medication is (A) expired or (B) about to expire within the pre-determined time period, via the user device.

In some embodiments of any one of the methods or systems disclosed herein, the medication is a single dose. In some embodiments, the medication is multiple doses.

In some embodiments of any one of the methods or systems disclosed herein, the medical storage unit can be any one of various units configured to store one or more medications that can be inventoried. In some embodiments, the medical storage unit may comprise a shelf at a store for displaying medications. In some embodiments, the medical storage unit may be a delivery truck. In some embodiments, the medical storage unit may be a carrier for the one or more medications. In some embodiments, the medical storage unit may be a medicine cabinet.

Recognized herein is also a need for methods and systems for monitoring various sensitive items, e.g., seized illicit drugs, weapons, ammunition, and various contraband that, in some examples, promotes entities to manage the sensitive items securely while storing, transporting, disposing, and/or destroying the sensitive items.

In some aspects, the present disclosure discloses a method for monitoring contraband. In some embodiments, the method comprises generating a digital communication between a monitoring module and at least one sensor of a user device. In some embodiments, the method comprises directing, by the monitoring module, the at least one sensor to record disposal or destruction of contraband by a user and record the user prior to, during, or subsequent to the disposal or the destruction of the contraband by the user. In some embodiments, the method comprises generating a plurality of digital data representative of the disposal or the destruction and the user. In some embodiments, the plurality of digital data is stored for access for monitoring the disposal or the destruction of the contraband by the user. In some embodiments, the contraband is selected from the group consisting of: weapons, ammunition, illicit drugs, and commercial chemicals.

In some aspects, the present disclosure discloses a method for monitoring contraband wasting. In some embodiments, the method comprises generating a digital communication between a monitoring module and at least one sensor of a user device. In some embodiments, the method comprises directing, by the monitoring module, the at least one sensor to: read an identifier of a contraband waste unit; record disposal of a contraband to the contraband waste unit; and record the user prior to, during, or subsequent to the disposal of the contraband by the user. In some embodiments, the method comprises generating a plurality of digital data representative of the identifier of the contraband waste unit, the disposal, and the user. In some embodiments, the plurality of digital data is stored for access for monitoring wasting of the contraband into the contraband waste unit by the user.

In some aspects, the present disclosure discloses a method for contraband wasting. In some embodiments, the method comprises recording disposal of a contraband to a contraband waste unit by a user. In some embodiments, the method comprises generating a digital data representative of the disposal. In some embodiments, the method comprises providing access to the digital data to (i) an auditor of the contraband and/or (ii) a tracker of the contraband, wherein the disposed contraband is not shipped to (i) and/or (ii).

In some aspects, the present disclosure discloses a method for monitoring contraband wasting. In some embodiments, the method comprises providing a digital data indicative of a contraband. In some embodiments, the method comprises providing an instruction for disposal of the contraband to a designated receptacle of a plurality of receptacles of the contraband waste unit In some embodiments, the method comprises recording the disposal of the contraband to the designated receptacle.

Recognized herein is also a need for methods and systems for monitoring goods rendered unfit for sale to consumers, e.g., expired foodstuffs, recalled items, unpopular items, that, in some examples, promotes entities to manage the goods securely while storing, transporting, disposing, and/or destroying the goods.

In some aspects, the present disclosure discloses a method for monitoring goods rendered unfit for sale to consumers. In some embodiments, the method comprises generating a digital communication between a monitoring module and at least one sensor of a user device. In some embodiments, the method comprises directing, by the monitoring module, the at least one sensor to record disposal or destruction of the goods by a user and record the user prior to, during, or subsequent to the disposal or the destruction of the goods by the user. In some embodiments, the method comprises generating a plurality of digital data representative of the disposal or the destruction and the user. In some embodiments, the plurality of digital data is stored for access for monitoring the disposal or the destruction of the goods by the user. In some embodiments, the goods are selected from the group consisting of: expired items, recalled items, damaged items, and returned items. In some embodiments, the goods are selected from the group consisting of: expired foodstuffs, expired drugs, recalled foodstuffs, recalled drugs, returned foodstuffs, returned drugs, damaged electronics, recalled electronics, returned electronics, damaged clothing, recalled clothing, and returned clothing.

In some aspects, the present disclosure discloses a method for monitoring wasting of goods rendered unfit for sale to consumers. In some embodiments, the method comprises generating a digital communication between a monitoring module and at least one sensor of a user device. In some embodiments, the method comprises directing, by the monitoring module, the at least one sensor to: read an identifier of a goods waste unit; record disposal of a good to the goods waste unit; and record the user prior to, during, or subsequent to the disposal of the goods by the user. In some embodiments, the method comprises generating a plurality of digital data representative of the identifier of the goods waste unit, the disposal, and the user. In some embodiments, the plurality of digital data is stored for access for monitoring wasting of the good into the goods waste unit by the user.

In some aspects, the present disclosure discloses a method for wasting goods rendered unfit for sale to a consumer. In some embodiments, the method comprises recording disposal of a good to a goods waste unit by a user. In some embodiments, the method comprises generating a digital data representative of the disposal. In some embodiments, the method comprises providing access to the digital data to (i) an auditor of the good and/or (ii) a tracker of the good, wherein the disposed good is not shipped to (i) and/or (ii).

In some aspects, the present disclosure discloses a method for monitoring contraband wasting. In some embodiments, the method comprises providing a digital data indicative of a contraband. In some embodiments, the method comprises providing an instruction for disposal of the contraband to a designated receptacle of a plurality of receptacles of the contraband waste unit. In some embodiments, the method comprises recording the disposal of the contraband to the designated receptacle.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates an exemplary flowchart of a method of monitoring medication wasting.

FIG. 2 illustrates another exemplary flowchart of a method of monitoring medication wasting.

FIG. 8 illustrates an exemplary flowchart of a method of monitoring handling of item(s).

FIG. 12 schematically illustrates example drawers of an automated dispensing machine, each drawer comprising a plurality of pockets for different medication types and/or dosages.

FIG. 15 provides various exemplary aspects of healthcare facilities/users that are solved/reduced/eliminated by various embodiments of the systems and methods of the present disclosure.

FIG. 17 schematically illustrates a comparison of medication collection and destruction between (i) art and (ii) the systems and methods of the present disclosure. For example, the systems and methods of the present disclosure can (1) eliminate middleman time and expense, (2) eliminate pack and ship time and expense, (3) eliminate the need to ship the medication from the wasting/collection site (e.g., pharmacy) to another location (e.g., middle distributor, destruction site, etc.) by enabling on-site medication wasting/collection and destruction, and/or (4) incentives (e.g., faster payment of credits to the wasting/collection site (e.g., pharmacy).

DETAILED DESCRIPTION

Figure 3:
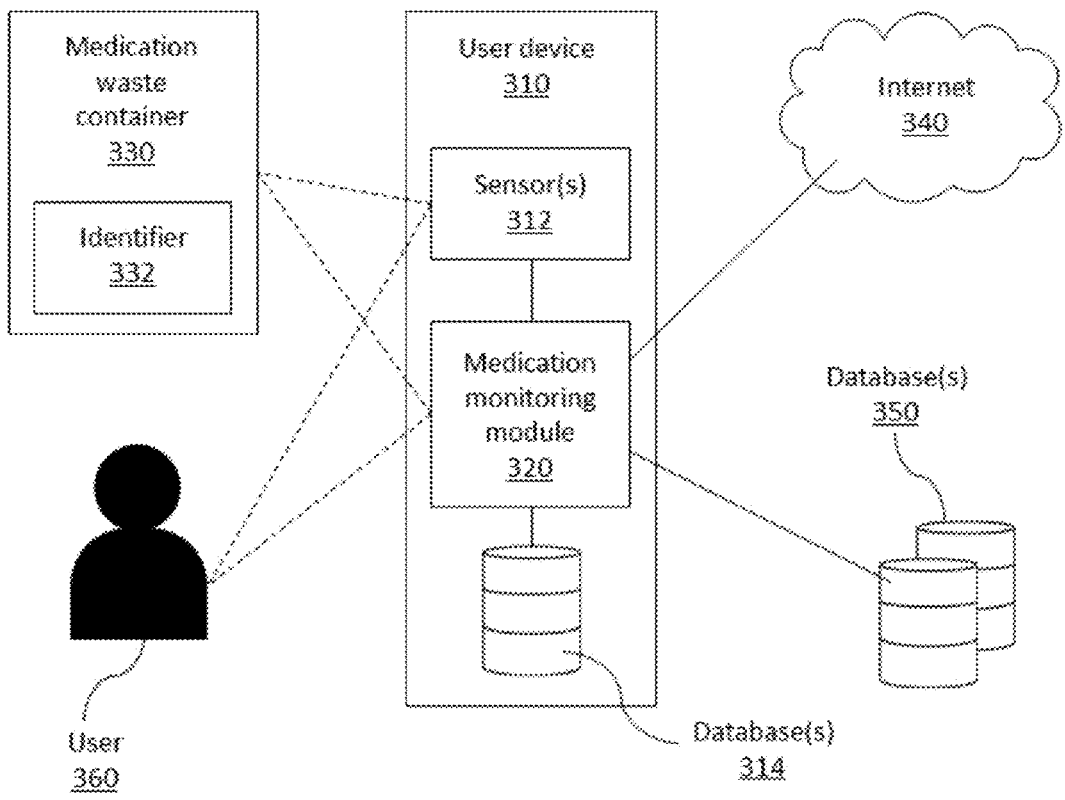
FIG. 3 schematically illustrates an exemplary ecosystem comprising a medication monitoring module.

Reference will now be made in detail to some exemplary embodiments of the disclosure, examples of which are illustrated in the accompanying drawings. Wherever possible, the same reference numbers will be used throughout the drawings and disclosure to refer to the same or like parts.

I. Medication Monitoring Applications

A. Introduction

Unused or leftover medication (e.g., due to recalls, expiration, returns, excess, general waste, etc.) can be disposed and collected in medical facilities (e.g., hospitals, private practices, outpatient clinics, veterinarians, podiatrists, etc.) or pharmacies (e.g., chains, independents, mail-order, in-supermarket, etc.). The medications being collected can be disposed by subjects taking the medications (e.g., patients), healthcare providers, or pharmacists. The medications can be prescribed or over-the-counter medications.

In some cases, the disposed/wasted medications can be picked up by a consolidator, such as reverse distributors or reverse wholesalers. The consolidator can send the disposed medications back to a respective manufacturer, destroy them, or repurpose them. In some cases, the consolidator can verify the disposed medications to confirm that proper medications have been indeed wasted. In examples, e.g., at retail pharmacy chains (e.g., CVS, Walgreens), the disposed and collected medications can be sent from each store to a corporate warehouse, wherein the medications can be consolidated and sent back to manufacturers, handled by reverse distributors/wholesalers, destroyed, etc. Additional examples of retailers may be supermarkets or an online shopping service.

In some cases, the unused or leftover medications can be diverted (e.g., intentionally for misuses by the user of the medications, healthcare providers, or a third party; unintentionally lost or neglected to return/waste, etc.) for misuses. However, there remains an unmet need for an effective oversight for such mismanagement. There remains an unmet need for an interested party (e.g., medical facilities, pharmacies, consolidator, manufacturers, etc.) to oversee various aspects of medication handling, e.g., via a visual proof of wasting or destruction of unused/leftover medications. There also remains an unmet need for storing such visual proof in a database (e.g., a centralized database) for retrieval of such visual proof when needed.

B. Methods and Systems for Medication Monitoring

Methods and systems, as provided herein, can be capable of addressing the above shortcomings of conventional systems and practices for medication management in medical institutions, such as, for example, homes (e.g., homes of a patient), hospitals (e.g., public, private, military, or non-military hospitals), medical offices (e.g., physician clinics, dental clinics, ambulatory surgery centers, same-day or other non-hospital surgery facilities, a medication dispensing room or a pharmacy, such as a place having an automated dispensing machine (ADM), etc.), non-acute healthcare institutions (e.g., long term care facilities), skilled nursing facilities, assisted living facilities, hospice, clinics (e.g., pain clinics), emergency response units (e.g., paramedic transportations, emergency medical service (EMS) transportations, etc.), veterinary hospitals, veterinary clinics, veterinary laboratories, medical research facilities, hospice, long-term acute care (LTAC) facility, nursing home, assisted living facility, pharmacy, in-pharmacy clinic, law enforcement sites, etc.

Methods and systems, as provided herein, can utilize a medication monitoring module (e.g., a software such as a graphical user interface (GUI) operable on a user device, such as a mobile application operable on a mobile phone or a software operable on a computer device) to (1) record disposal of the medication to a medication waste unit, (2) record the user (e.g., hands, face, etc.) that is disposing the medication to the medication waste unit, (3) record the medications being disposed to the medication waste unit, (4) analyze (e.g., identify, measure, etc.) the medication being disposed, (5) analyze (e.g., identify) the user, (6) generate digital data representative of one or more of (1)-(5), (7) store the digital data, (8) transmit the digital data to a database in digital communication with the medication monitoring module, and/or (9) communicate with the user. In some cases, the medication waste unit can be any container capable of containing medications (e.g., existing or new forms of assay/medication collection). In some cases, the digital data generated by the medication monitoring module, as disclosed herein, can be used (e.g., read, analyzed, etc.) in real-time or at a later timepoint to track proper disposal/wasting of the medication by the user.

The term "real-time" or "real time," as used interchangeably herein, generally refers to an event (e.g., an operation, a process, a computation, a calculation, an analysis, a visualization, movement of a component of a system, etc.) that is performed using recently obtained (e.g., collected or received) data. In some cases, a real time event may be performed almost immediately or within a short enough time span, such as within at least 0.0001 millisecond (ms), 0.0005 ms, 0.001 ms, 0.005 ms, 0.01 ms, 0.05 ms, 0.1 ms, 0.5 ms, 1 ms, 5 ms, 0.01 seconds, 0.05 seconds, 0.1 seconds, 0.5 seconds, 1 second, or more. In some cases, a real time event may be performed almost immediately or within a short enough time span, such as within at most 1 second, 0.5 seconds, 0.1 seconds, 0.05 seconds, 0.01 seconds, 5 ms, 1 ms, 0.5 ms, 0.1 ms, 0.05 ms, 0.01 ms, 0.005 ms, 0.001 ms, 0.0005 ms, 0.0001 ms, or less.

In some cases, the medication monitoring module, as disclosed herein, and uses thereof can decentralize previously practiced medication wasting/return process, to, for example, allow hospitals or pharmacies to handle the returns on their own, without the need to use a reverse distributor or, in the case of pharmacy chains, consolidate to a warehouse for processing. Thus, the methods and systems disclosed herein can enable hospitals, pharmacies, etc. to obtain their credit or rebate (e.g., mail-in check, direct-deposit, electronic rebate payment, etc.) quicker rather than waiting for the reverse distributors/wholesalers to complete the task. In some cases, the monitoring of medication wasting (e.g., supply chain accountability) as disclosed herein can be enhanced via blockchain technology.

In some embodiments, the medication monitoring module can be operable (e.g., installed in) a user device, such as, for example, a mobile device (e.g., a cell phone) or a wearable device (e.g., a smart watch). The medication monitoring module can be operatively linked to any container to utilize such container as a medication waste unit. The medication monitoring module can identify an individual responsible for disposing the medication to the medication waste unit (e.g., via directing one or more sensors of the user device). The medication monitoring module can identify the disposed medication (e.g., via directing the one or more sensors of the user device to record (i) the medications (e.g., disposed or dispensed medications) or (ii) an identifier (e.g., a barcode) of a packaging holding the medications prior to disposing the medications to the medication wasting container). In some examples, the medication monitoring module can be programmed to analyze one or more recorded images/videos of the medications taken prior to, during, or subsequent to wasting of the medications into the medication wasting container, thereby to identify the medications (e.g., name, types, dosage, etc.). The medication monitoring module can direct data entry and/or data streaming to and from a database operatively coupled to the medication monitoring module. Such database can be, for example, (i) a database of the medication monitoring module, (ii) a cloud service database operatively coupled to the medication monitoring module, (iii) a collective database (e.g., a centralized database, a blockchain database, etc.) that is in digital communication with a plurality of medication monitoring modules operable in a plurality of user devices.

In some embodiments, the amount of medications being wasted can be related to how much medications is left over in a source of the medications (e.g., inventory). As such, the medication monitoring module can perform analytics on what and how much medication is wasted, e.g., to determine what is expected to be remaining and/or what (e.g., type or amount) is needed to be supplied in inventory.

In some embodiments, the user (e.g., an authorized user) of the medication monitoring module can be captured in one or more images or videos (e.g., via a camera of the user device, as directed by the medication monitoring module) along with the medications being disposed. In some cases, artificial intelligence and machine learning algorithms can be utilized to analyze the images/videos and verify/identify the user.

In some embodiments, the medication monitoring module can be in digital communication with other medication monitoring modules operated in other user devices and/or with other databases for data stream or exchange. Such data can represent information relevant to the disposal and return of the medications. In some cases, such data can be transmitted to a centralized database or a centralized analysis module to retrieve the medication return prior to collection of the disposed medications to a centralized location. Thus, identity and/or a quantity of the medications being disposed can be verified, confirmed, or rewarded in real-time or near real-time prior to actual verification of the disposed medications by a third party. Non-limiting examples of the centralized database or centralized analysis module can include, but are not limited to, government agencies (e.g., Drug Enforcement Administration (DEA), National Library of Medicine (NLM), Food and Drug Administration (FDA), Centers for Disease Control and Prevention (CDC), etc.). central hospitals, central pharmacies, manufactures (e.g., drug manufacturers), distributors (e.g., drug distributors), etc.

In some embodiments, the medication monitoring module disclosed herein can display a message to the user (e.g., via a display unit and/or an audio unit of the user device), and the message can comprise various information, such as, for example, alerts about return information or health/safety recalls of the medications. In some cases, data collected by the medication monitoring module can be integrated with alerts about medication return information or health/safety recalls for fast processing, where delays may exacerbate a safety issue (recall) or increase associated costs.

In some embodiments, the medication monitoring module disclosed herein can verify proper placement and/or routing of the medications, e.g., depending on their destination. The module can verify the medication (e.g., using data collected via the user device, such as images or videos of the medication captured by a camera of the user device), confirm a location of the medication waste unit via an identifier (e.g., a scannable code, such as a machine readable code (MRC)) on the medication waste unit, and/or verify the medication waste unit, such that the user can be directed to properly dispose the medications (e.g., hazardous medications) into a correct medication waste unit. For example, the medication monitoring module and help or ensure that hazardous medications can be segregated from other waste products. For example, the module can confirm that a narcotic medication (e.g., opioid, fentanyl, hydrocodone, etc.) has been properly disposed into a narcotics waste bin (e.g., NarcX bin) for neutralization, and the module can generate data representative of such information. In another example, the module can generate data suggesting that the collected medications, when appropriate, can be packaged and shipped back to the manufacturer. In a different example the module can generate data suggesting that the medications can be allocated for a charitable donation.

The term "medication waste unit" generally refers to an example of an item(s) receiving unit that is configured to receive medication that is being disposed of or wasted. In some cases, a medication waste unit can be a container (i.e., medication waste container) (e.g., reservoir, box, container, cup, vat, pan, etc.) configured to hold at least a portion of the medication being disposed. The medication waste container can be sealed prior to and subsequent to receiving the disposed medication. Alternatively, the medication waste container may not and need to be sealed for its operation. In some cases, a medication waste unit may not and need not contain the medication being disposed. For example, a medication waste unit can comprise an inlet configured to receive the disposed medication and an outlet configured to direct the received medication to a destination (e.g., drainage). For example, a sink can be used as a medication waste unit, in which any unused or leftover portion of non-dangerous, non-controlled medication can be disposed into the sink, and such disposal can be monitored (e.g., captured via images/videos) by the medication monitoring module as disclosed herein.

In some embodiments, the medication waste unit can comprise an identifier (e.g., at least 1, 2, 3, 4, 5, or more identifiers; at most 5, 4, 3, 2, or 1 identifier(s)) to identify the medication container. The medication waste unit can be manufactured with the identifier. Alternatively, the medication waste unit and the identifier can be manufactured/provided separately, and the identifier can be coupled (e.g., attached) to the medication waste unit, such that the medication waste unit can be operable with the medication monitoring module. For example, the identifier can be a sticker or a magnet that can be attached to a surface of the medication waste unit. In some cases, the medication waste unit can comprise a housing. A portion (e.g., neck, collar, etc.) of the housing can be configured to couple (e.g., releasably couple) to another object (e.g., cap, sleeve, etc.). The portion of the housing and the other object can be coupled (e.g., interlocked) to form the identifier (e.g., RVC). In some examples, the identifier can be used as a seal indicating that the medication waste unit has not been opened or tampered. In some examples, the identifier can be used as a seal indicating that the medication waste unit has been used and locked.

In some embodiments, the identifier as disclosed herein (e.g., a machine readable code (MRC) or an identification device) can be used for monitoring or tracking of an object on which the identifier is attached to (e.g., an item(s) collection unit, a medication waste unit, medication package, etc.), or retrieving information about such object or one or more contents within the object. The MRC may be a barcode (e.g., a linear barcode, a matrix barcode, etc.). The identification device may be a communications device, such as a radio frequency device (e.g., a radio-frequency identification (RFID) system, a near-field communication (NFC) system, improvements thereof, etc.) or other internal integrated circuits. The identification device may be an electronic chip.

In some embodiments, the identifier as disclosed herein (e.g., the identifier of the medication waste unit) can be a reconstructable visual code (RVC). The RVC can be a dynamic visual code that is divided into a plurality of portions configured to be combined (e.g., upon activation) to form a functional visual code that is readable. The RVC can comprise a physical code (PHC) and/or an augmented reality code (ARC). Examples of the RVC and methods of use thereof are provided in, for example, International Patent Application No. PCT/US2020/019122, which is entirely incorporated herein by reference. In some cases, a medication waste unit can be manufactured with at least a portion of the RVC. In some cases, at least a portion of the RVC can be provided separately from the medication waste unit, and the at least the portion of the RVC can be attached to the medication waste unit (e.g., by the user who is responsible for the medication disposal, by a staff of a medical facility, etc.), such that the medication waste unit can be recognized and registered by the medication monitoring module or an analysis module connected thereto, upon reading of the RVC.

In some embodiments, the user of the medication monitoring module as disclosed herein can comprise an identifier for identifying, monitoring, or tracking the user during use of the medication monitoring module. The identifier can be a wearable identifier, e.g., a wristband, an identifier (ID) tag, etc. Alternatively, biometrics of the user can be used as an identifier of the user (e.g., voice recognition, facial recognition, thumb print, user identification via heart rate or breathing rate, etc.). In some cases, methods based on artificial intelligence (e.g. machine learning, deep learning) can be used to identify and/or confirm identify of the user (e.g., compare the facial identification of the purported user to a database of authorized users). Such identification can provide another level of security in monitoring medications.

In some cases, voice recognition can be used to operate (e.g., touchless operation) any aspect of the medication monitoring module. Voice recognition can be used to identify the user and/or the patient. Voice recognition can be used to instruct an operation of the medication monitoring module. For example, in situations where looking at a display or interacting with a display may not be possible (e.g., when the user is using both hands for medication wasting, medication retrieval, and/or patient treatment), the user may use his or her voice to provide commands to the medication monitoring module, and such commands can be recognized by the medication monitoring module (e.g., via artificial intelligence, similar to Google Assistant, Alexa, Siri, Bixby, etc.) to execute one or more functions of the medication monitoring module. In another example, a user of the medication monitoring module may be far away from the user device and thus not able to interact with the medication monitoring module via a graphical user interface of the medication monitoring module, e.g., during medication wasting, medication retrieval, and/or patient treatment, and the voice recognition capability disclosed herein can allow the user to still operate aspect(s) of the medication monitoring module. In another example, the user may be wearing gloves (e.g., sterile gloves) and thus not able to interact with the graphical user interface of the medication monitoring module, and the voice recognition capability disclosed herein can allow the user to still operate aspect(s) of the medication monitoring module.

In some embodiments, one or more sensors of the user device (e.g., microphone, camera, thumb-print reader, etc.) can be operated by the medication monitoring module to detect or scan the identifier as disclosed herein. The user device can comprise at least 1, 2, 3, 4, 5, or more sensors (e.g., camera(s)). In some cases, the user device can comprise a plurality of sensors (e.g., at least 2, 3, 4, 5, or more cameras). In some examples, the plurality of sensors can have optical axes that are the same. Alternatively, the plurality of sensors can have optical axes that are different (e.g., not parallel to each other). An angle between a first optical axis of a first sensor of the user device and a second optical axis of a second sensor of the user device can be at least 1, 2, 3, 4, 5, 10, 15, 20, 30, 40, 50, 60, 70, 80, 90 degrees or more. An angle between a first optical axis of a first sensor of the user device and a second optical axis of a second sensor of the user device can be at least 90, 80, 70, 60, 50, 40, 30, 20, 15, 10, 5, 4, 3, 2, or 1 degree. In some examples, the plurality of sensors can have the same optical axis, but in opposite directions (e.g., a "front" facing camera and a "back" facing camera"). Alternatively, the user device can be operatively coupled to an identifier reader, such as a scanner, a barcode reader, RFID reader, a NFC reader, etc., to detect or scan the identifier. The identifier reader can be operatively coupled to (e.g., communicatively coupled to) the user device.

In some cases, the one or more sensors (e.g., camera(s)) of the user device can be configured to track movement of a target (e.g., an object or a subject).

In some embodiments, the medications disposed into the medication waste unit and monitored via the medication monitoring module, as disclosed herein, can be physically analyzed (e.g., quantified, counted, etc.). In some cases, once the module analyzes data of the disposed medication (e.g., item, quantity, routing, etc. of the medication), the user can physically count and process the medications for neutralization, return, or storage. Alternatively, once the module analyzes data of the disposed medication (e.g., item, quantity, routing, etc. of the medication), the medication can be collected at a centralized site (e.g., along with the medication waste unit), and the centralized site's agent can analyze and quantify the collected medication.

In some embodiments, the medication monitoring module can direct one or more sensors (e.g., cameras) of the user device to capture digital images or videos of an identifier (e.g., a MRC, such as a barcode) of a packaging of the medication (i.e., medication package). By scanning the identifier of the packaging, the medication monitoring module can retrieve information about the medication, such as one or more of: (i) order or prescription of the medication, (ii) return/waste order information, (iii) stock keeping unit (SKU) number or national drug code (NDC) for the original medication (e.g., original pellet), master carton, inner carton, individual item, etc.

In some embodiments, medication monitoring module can direct one or more sensors (e.g., cameras) of the user device to capture digital images or videos of an identifier (e.g., a MRC, such as a barcode) of the medication waste unit. In some cases, such scanning of the identifier can be utilized to verify when the medication waste unit is being opened, closed, or manipulated to, for example, discourage, avoid, or capture tampering of the medication. In some cases, the medication waste unit can be configured to be opened or closed automatically without human input (e.g., via one or more motorized hinges). As such, the medication monitoring module can digitally communicate with the medication waste unit to direct the medication container to open and close.

In some embodiments, one or more reports with regards to the medication and disposal thereof (e.g., discrepancy report) can be generated by the medication monitoring module or an analysis module connected thereto. In some cases, such reports can be generated based on standards (or triggers) previously programmed into the medication monitoring module. Alternatively or in addition to, such reports can be generated based on user-defined triggers. Non-limiting examples of such trigger can include, but are not limited to (i) not scanning an identifier of the medication packaging or the medication waste unit, (ii) when an opening of the medication waste unit is ajar without being closed properly, or (iii) when a scanned identifier does not match an identifier of the proper medication waste unit.

In some embodiments, the medication monitoring module as disclosed herein can be platform-agnostic, and thus can be operable in any user device, such as, for example, a mobile phone, a mobile tablet, a desktop computer, a laptop computer, a smart watch, smart glasses, a digital assistant (e.g., a robot with a computer screen), any communications device (e.g., Vocera devices), etc.

In some embodiments, the medication monitoring module as disclosed herein can be in digital communication with (or operatively linked to) a software module of a different system (e.g., an automated dispensing machine (ADM) and/or electronic medical record (EMR) systems, inventory systems, warehouse management systems, accounting systems, other enterprise software, point-of-sale systems, etc.) to thereby (1) retrieve patient medical record, medication prescription record, medication wasting or dispensing order for each patient or (2) record medication disposal occurrence(s) to each patient's digital medical record. In some cases, an ADM as described herein can be a commercially available ADM including, for example the McLaughlin dispensing system, the Baxter ATC-212 dispensing system, Omnicell, and the Pyxis MedStation. In some embodiments, one or more of the containers, adapters or key devices disclosed herein can be stored in a drawer of the ADM (e.g., a CUBIE pocket in the Pyxis MedStation).

In some embodiments, the user device as disclosed herein may not and need not be a part of (e.g., a component within) the medication waste unit. In other words, the medication waste unit may not and need not be a part of (e.g., a component within) the user device. The user device and the container to be used as a medication waste unit can be provided as separate items. Thus, in some cases, a coupling unit can be used to couple the user device to the medication waste unit. In some examples, a coupling unit can be used to mount (or install) the user device at a certain position relative to the medication waste unit, such that a sensor (e.g., a camera) of the user device can record (e.g., capture one or more images or videos of) disposal of a medication into the medication waste unit. In an example, the user device or the medication waste unit can be releasable coupled to the coupling unit.

The term "coupling unit," as used herein, generally refers to a device configured to connect or complex two or more objects, such as a user device and an item collection unit (e.g., a medication waste unit). The coupling unit may comprise a first connection mechanism configured to connect to a first object (e.g., the user device) and a second connection mechanism configured to connect to a second object (e.g., the medication waste unit). The coupling unit can physically and operatively pair the two objects at, e.g., a desired distance between each other. In some cases, the coupling unit can be adjustable as to adjust a distance between the two objects. For example, the coupling unit can comprise an actuator mechanism (e.g., pneumatic actuator, spring actuator, motorized actuator, etc.) to facilitate a relative movement between the two objects (e.g., between the user device and the medication waste unit). In other cases, the distance between the two objects may not and need not be adjustable by the coupling unit. Non-limiting examples of the connection mechanism(s) utilized by the connection unit can include various male-to-female fasteners (e.g., mating or interlocking fasteners, hooks and holes, hooks and loops such as Velcro™, a female nut threaded onto a male bolt, a male protrusion inserted into a female indentation in LEGO blocks, a male threaded pipe fitted into a female threaded elbow in plumbing, a male universal serial bus (USB) plug inserted into a female USB socket, etc.), tethers (e.g., string tethers), adhesives (e.g., solids, semi-solids, gels, viscous liquids, etc.), magnets (e.g., electro-magnet or permanent magnet), and other grasping mechanisms (e.g., one or more robotic arms). In some examples, coupling between the coupling unit and any object (e.g., the user device, the medication waste unit, etc.) can be performed using an electric field between two plates. The coupling mechanism(s) as disclosed herein can be reversible or irreversible.

In some cases, the coupling unit can be mobile, e.g., a robotic coupling unit that can move from one place to another via motorized wheels. Alternatively, the coupling unit may not and need not be mobile (i.e., stationary).

In some cases, the coupling unit may not need to physically couple two objects. The coupling unit can be configured to hold one of the two objects in place, while the other of the two objects remains stationary on its own, such that the coupling unit operatively couples the two objects at a relative distance between the two objects.

In some cases, the coupling unit may be required for monitoring medication wasting, as disclosed herein. Alternatively, the coupling unit may not and need not be required for monitoring medication wasting (e.g., the medication waste unit can remain stationary on its own, and the user can hold the user device with one hand while disposing the medication with the other hand).

In some cases, monitoring medication wasting as disclosed herein may be performed without a coupling unit. In some examples, the medication monitoring module can be operatively coupled to a user device, and the user device may be handheld or worn by the user (e.g., on the user's wrist, neck, waist, etc.) for operation of the medication monitoring module. For example, when a mobile phone is used to monitor medication disposal, the medication monitoring module can help the user to position the mobile phone in the right place relative to the medication collection unit by displacing a visual cue (e.g., a virtual visual cue on a display of the mobile phone) to the user. The medication monitoring module can provide a visual cue to the user as to where to properly place the user device (e.g., a phone or mobile device), such that the sensor(s) (e.g., camera(s)) of the user device are properly aligned to capture the user and/or user's performance (e.g., medication wasting).

In some embodiments, the medication monitoring module as disclosed herein can be utilized for governing inventory of medications from (i) central pharmacy, to (ii) distribution, to (iii) wasting of any unused or leftover medications, and to (iv) collection of the wasted medications (e.g., to a centralized location).

In some embodiments, the medication monitoring module as disclosed herein can not only monitor medication wasting, but also (or alternatively) medication dispensing to monitor (i) the user or machine that is dispensing the medication, (ii) the recipient of the medication being dispensed, and (iii) the medication being dispensed. As such, the medication monitoring module can integrate various events related to a medication, e.g., manufacturing, packaging, dispensing, returning, and/or wasting processes.

In some embodiments, the medication monitoring module as disclosed herein can be configured to report images and/or videos captured during monitoring of the medication wasting or dispensing, as described herein. Such report comprising the images and/or videos can be displayed on the same user device that is used to operate the medication monitoring module. Alternatively, the report can be displayed on a different user device. Yet in another alternative, the report can be digitally transmitted to the user via the user's e-mail address or text messaging. In some cases, the report can also include analysis of the monitoring of medication wasting. Such report can be a visual report (e.g., comprising images, videos, or figures). The report as disclosed herein can also include timing of the monitored events and identification(s) of the user(s) that have been monitored or recorded.

In some cases, the report can tie together what has been instructed to be dispensed or wasted. As such, the report can be used to correlate the monitored act of medication handling (e.g., medication wasting, medication inventory, medication dispensing, medication prescription, etc.) with what has been ordered (e.g., by a physician).

FIG. 1 illustrates an example flowchart 100 of a method of monitoring medication wasting. The method can comprise generating a digital communication between a medication monitoring module and at least one sensor of a user device (process 110). For example, the medication monitoring module can be a software (e.g., a mobile application) that can be installed on the user device (e.g., a mobile phone), and the software can be turned on to generate such digital communication. The digital communication can allow the software to control one or more components (e.g., one or more sensors, such as one or more cameras) of the user device. The method can further comprise directing, by the medication monitoring module, at least one sensor of the user device to record disposal of a medication to a medication waste unit by a user (e.g., by a subject who was taking the medication, or a nurse) (process 120). The medication waste unit may not be a part of the user device. The method can further comprise directing, by the medication monitoring module, the at least one sensor of the user device to record the user prior to, during, or subsequent to the disposal of the medication by the user (process 130). The method can further comprise generating a plurality of digital data representative of the disposal and the user (process 140). The plurality of digital data can be stored for access for monitoring wasting of the medication into the medication waste unit by the user. At least a portion of the plurality of digital data can be stored in a database of the user device, a centralized database operatively coupled to the user device or the medication monitoring module, or both.

FIG. 2 illustrates an example flowchart 200 of a method of monitoring medication wasting. The method can comprise generating a digital communication between a medication monitoring module and at least one sensor of a user device (process 210). The method can further comprise directing, by the medication monitoring module, the at least one sensor to read a unique label of a medication waste unit (process 220). The method can further comprise directing, by the medication monitoring module, the at least one sensor to record disposal of a medication to the medication waste unit (process 230). The method can further comprise directing, by the medication monitoring module, the at least one sensor to record the user prior to, during, or subsequent to the disposal of the medication by the user (process 240). The method can further comprise generating a plurality of digital data representative of the unique label of the medication waste unit, the disposal, and the user (process 250). As described herein, the plurality of digital data can be stored for access for monitoring wasting of the medication into the medication waste unit by the user.

FIG. 3 schematically illustrates an exemplary ecosystem comprising a medication monitoring module. The medication monitoring module can be configured to perform any of the methods disclosed herein (e.g., as described in FIGS. 1 and 2). The ecosystem can comprise a user device 310, such as, for example, a mobile phone of a user or the user's caregiver (360), that of the medication or that of a healthcare provider (e.g., a hospital system, a nurse, etc.), etc. The user device 310 can comprise one or more sensors 312, such as, for example, one or more cameras. In some cases, the user device 310 can comprise (i) a first camera 312-a disposed on a first surface of the user device 310 (e.g., a "front" facing camera) and (ii) a second camera 312-b disposed on a second and different surface of the user device 310 (e.g., a "back" facing camera), such that the first camera 312-a can capture one or more images/videos of the user 360 (e.g., the user's face) and the second camera 312-b can capture one or more images/videos of the medication and/or the medication waste unit 330 prior to, during, or subsequent to wasting of the medication into the medication waste unit 330. In an example, the first camera 312-a can record a face of the user 360 while (or at the same time) the second camera 312-b can capture the user's hand, the medication, and the medication waste unit 330 to record the disposal. A medication monitoring module 320 can be installed as a software (e.g., a mobile application) on the user device, and the medication monitoring module 320 can be granted access to control the sensor(s) 312 of the user device 310, the database(s) 314 of the user device 310, or both. The medication monitoring module 320 can direct the sensor(s) 312 to scan or capture an identifier 332 (e.g., a machine readable code (MRC), such as a barcode or RVC) prior to, during, or subsequent to wasting of the medication into the medication monitoring container 330. In some cases, the medication monitoring module 320 can be operatively coupled to the internet 340 to retrieve information about the user 360, the user device 310, the medication waste unit 330, the identifier 332 of the medication waste unit 330, the medication, prescription of the medication, disposal or wasting order of such medication, original packaging of the medication, etc. In some cases, the medication monitoring module 320 can be operatively coupled to one or more centralized database(s) 350, as disclosed herein, to transmit digital data to or from the database(s) 350.

Figure 4:
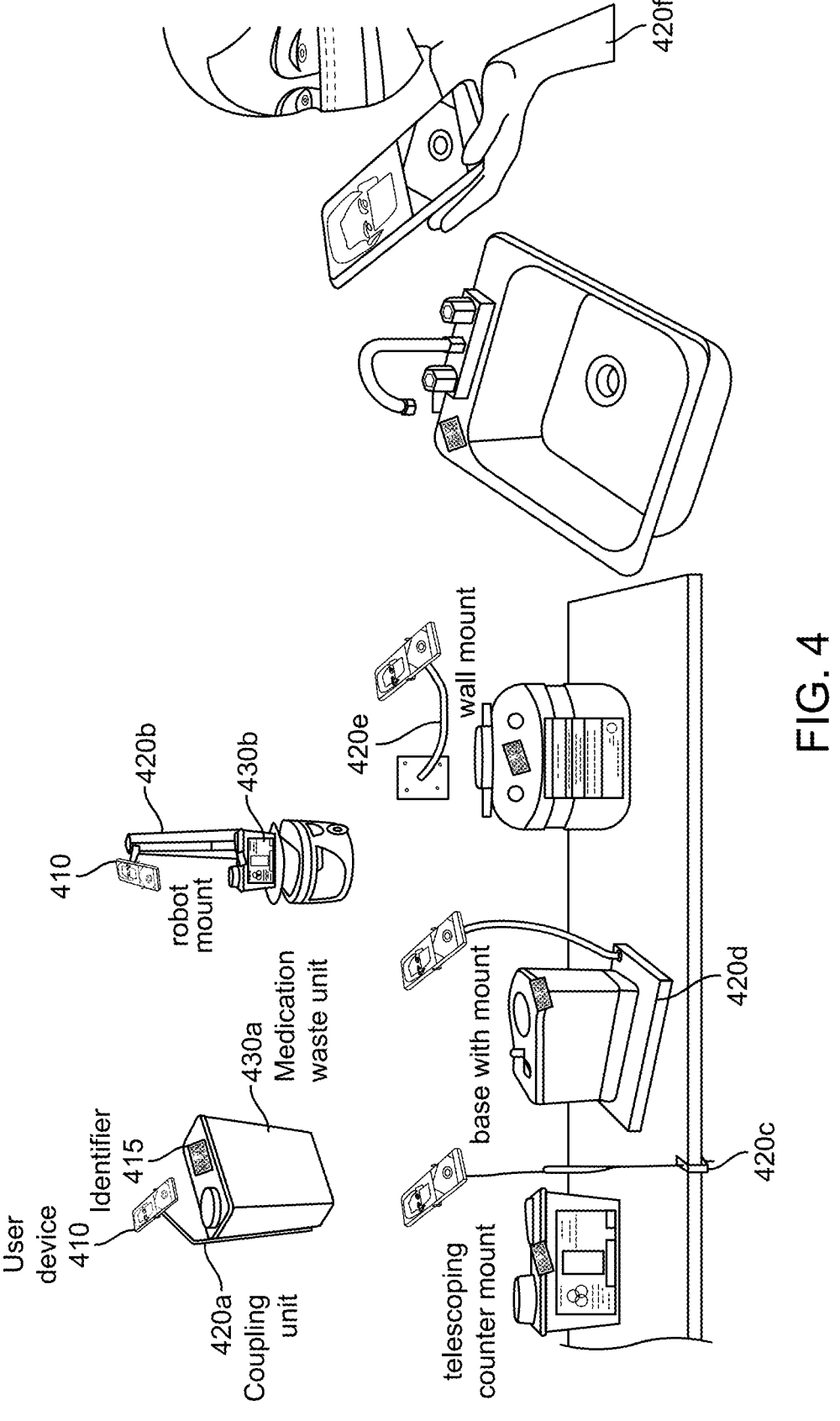
FIG. 4 schematically illustrates examples of an ecosystem comprising a medication monitoring module.

FIG. 4 schematically illustrates examples of an ecosystem comprising a medication monitoring module. In an example, a user device 410 can be a mobile phone, in which the medication monitoring module is programmed (e.g., installed) as a software. The user device 410 can be operatively coupled to a medication waste unit 430, such as a medication neutralization box 430a (e.g., NarcX), via a coupling unit 420, such as a mobile device mount 420a. In another example, the coupling unit can be a robot mount 420b configured to (i) hold a medication waste unit 430b and the user device 310 and (ii) be movable among various locations. In a different example, the coupling unit can be a telescoping counter mount 420c. The coupling unit 420c may not be physically coupled to a medication waste unit. In a different example, the coupling unit can be a base mount 420d comprising (i) a base to hold a medication waste unit and (ii) an arm to hold a user device 310. In a different example, the coupling unit can be a wall mount 420e comprising an arm to hold a user device 310. The coupling unit 420e may not be physically coupled to a medication waste unit. In some cases, a separate coupling unit may not be needed for the methods of medication monitoring as disclosed herein. For example, a user's arm 420f can hold the user device such that the medication monitoring module of the user device can monitor the user and the disposal of the medication into the medication waste unit.

In some cases, the medication waste unit can comprise an additional identifier. The additional identifier can represent completion of medication wasting into the medication waste unit. The additional identifier can be visible upon completion of medication wasting into the medication waste unit, e.g., when an amount (e.g., volume, weight, number, etc.) of medication disposed into the medication waste unit is above a predetermined threshold.

Figure 5A:
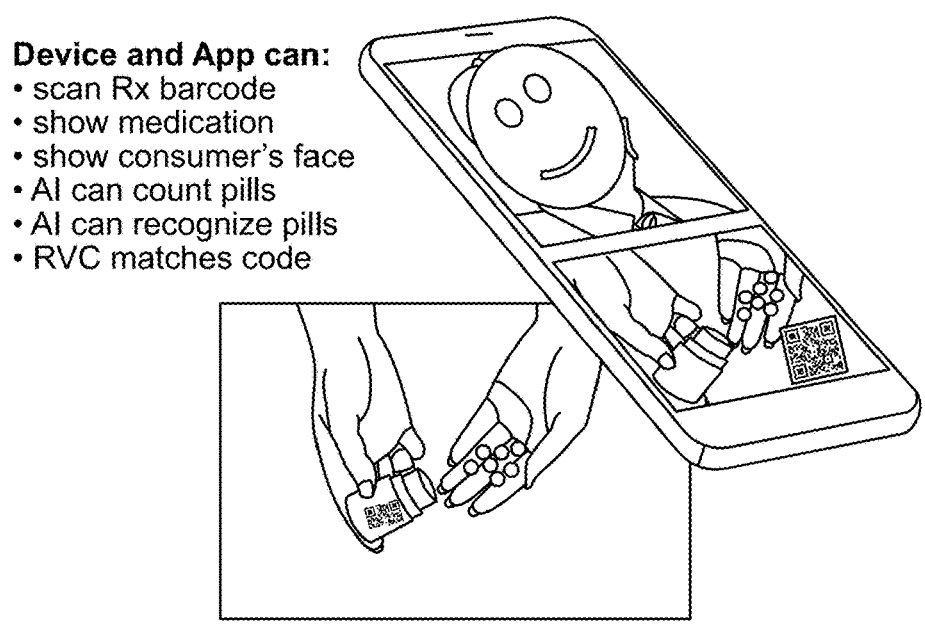
FIGS. 5A and 5B schematically illustrate exemplary additional applications of a medication monitoring module.

In some embodiments, the medication monitoring module as disclosed herein can be used to monitor use (or consumption) of medications by the user. As illustrated in FIG. 5A, the medication monitoring module can be programmed in the user device, and the medication monitoring module can utilize a front facing sensor (e.g., camera) to monitor the user and a back facing sensor (e.g., camera) to monitor the user's access to a medication package for medication consumption. In some cases, the monitoring by the sensors can be displayed on a display of the user device in real-time. In some cases, the medication package (e.g., pill bottle) can comprise an identifier (e.g., a MRC, such as a RVC). The medication monitoring module can direct a sensor (e.g., camera) of the user device to scan the identifier of the medication package and generate data accordingly. Subsequently or simultaneously, the medication monitoring module or a medication analysis module that is operatively linked to the medication monitoring module can analyze such data to, for example, identify the medication, quantify the medication (e.g., pill counting), verify the medication package, etc.

Figure 5B:
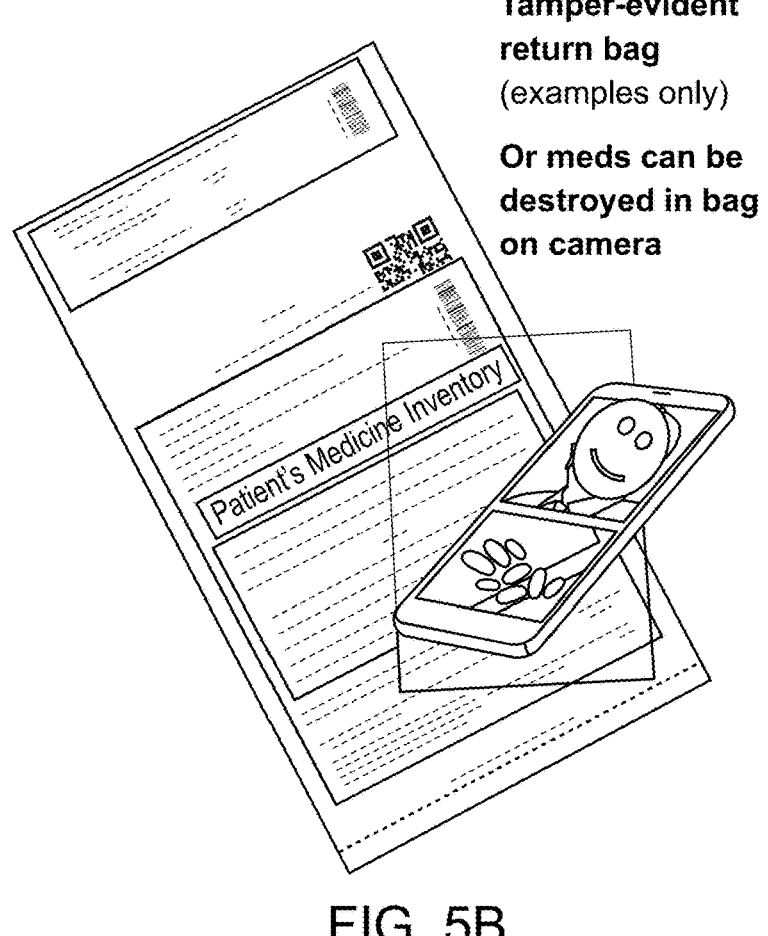

In some embodiments, the medication waste unit can be a medication transfer bag. As illustrated in FIG. 5B, the medication transfer bag can be a medication return bag (e.g., a tamper-evident return bag, a medication transfer bag, the bottle that the medication has been originally prescribed with, etc.) that can be sealed and mailed to a medication return site (e.g., a centralized collection site). The medication monitoring module can be programmed in the user device, and the medication monitoring module can utilize a front facing sensor (e.g., camera) to monitor the user and a back facing sensor (e.g., camera) to monitor the user's disposal of medication (e.g., unused or leftover medication)

into the medication return bag. In some cases, the monitoring by the sensors can be displayed on a display of the user device in real-time. In some cases, the medication return bag can comprise an identifier (e.g., a MRC, such as a RVC). The medication monitoring module can direct a sensor (e.g., camera) of the user device to scan the identifier of the medication package and generate data accordingly. Subsequently or simultaneously, the medication monitoring module or a medication analysis module that is operatively linked to the medication monitoring module can analyze such data to, for example, identify the medication, quantify the medication (e.g., pill counting), verify the medication package, initiate tracking of the medication return, etc. In some cases, the medications can be neutralized or destroyed once disposed into the medication return bag, and the medication monitoring module can record such process for monitoring/tracking.

Figure 13:
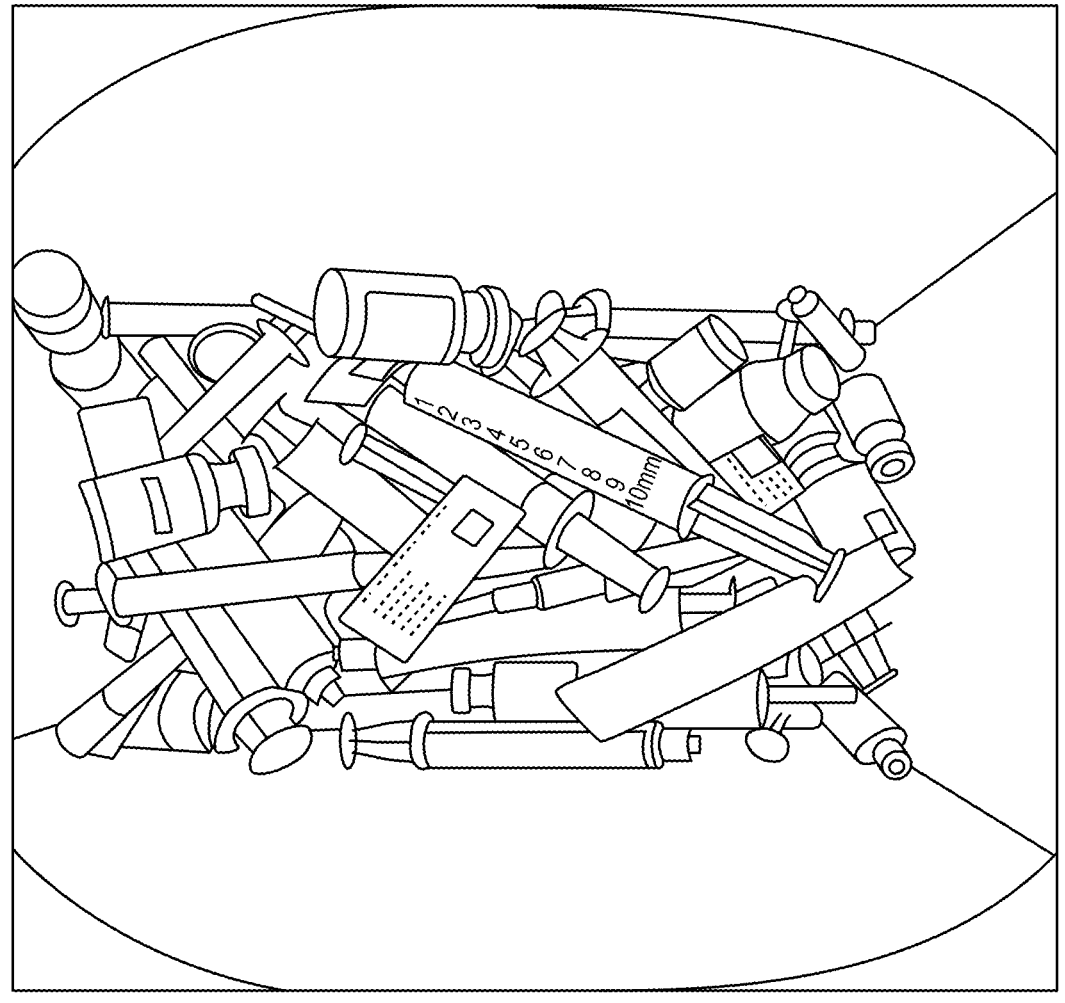
FIG. 13 shows an example image of a plurality of medications packaging (e.g., bottles, syringes, etc.) that have been disposed into a medication waste container.
Figure 14:
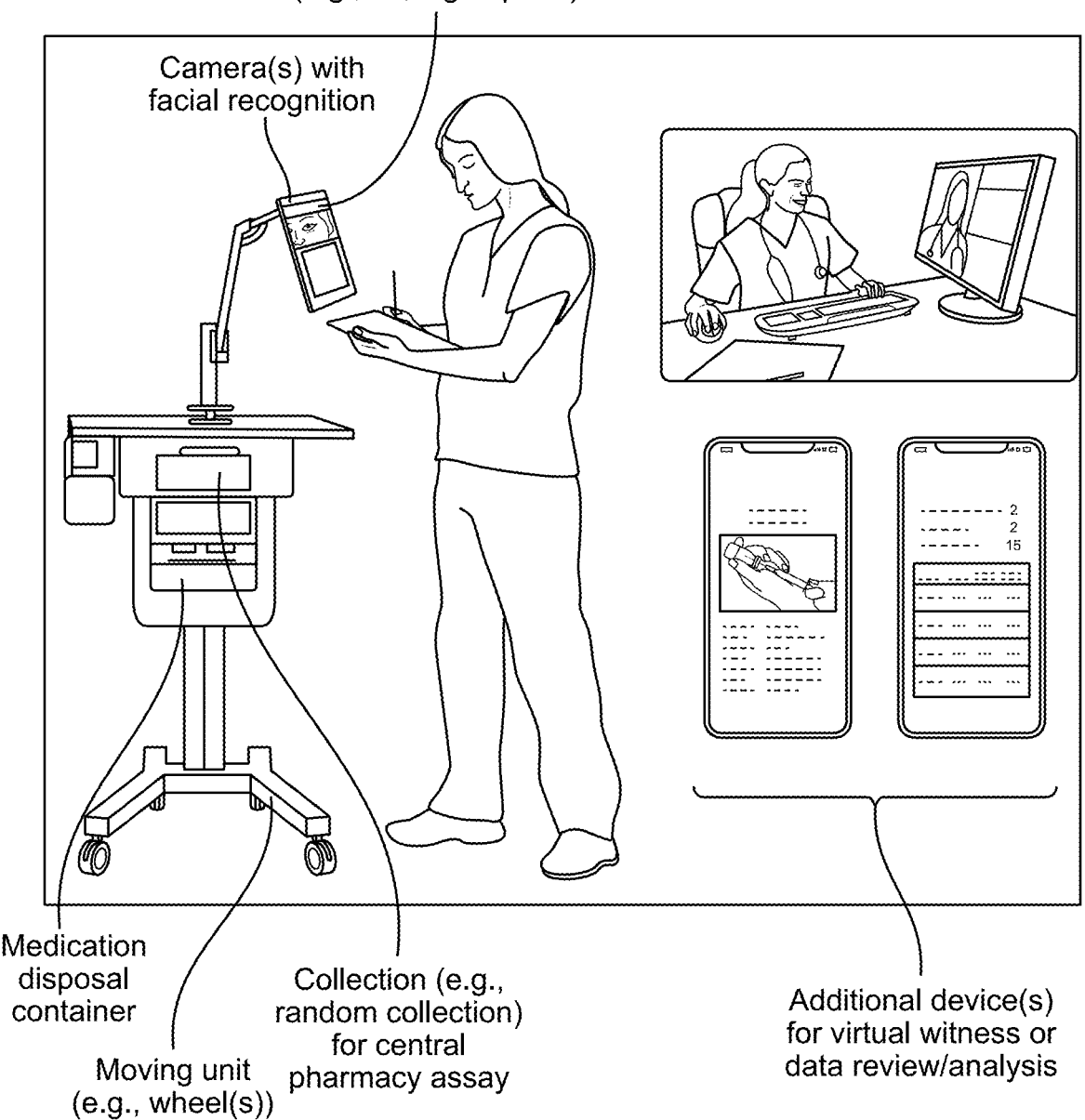
FIG. 14 schematically illustrates an example ecosystem for medication wasting, the ecosystem comprising a mobile medication wasting system and additional device(s) (e.g., user device(s)) for virtual witnessing or medication waste data review/analysis.
Figure 16:
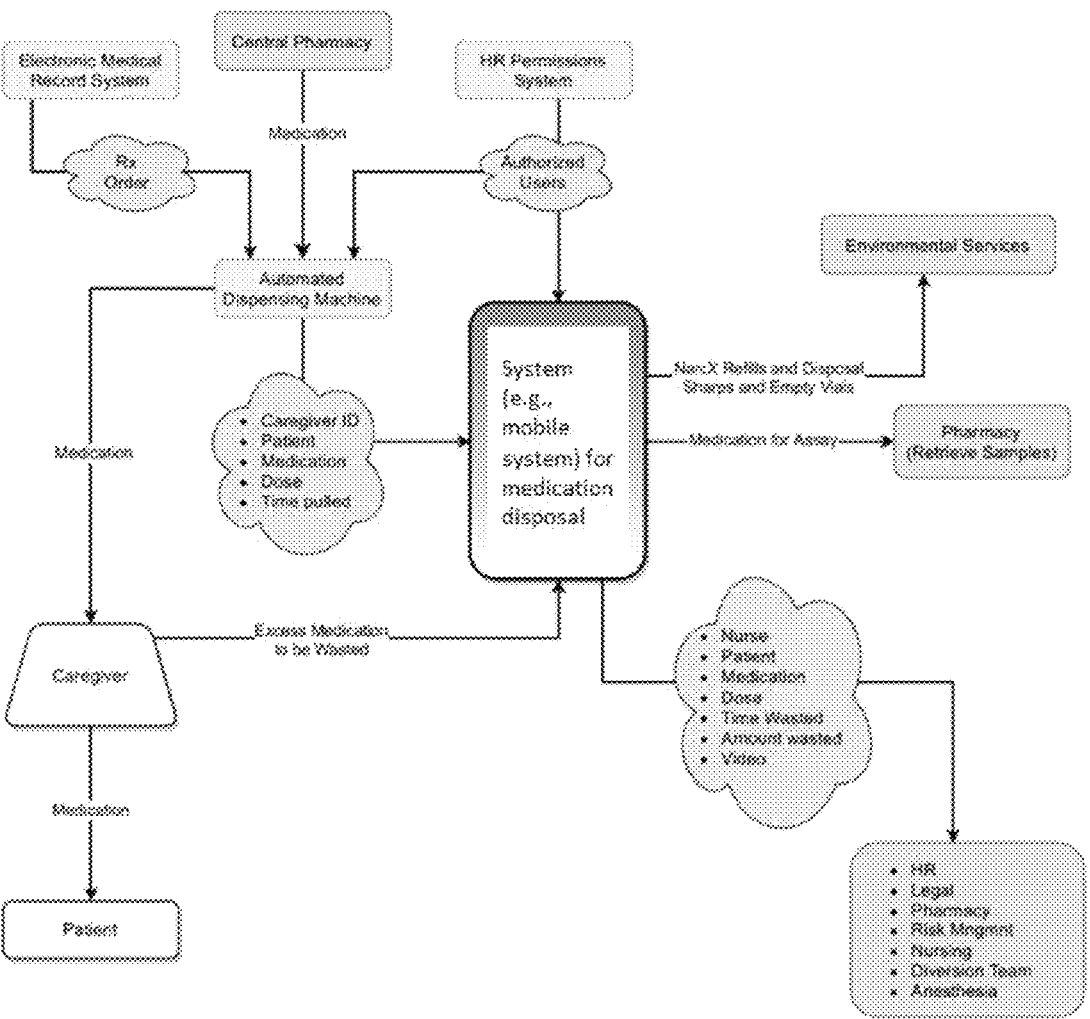
FIG. 16 schematically illustrates an example of a healthcare facility wasting workflow in conjunction with the systems and methods of the present disclosure.

In some embodiments, medication monitoring module as disclosed herein can be used to monitor disposing of expired medications. For medications originally provided (e.g., manufactured or prescribed) or used in a packaging (e.g., bottle, syringe, etc.), the medications can be disposed out of the packaging (e.g., pill or liquid medications can be poured out of the packaging and into a waste container) or disposed along with the packaging (e.g., the packaging containing the medications can be disposed into a waste container). In the example where the packaging containing the medications is disposed into the waste container, the systems and methods disclosed herein (e.g., the medication monitoring module) can be used to scan identifiers (e.g., machine readable codes, such as barcodes) of the packaging (e.g., by taking an image or video of the packaging). The action of reading the identifier and storing digital data thereof can be a prerequisite to disposing of wasting the medications into the waste container. FIG. 13 shows an example image of a plurality of medications packaging (e.g., bottles, syringes, etc.) that have been disposed into a medication waste container.

In some embodiments, the medications being disposed and monitored during such disposal by the systems and methods disclosed herein (e.g., the medication monitoring module) can be expired medications (e.g., an outdated removal process).

Figure 6A:
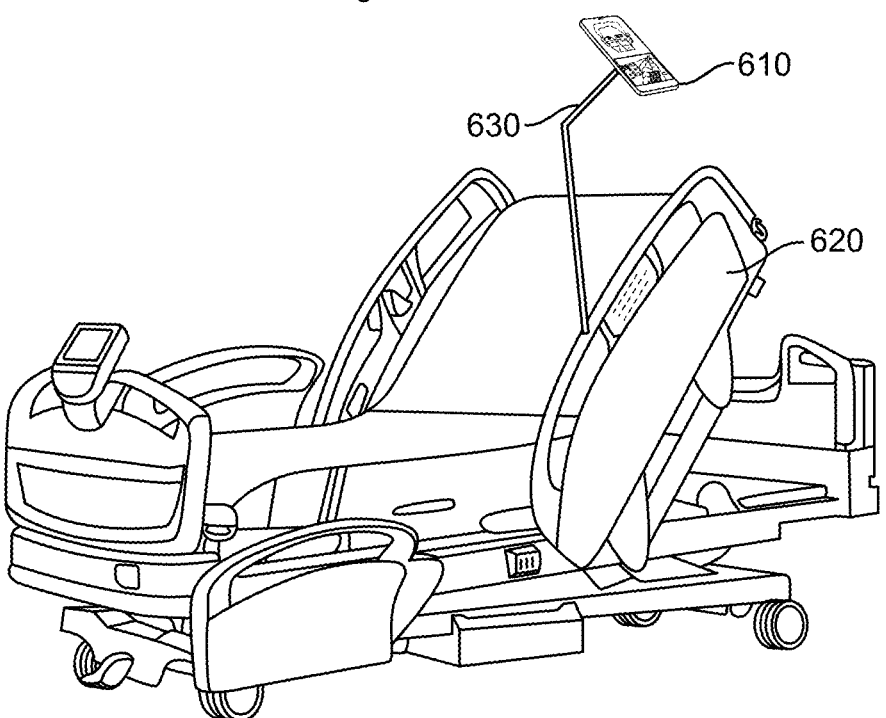
FIGS. 6A and 6B schematically illustrate exemplary different applications of a medication monitoring module.
Figure 6B:
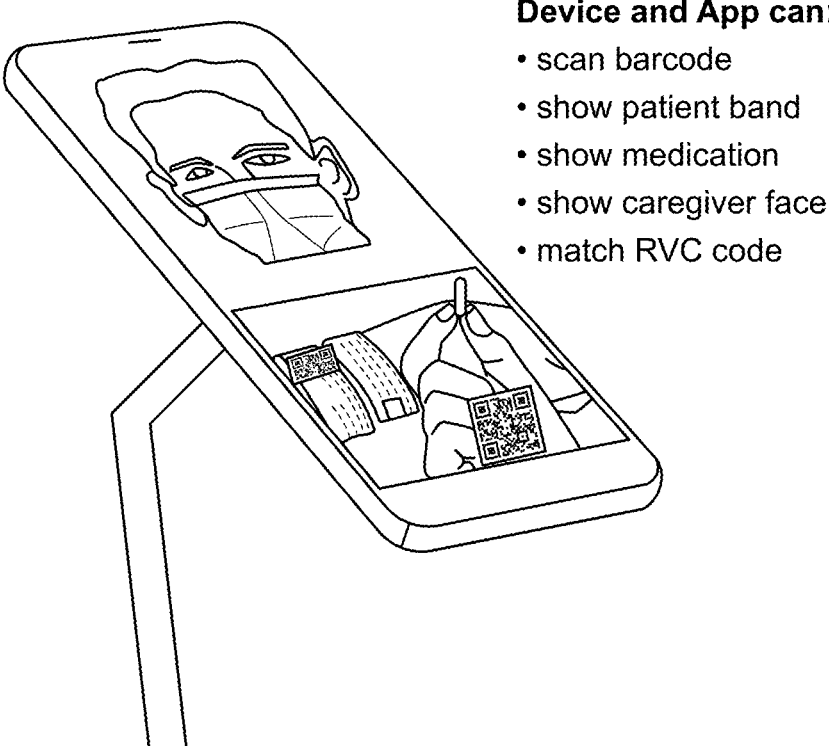

In some embodiments, the medication monitoring module as disclosed herein can be used to monitor dispensing or prescription of the medication by a healthcare provider (e.g., a nurse) to a patient. As illustrated in FIG. 6A, a user device 610 that is programmed with the medication monitoring module can be operatively coupled to a patient bed 620 via a bed mount coupling unit 630. For example, one end of the coupling unit 630 can be physically coupled to a bed rail of the patient bed 620, and the other end of the coupling unit 630 can hold the user device 610. As such, the medication monitoring module can direct the user device to monitor a user (e.g., a healthcare provider, such as a nurse), an identifier of the user, a patient in need of the medication, an identifier of the patient, dispensing of the medication by the user to the patient, and/or intaking of the medication (e.g., swallowing of a pill medication) by the patient. As illustrated in FIG. 6B, any images or videos taken by one or more sensors of the user device (as directed by the medication monitoring module) can be displayed on the user device in situ or subsequent to the monitoring. For example, a nurse can use the medication monitoring module of the user device (e.g., a mobile device distributed by the hospital) to scan a barcode of the nurse's ID for nurse identification/confirmation, scan a barcode of the patient's wrist band for patient identification/confirmation, scan the medication for medication identification/confirmation, scan a caregiver's identification or face for additional security measures and accountability. The identification can be a barcode or a RVC, as disclosed throughout the present disclosure.

C. Additional Aspects for Medication Monitoring

Users of the medication monitoring module can include healthcare providers as provided herein, and employees of the medical institutions, pharmaceutical companies, or pharmaceutical distributors that are responsible for managing medication inventory. For example, such employees may be responsible for re-stocking medications in one or more ADCs, collecting used sharps containers, collecting returned unused/leftover medications (e.g., emptying the collection bins for ultimate destruction of the medications), etc. In some examples, the users can comprise nurses or nurse practitioners. Unused medications can be disposed by using the medication monitoring module for various reasons, e.g., overprescription, refused by the patients, or accidentally dropped by the patients or healthcare providers. In some embodiments, users of the medication monitoring module can include pharmaceutical manufacturers, providers of raw materials and/or ingredients of medications, and the medication monitoring module and methods thereof can be utilized to monitor such users for proper handling and/or wasting of substances to eliminate diversion thereof. In some embodiments, users of the medication monitoring module can include subjects or patients that are taking the medications.

The medication monitoring module can be programmed in a user device that is positioned and used in one or more locations within a medical institution, such as, for example, medication rooms (i.e., med rooms), nursing stations, hospital ward hallways, patient rooms, and/or patient care centers (e.g., a surgery room, ambulatory surgical center (ASC), post anesthesia care unit (PACU) or recovery room, intensive care unit (ICU), intermediate ICU or step-down unit, interventional radiology suites, operating rooms, skilled nursing facilities, long term acute care facilities, etc.). Alternatively, the user device can be placed within an individual's home, such as bedroom, bathroom, living room, kitchen, etc.

In some cases, the user device programmed with the medication monitoring module can be positioned in a pharmacy, such as a retail pharmacy, an outpatient pharmacy (e.g., an outpatient clinic pharmacy), or a hospital pharmacy.

In some cases, the medication monitoring module and methods thereof as disclosed herein can be utilized to monitor (e.g., survey, scrutinize, etc.) healthcare providers during medication wasting processes across multiple systems in one or more different/disparate areas (e.g., within the same facility or in a different remote facility). A single user device programmed with the medication monitoring module can monitor multiple disposals of medications into multiple medication collection units. Alternatively, a plurality of user devices, each programmed with the medication monitoring module, can be in digital communication with each other to monitor multiple disposals of medications into multiple medication collection units.

The medication monitoring module can be configured to identify healthcare providers via their identifier (e.g., a key or an employment identification (ID) badge) and/or biometrics (e.g., facial recognition) for identification and/or verification, tracking, confirmation, and/or supervision of medication management/wasting by the healthcare providers. The medication monitoring module can be utilized as a "virtual" witness to supplement and/or replace the need of a third-party witness during, for example, (i) dosing or portioning of prescribed medications, and/or (ii) wasting of any unused or leftover medications.

The medication monitoring module, as provided herein, can comprise or be operatively coupled to a patient/medication tracking system, such as eMAR or CPOE, to retrieve and update patient data with respect to a patient's prescribed medications (e.g., types and doses of prescribed drugs). In some cases, the medication monitoring module can allow the user to update information (e.g., amount of unused or leftover medications being returned) to the patient/medication tracking system.

The medication monitoring module and methods provided herein can be implemented to monitor various types of medication management, such as medication retrieval, dosing, return, and/or wasting. The term "medication(s)" or drug(s)" as used interchangeably herein generally refers to any forms of medications, e.g., tablets, capsules, pills, powders, granules, dragees, gels, slurries, ointments, solutions suppositories, injections, inhalants, aerosols, coverings (e.g. transdermal delivery systems, such as transdermal patches), other forms of medications, modifications thereof, or combinations thereof. Medications can be controlled or non-controlled. The term "pill medication," as used herein, can generally refer to any form of oral medication. As such, the terms "pills," "powders," "granules," "dragees," "gels," etc. can be used interchangeably herein to refer to an oral medication.

The medications, as provided herein, may or may not require prescription (e.g., by healthcare professionals, such as physicians). In some examples, prescriptions are not needed for over-the-counter medications, such as, for example, Robitussin, Tylenol, and Sudafed. The medications, as provided here, may or may not be controlled. Examples of non-controlled prescription substances include antibiotics, cholesterol medication, and Viagra.

Examples of controlled substances can comprise opiate and opioids, as well as central nervous system (CNS) depressants and stimulants. Examples of opioids can include morphine, codeine, thebaine, oripavine, morphine dipropionate, morphine dinicotinate, dihydrocodeine, buprenorphine, etorphine, hydrocodone, hydromorphone, oxycodone, oxymorphone, fentanyl, alpha-methylfentantyl, alfentanil, trefantinil, brifentanil, remifentanil, octfentanil, sufentanil, carfentanyl, meperidine, prodine, promedol, propoxyphene, dextropropoxyphene, methadone, diphenoxylate, dezocine, pentazocine, phenazocine, butorphanol, nalbuphine, levorphanol, levomethorphan, tramadol, tapentadol, anileridine, any functional variant thereof, or any functional combinations thereof. Examples of CNS depressants and stimulants can include methylphenobarbital, pentobarbital, diazepam, clonazepam, chlordiazepoxide, alprazolam, triazolam, estazolam, any functional variant thereof, or any functional combinations thereof.

Additional examples of the medications and the relevant therapeutic applications include scopolamine for motion sickness, nitroglycerin for angina, clonidine for hypertension, and estradiol for female hormone replacement therapy. Other examples of the drugs include, but are not limited to, methylphenidate, selegiline, rivastigmine, rotigotine, granisteron, buprenorphine, estradiol, fentanyl, nicotine, testosterone, propofol, etc.

In some embodiments, the medication collection unit can be configured to receive a plurality of forms (e.g., pills, liquids, patches, etc.) of medications for wasting. In some embodiments, the medication collection unit can be configured to receive only a single form of medications for wasting. In some embodiments, the medication collection unit can be configured to receive only a single specific type of medication (e.g., only propofol emulsions, only fentanyl liquids, etc.) for wasting.

In some embodiments, the medication monitoring module or an analysis module (i.e., a medication analysis module) operatively coupled thereto can be configured to utilize data generated during monitoring of the medications (e.g., images or videos of the medications obtained by the user device, as directed by the medication monitoring module) to estimate properties of the medications (e.g., brand, color, size, shape, weight, density, and/or chemical content). In some embodiments, the medication monitoring module or the analysis module may comprise one or more sensors for measuring or estimating properties of the medications. In some embodiments, the one or more sensors may comprise a scale for measuring weight. In some embodiments, the one or more sensors may comprise a vision sensor for counting number of pills or tablets. Based on one or more estimated properties, the medication monitoring module or the analysis module can determine a probability or likelihood that the medication wasted is what was reported by a user (e.g., a nurse or the user of the medications) who wasted the medication. The medication monitoring module or the analysis module can determine that the probability that the medication wasted matches what is reported by the user is at least about 10%, 15%, 20%, 25%, 30%, 35%, 40%, 45%, 50%, 55%, 60%, 65%, 70%, 75%, 80%, 85%, 90%, 95%, 99%, or more. The medication monitoring module or the analysis module can determine that the probability that the medication wasted matches what is reported by the user is at most about 100%, 95%, 90%, 85%, 80%, 75%, 70%, 65%, 60%, 55%, 50%, 45%, 40%, 35%, 30%, 25%, 20%, 15%, 10%, or less.

Based on one or more estimated properties of the medications, the medication monitoring module or the analysis module can determine a probability or likelihood that an amount (e.g., a number of pills, a number of patches, a volume of liquid medications, etc.) of the medication wasted matches what is reported by the user. The medication monitoring module or the analysis module can determine that the probability that the amount of the medication wasted matches what is reported by the user is at least about 10%, 15%, 20%, 25%, 30%, 35%, 40%, 45%, 50%, 55%, 60%, 65%, 70%, 75%, 80%, 85%, 90%, 95%, 99%, or more. The medication monitoring module or the analysis module can determine that the probability that the amount of the medication wasted matches what is reported by the user is at most about 100%, 95%, 90%, 85%, 80%, 75%, 70%, 65%, 60%, 55%, 50%, 45%, 40%, 35%, 30%, 25%, 20%, 15%, 10%, or less.

Based on one or more estimated properties of the medications, the medication monitoring module or the analysis module can determine a probability or likelihood that an amount (e.g., a number of pills, a number of patches, a volume of liquid medications, etc.) of the medication wasted matches an amount that is supposed to be returned by the user. The medication monitoring module or the analysis module can determine that the probability that the amount of the medication wasted matches the amount that is supposed to be returned by the user is at least about 10%, 15%, 20%, 25%, 30%, 35%, 40%, 45%, 50%, 55%, 60%, 65%, 70%, 75%, 80%, 85%, 90%, 95%, 99%, or more. The medication monitoring module or the analysis module can determine that the probability that the amount of the medication wasted matches the amount that is supposed to be returned by the user is at most about 100%, 95%, 90%, 85%, 80%, 75%, 70%, 65%, 60%, 55%, 50%, 45%, 40%, 35%, 30%, 25%, 20%, 15%, 10%, or less.

Based on one or more estimated properties of the medications, the medication monitoring module or the analysis module can determine a probability or likelihood that the user has mismanaged (e.g., lost or diverted) the medication. The medication monitoring module or the analysis module can determine that the probability that the user has mismanaged the medication is at least about 10%, 15%, 20%, 25%, 30%, 35%, 40%, 45%, 50%, 55%, 60%, 65%, 70%, 75%, 80%, 85%, 90%, 95%, 99%, or more. The medication monitoring module or the analysis module can determine that the probability that the user has mismanaged the medication is at most about 100%, 95%, 90%, 85%, 80%, 75%, 70%, 65%, 60%, 55%, 50%, 45%, 40%, 35%, 30%, 25%, 20%, 15%, 10%, or less.

For any probability or likelihood, as described herein, the medication monitoring module or the analysis module can be configured to alert one or more personnel when the determined probability/likelihood is above a predetermined threshold. Alternatively, the medication monitoring module or the analysis module can be configured to alert the one or more personnel when the user has previously been flagged for medication mismanagement for a predetermined number of previous incidences. Examples of the personnel can include the user, a supervisor of the user, and/or an administrator of the medical facility. The predetermined threshold for the probability/likelihood can be at least about 50%, 55%, 60%, 65%, 70%, 75%, 80%, 85%, 90%, 95%, 99%, or more. The predetermined threshold for the probability/likelihood can be at most about 100%, 95%, 90%, 85%, 80%, 75%, 70%, 65%, 60%, 55%, 50%, or less. The predetermined number of previous incidences can be at least 1 time, 2 times, 3 times, 4 times, 5 times, 6 times, 7 times, 8 times, 9 times, 10 times, or more. The predetermined number of previous incidences can be at most 10 times, 9 times, 8 times, 7 times, 6 times, 5 times, 4 times, 3 times, 2 times, or 1 time.

The medication monitoring module or the analysis module can report any probability or likelihood, as described herein, as a score based on, for example, an alphabetical range (e.g., A through E), a numerical range (e.g., 1 through 10, 0% to 100%, etc.), a color range (e.g., green to red), symbols (e.g., thumbs up and thumbs down), etc.

The medication monitoring module or the analysis module, as disclosed herein, can comprise or utilize a block chain (or "blockchain") database. The term "blockchain," as used herein, can refer to a suite of distributed ledger technologies that can be programmed to record and track anything of value (e.g., financial transactions, land titles, medical records, etc.). The blockchain can be a peer-to-peer (P2P) decentralized open ledger (or computer architecture thereof) that relies on a distributed network shared among its users. Each of the users can hold a public ledger of every transaction carried out using the architecture, and each public ledger can be checked against one another to ensure accuracy and accountability. Thus, a blockchain-based database (or blockchain database) can be used in place of a physical, centralized database, to record and handle one or more transactions of digital objects (e.g., data). Maintenance of the blockchain can be performed by a P2P network of communicating nodes (or computer systems) that are running a software. The software can be programmed with a specific application (e.g., cryptocurrency software, financial services software, supply chain software, smart contracts software, etc.). Transactions such as "party X transfers an object (e.g., a digital object, such as, for example, crypto-currency, prescriptions, etc.) Y to party Z" can be broad-casted to the P2P network (e.g., by using one or more software applications). The network nodes can validate the transactions, add them to their copy of the ledger, and then broadcast these ledger additions to other nodes. Thus, the blockchain can be a distributed database, wherein, in order to independently verify the chain of ownership or validity of any and every transferred object, each network node stores its own copy of the blockchain. In some cases, a new group of transactions (i.e., a block) is created (e.g., at a predeter-mined frequency, such as, for example, 6 times per hour), added to the blockchain, and quickly published to all nodes in the P2P network. Thus, each block can contain a crypto-graphic hash of the previous block to keep the previous block "accountable."

Tampering with transactions on the blockchain can become exponentially harder as time progresses, and can require extreme quantities of computing power to attempt, let alone succeed. In some cases, data stored in the block-chain can be included in integrity checks, in which trans-actions are assembled into a transaction merkle tree and hashed to produce a block header. Any alterations to trans-actions in a blockchain database can become apparent as the block would be invalid when indexed. As such, the block-chain's consensus mechanism can allow a data's hash to be published to the blockchain as irrefutable proof that the data existed at a given time in the past. Both the timestamp and the hash may be unalterable.

The blockchain database that is operatively coupled to the medication monitoring module or the analysis module can store data (e.g., scanned identification of the healthcare providers, patients, wasted medications, returned medica-tions, etc.) collected by the medication monitoring module and/or analysis data generated by the medication monitoring module or the analysis module (e.g., indication or chance of medication mismanagement by an individual user or insti-tution). The blockchain database, as provided herein, can be an alterable and secured P2P network among patients, prescribers, pharmacy, government agencies (e.g., FDA, DEA, etc.) to record and transfer data (e.g., medical history, prescription history, medication utilization and/or compli-ance analysis of a patient, date of prescription, date or return of unused medications, etc.). In comparison to a conven-tional, centralized database, the blockchain database can provide one or more advantages including, for example, transparency, safety, auditability, resistant to tampering, and accountability for (1) users of the medication monitoring module, (2) physicians, (3) pharmacies, (4) government agencies, (5) registered reverse distributors for destruction of unused medications, (6) and/or pharmaceutical compa-nies that provide the medications to the market.

In some embodiments, examples and details of medica-tion monitoring and tracking are provided in, for example, International Patent Application No. PCT/US2020/026434, which is entirely incorporated herein by reference.

D. Methods and Systems for Medication Management Monitoring

The methods and systems as provided herein, e.g., meth-ods and systems for medication monitoring as above men-tioned, can be usable for monitoring one or more aspects of medication management, for example, transport of medica-tions, inventory of medications, stocking or storage of medications (e.g., into correct inventory locations, bins, shelves, containers, bottles, pyxis pockets, drawers, etc.), retrieval and dispensing of medications (e.g., from ADM). The methods and systems provided herein can be applied or used in numerous aspects of a medication's chain of custody. For example, the medication monitoring module can be used to monitor or track manufacturing, distribution, storage, dispensing from a central storage to a satellite storage (e.g., a warehouse, storage container, shelves, drawers, bottles, other vessels, automated dispensing machines, patient administration, waste, returns, etc.), inventory within a hospital, dispensing by the hospital to a patient, etc. For example, the medication monitoring module can be used to monitor or track a nurse while the nurse is opening and/or closing one or more drawers or pockets of an ADM to stock medications into the ADM or dispense medications from the ADM.

FIG. 12 illustrates example drawers of an ADM, wherein each drawer (top or bottom schematics) has a plurality of pockets. Each pocket can be a designated spot for a particu-lar type and/or dosage of a medication.

In some cases, the medication monitoring module as disclosed herein can be used to monitor various aspects of medication management prior to (i) use of the medications by a user (e.g., a patient) and/or (ii) wasting of any leftover or unused portion of such medications.

In some cases, the medication monitoring module can be used to monitor (e.g., record, analyze, etc.) handling (e.g., inventory, counting, dispensing, etc.) of medications, e.g., in and/or out of shelving units, in and/or out of medication dispensing systems (e.g., ADM), etc. In some examples, the medication monitoring module, while in operation with a user device, can be used to monitor (e.g., record) type and/or amount of medications that are being stocked and/or dis-pensed out of an ADM, e.g., by the nurse. Any data generated by the medication monitoring module during the monitoring (e.g., images, videos, etc.) by, e.g., a nurse or a pharmacist, can be analyzed simultaneously or subsequently to (i) confirm proper handling of the medications by the nurse or (ii) identify any discrepancy. For example, a dis-crepancy can be a difference between an amount of medi-cations that is supposed to be restocked into the ADM and an amount that is monitored to be added to the ADM. In another example, a discrepancy can be a difference between an amount of medications that is prescribed to a patient and an amount of medications that is dispensed by the nurse from the ADM for such prescription. In some examples, a discrepancy can be a different between (i) an expected amount of medications in a pocket within an ADM and (ii) an actual amount of the medications found in the pocket. For example, the expected amount of medications can be ascer-tained based on a previous user's use of the medication monitoring module and the ADM, while the actual amount of the medications can be ascertained based on a current user's current use of the medication monitoring module and the ADM. In some examples, a discrepancy can be ascer-tained based on what was previously dispensed by a nurse and/or replenished by a pharmacist. In some examples, a discrepancy can be ascertained based on what was invento-ried to the ADM previously by a nurse or a pharmacist on his/her previous access to the particular ADM pocket.

In some cases, the medication monitoring module dis-closed herein can display a message to the user (e.g., via a display unit and/or an audio unit of the user device), and the message can comprise various information, such as, for example, alerts about return information or health/safety recalls of the medications. For example, a medication that is being dispensed by the nurse (and is being monitored by the medication monitoring module) can be on a recall list. The medication monitoring module can identify the medication, determine that the medication is supposed to have been recalled but has not been pulled out from the ADM, and alert the nurse to prevent prescribing the recalled medication to a patient. As such, the medication monitoring module can complement the use of ADM to reduce any harm to patients.

In some cases, one or more medication units (e.g., inventory locations, bins, shelves, containers, bottles, pyxis pockets, drawers, etc.), can comprise an identifier as disclosed herein (e.g., RVC), such that the identifier can be scanned by the medication monitoring module (e.g., via the user device's camera) to link the user to each medication unit comprising the identifier. For example, each container unit (or pocket) within the ADM can comprise its own identifier (e.g., RVC) that can be scanned to link the user to each container unit during medication inventory or dispensing. When the user is confirming inventory of medications within the ADM or within one or more container units with the ADM, the RVC of the container unit can be scanned to track/monitor performance of the user.

In some cases, from a patient safety perspective, the medication monitoring module and methods thereof, as disclosed herein, can be used to intercept the impending dispensing or administration of a wrong drug (i) onto a shelf at a pharmacy, (ii) into an ADM, or (iii) to a patient.

Systems and methods as disclosed herein (e.g., the monitor module and methods thereof) can satisfy unmet needs in managing or curing various vulnerabilities in handling of medications, e.g., vulnerabilities for drug diversion in the inventory/dispensing of the medications, data entry during the medication handling, and/or other verification tasks in hospital pharmacy practices during the chain of custody of the medications.

In some cases, medications (e.g., controlled substances, non-controlled substances, any drugs of interest, expensive drugs, etc.) can be procured for the pharmacy, and the medication monitoring module and methods thereof can be utilized for reconciliation of the ordered items and the purchase order. For example, the medication monitoring module and methods thereof can be utilized to monitor and identify when an invoice is not signed and dated by the technician or clerk responsible for receiving the delivered medications, to promote/maintain traceability of medications transactions and correct documentation.

In some cases, medications can be retrieved from vendor or distributor deliveries. There can be a discrepancy between the medications and the packing slip invoice, and such discrepancy may not be identified (e.g., during a second confirmatory check), and tracing the origin (e.g., person, drug, time, location) of the discrepancy to correct it or prevent it from happening again may be difficult. As such, medication monitoring module and methods thereof can be used throughout various aspects along the chain of custody of the medications to, e.g., retroactively track and identify origin(s) of such discrepancies.

In some cases, a signed and dated packing slip or invoice may not be copied by the technician (or pharmacist) who is responsible for receiving the medications and putting them into an appropriate place (e.g., controlled substance safe/vault, ADM, etc.). Thus, the technician may not be able to file the packing slip/invoice for future review, thereby preventing accurate documentation. As such, medication monitoring module and methods thereof can be used to monitor (e.g., constantly monitor) the technician, such that image and/or videos of the packing slip/invoice can be recorded (e.g., automatically recorded) for review in the future.

In some cases, when medications are put into a designated place (e.g., a controlled substance vault or safe), the amount of medication (e.g., the number of units of medication) being deposited into the designated place can be entered into the system improperly, thus creating a discrepancy that may not be unnoticed until another person checks the inventory in the future. For example, the discrepancy may be when an amount of medications entered into the system matches a number of expected medications on the packing slip/invoice, but does not match an actual amount of medications being deposited. As such, medication monitoring module and methods thereof can be used to monitor medication handling and any documents thereof and analyze (e.g., automatically or retroactively analyze) any potential discrepancies.

In some cases, when medications are distributed from central pharmacy (e.g., out of the controlled substance vault/safe) and distributed to an ADS (e.g., on a medical floor, operating room, etc.), an order for the medications may not be verified (e.g., verified as a legitimate order), thus creating an opportunity for (i) an individual to obtain medications for purported uses or (ii) a patient to allow such individual to divert the medications (e.g., for orders made in the medication management software, called in by phone, or place via Fax). As such, the medication monitoring module and methods thereof can be used to track and regulate any transfer of medications.

In some cases, a technician or a pharmacist may indicate that a medications order is discontinued for a patient whose order should not be discontinued, thus creating a situation where the medications could be retrieved and diverted, e.g., after being delivered to an ADC. Thus, monitoring of the technician or the pharmacist by the medication monitoring module and methods thereof can be utilized to track performances of the technician or the pharmacist.

In some cases, a second technician or a pharmacist may fail to verify the retrieved medications against the printed receipt listing the medications to be retrieved (e.g., from a controlled substance vault/safe), thereby allowing for an unnoticed discrepancy. Thus, monitoring of the second technician by the medication monitoring module and methods thereof can be utilized to track performances of the second technician.

In some cases, a second independent check by a technician (or a pharmacist) to verify the retrieved medications may not occur, thereby allowing a discrepancy to go unnoticed and creating an opportunity for an incorrect medication to be delivered (e.g., to patients). Thus, monitoring of the second technician by the medication monitoring module and methods thereof can be utilized to identify such discrepancy.

In some cases, medications may not be observed and may not be accessible for tampering or diversion once the medications are retrieved (e.g., from controlled substance vault/safe) and are to be delivered to hospital floors in carts, lock boxes, or other transportation means. Thus, monitoring by the medication monitoring module and methods thereof can monitor transfer/handling of the medications in such "black spots."

In some cases, as to delivery of medications (e.g., to a hospital floors or operating rooms), a subject or a witness may not verify that the medications added to an ADS is the same as the name of the medication listed on the screen of the ADS, thereby permitting an incorrect medication to be placed into the wrong sub-container within the ADS and creating an opportunity to (i) divert medications and/or (ii) prescribe incorrect medications to patients. In different cases, as to delivery of medications (e.g., to a hospital floors or operating rooms), a subject or a witness may not verify that the amount of medications added to an ADS matches that shown on the screen of the ADS. Thus, monitoring by the medication monitoring module and methods thereof can confirm proper storage, dispensing, and/or prescription of medications, to prevent or reduce serious patient safety issues. Similarly, a witness may not verify an amount (e.g., a count) of unit doses already in the ADS before additional doses are added, thereby creating an opportunity for a discrepancy, and the medication monitoring module and methods thereof can be utilized to identify or prevent such occurrences.

In some cases, an incorrect expiration date may be entered into an ADS, thereby causing a delay in retrieving expired or soon-to-be-expiring medications (e.g., when an input date is later than a correct expiration date) or enabling an individual to retrieve medications before their expiration date for diversion (e.g., when the individual inputs an earlier date than the correct expiration date). As such, monitoring of the second technician by the medication monitoring module and methods thereof can be utilized to monitor data entry (e.g., entry of the expiration dates) into the ADS along with the actual medication containers or packages, to confirm that the expiration date provided to the ADM matches the actual expiration date of the medications.

In some cases, a technician may not return discontinued medications (e.g., medications which have been previously ordered for a patient, but which order has not been cancelled due to the patient's clinical condition or change in therapy) to a collection site (e.g., a central pharmacy), thereby allowing a chance for drug diversion. Thus, as such, monitoring of the second technician by the medication monitoring module and methods thereof can be utilized to monitor the technician and discourage the technician from not returning discontinued medications. Alternatively or in addition to, such monitoring can identify medications that are no longer being utilized in the ADM and make a recommendation to unload them to be moved back to a collection site, e.g., a central pharmacy.

Figure 11:
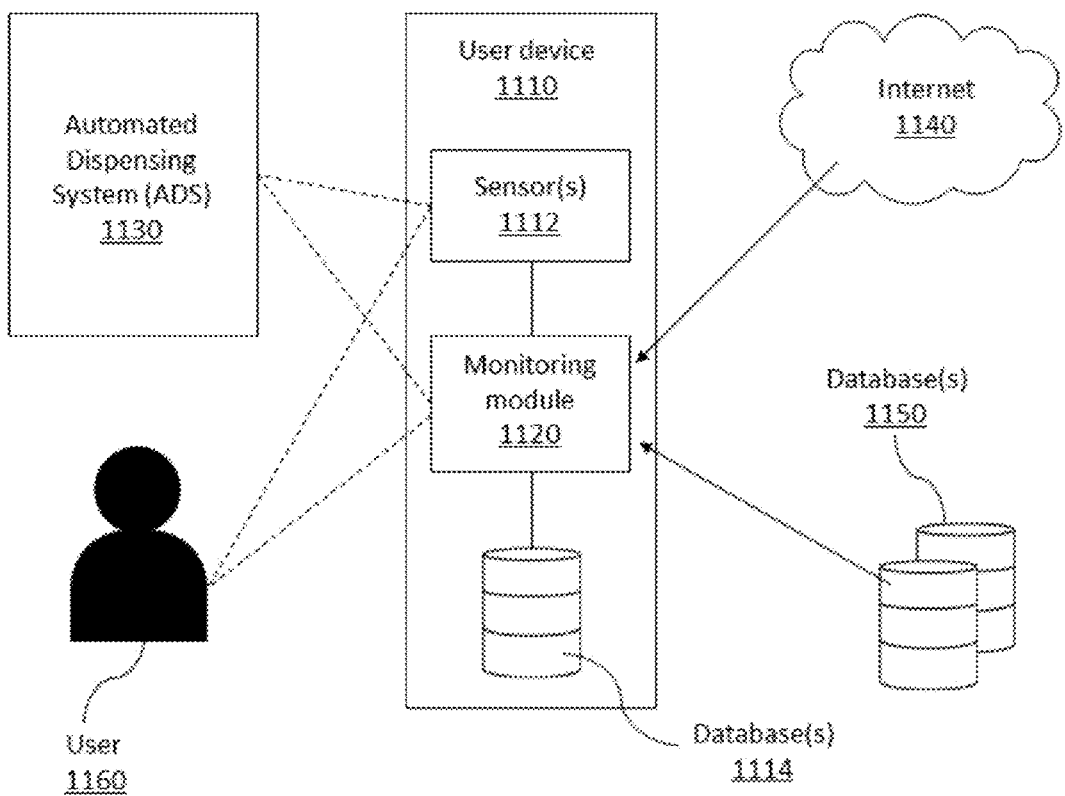
FIG. 11 schematically illustrates an exemplary ecosystem comprising a medication monitoring module for monitoring use of an automated dispensing system.

FIG. 11 schematically illustrates an exemplary ecosystem comprising a medication monitoring module. The medication monitoring module can be configured to perform any of the applications disclosed herein. The ecosystem can comprise a user device 1110, such as, for example, a mobile phone of a healthcare provider (e.g., a hospital system, a nurse, etc.). The user device 1110 can comprise one or more sensors 1112, such as, for example, one or more cameras. In some cases, the user device 1110 can comprise (i) a first camera 1112-*a* disposed on a first surface of the user device 1110 (e.g., a "front" facing camera) and (ii) a second camera 1112-*b* disposed on a second and different surface of the user device 1110 (e.g., a "back" facing camera), such that the first camera 1112-*a* can capture one or more images/videos of the user 1160 (e.g., the user's face) and the second camera 1112-*b* can capture one or more images/videos of the medication and/or the ADS 1130 prior to, during, or subsequent to inventory of the medications into the ADS 1130 or dispensing of the medications out of the ADS 1130. In an example, the first camera 1112-*a* can record a face of the user 1160 while (or at the same time) the second camera 1112-*b* can capture the user's hand, the medication, and the ADS 1130. A medication monitoring module 1120 can be installed as a software (e.g., a mobile application) on the user device, and the medication monitoring module 1120 can be granted access to control the sensor(s) 1112 of the user device 1110, the database(s) 1114 of the user device 1110, or both. In some cases, the medication monitoring module 1120 can be operatively coupled to the internet 1140 to retrieve information about the user 1160, the user device 1110, the ADS 1130, the medication, prescription of the medication, original packaging of the medication, etc. In some cases, the medication monitoring module 1120 can be operatively coupled to one or more centralized database(s) 1150, as disclosed herein, to transmit digital data to or from the database(s) 1150.

E. Medication Management or Wasting in Pharmacies

In some aspects, the methods and systems as disclosed herein for monitoring medications can be used for pharmacies (e.g., pharmacy stores, hospitals, surgical rooms, doctor's offices, ambulances, etc.) to manage (e.g., receiving from a vendor, stocking, selling, distributing, returning, wasting, etc.) medications. In some aspects, the methods and systems disclosed herein for monitoring medications can be used in various locations where medication may be stored (jails, prisons, police precincts, police evidence rooms/crime labs, airports, online shopping warehouses, etc.). The methods and systems can allow a user (e.g., a pharmacist, physician, nurse, distributor, etc.) to utilize a device (e.g., any user device) to track/monitor such management of medications.

Pharmacies may need to discard expired, recalled, and/or unused medications. For example, pharmacies may need to return expired, recalled, and/or unused medications to a receiver (e.g., pharmaceutical manufacturers, reverse distributors, etc.). In absence of the methods and systems disclosed herein, such return process by pharmacies may involve shipments of goods (e.g., medications) through reverse distributors and/or central warehouses for (i) verification of the returned goods and/or (ii) destruction (e.g., which can be costly), in order for pharmaceutical manufacturers to (1) verify destruction of their products and/or (2) issue credits (e.g., monetary, discounts, or other benefits) to their retail partners (e.g., the pharmacies). Thus, the methods and systems disclosed herein can be applied (or modified) to provide verifications (e.g., digital, visual verifications, etc.) of separation, return, and/or destruction of medications onsite (e.g., at the site where the medications are located, e.g., retail or other pharmacy establishments such as hospital pharmacy, mail order, retail, institutional, etc.). In some embodiments, the methods provided herein can allow pharmacies to return and/or waste medications without high costs (e.g., multi-million dollar expenses) of moving garbage (e.g., expired, recalled, and/or unused medications) for verification.

In some embodiments, destruction of the medications provided to (e.g., wasted into) the receptacle(s) as disclosed herein can be performed on site (e.g., where the device comprising the receptacle(s) is at) or at a separate destruction site. Destruction can be incinerating the medications, encapsulating the medications by a filler (e.g., foam, gel, etc.) to prevent access to the medications, adding neutralizers (e.g., chemical decontaminants, drug antagonists, mechanical encapsulant, etc.) to deactivate the wasted medications, etc. For example, the receptacle(s) can comprise one or more neutralizing agents to deactivate (or inactivate) any medication(s) received by the receptacle(s).

In some embodiments, the methods and systems as disclosed herein can utilize one or more collection receptacles (e.g., at least 1, 2, 3, 4, 5, 6, 7, 8, 9, 10 or more waste receptacles) for receiving one or more types of medications (e.g., at least 1, 2, 3, 4, 5, 6, 7, 8, 9, 10 or more different types of medications). In some cases, a plurality of collection receptacles can be utilized to receive a plurality of different types of medications, and a controller (e.g., a software processor) operatively coupled to the plurality of collection receptacles can be utilized to indicate (e.g., highlight) an appropriate or correct receptacle of the plurality of collection receptacles, such that medications are deposited into a correct receptacle. Non-limiting examples of different types of medications can include one or more members from medication dosage form (e.g., solid, liquid, gel, powder, patches, etc.), packaging (e.g., opened, closed, etc.), categories (e.g., hazardous waste, regular waste), expired and/or non-expired, recalled and/or non-recalled, medication brand, and/or instructions (e.g., to be destructed on-site, to be collected by reverse distributors, etc.).

In some embodiments, the systems as disclosed herein can comprise an indicator (e.g., an optical indicator that shows a user which receptacle to use when depositing/wasting medications, and the indicator can be directed based at least in part on classification of the medications. The classification can be user-defined (e.g., user-selected on a graphical user interface (GUI) that is operatively coupled to the receptacles) or automatic (e.g., by analyzing an image of the medications and/or the packaging thereof, scanning a machine readable code (MRC) disposed on the medications and/or the packaging thereof, etc.). The systems and methods disclosed herein can direct the user to ensure compliance to a means of wasting that is provided by a government agency (FDA, DEA, etc.), pharmaceutical companies, manufacturers, and/or the reverse distributor. The indicator can be a physical indicator, such as an optical indicator (e.g., a light emitting diode (LED)) that is disposed adjacent to or on each receptacle of the plurality of receptacles. Alternatively or in addition to, the indicator can be on the GUI that is operatively coupled to the plurality of receptacles. For example, the GUI can display one or more images/videos of at least the recommended receptacle, such that the user can identify (e.g., easily identify) the recommended receptacle for depositing the medications.

In some embodiments, the system of the present disclosure can comprise a plurality of receptacles (e.g., for receiving different types of medications) on a portion (e.g., a work surface) of the system. A waste receptacle (e.g., each waste receptacle) of the plurality of receptacles on the work surface can have a covering (e.g., a lid) with an identifier (e.g., a machine readable code (MRC), such as a Quick Response (QR) code). The system can further comprise a device (e.g., a user device, such as a mobile device or a tablet) with a sensor, such as a camera. Such device and the plurality of receptacles may be part of the same housing. Alternatively, the device and the plurality of receptacles may not be a part of the same housing, e.g., they may be movable with respect to each other. The sensor of the device (e.g., a camera of a tablet) can detect (e.g., visualize) the identifier of the waste receptacle for validation of the identifier, in order for the wasting process to continue. Such step can ensure that the medications are deposited into the correct receptacle.

An identifier as disclosed herein (e.g., an identifier of the waste receptacle, an identifier of a medication, an identifier of a medication container, etc.) can comprise a machine readable code (MRC). The MRC may be a barcode (e.g., a linear barcode, a matrix barcode, etc.). The identifier can comprise a reconstructable visual code (RVC). The RVC can be a dynamic visual code that is divided into a plurality of portions configured to be combined (e.g., upon activation) to form a functional visual code that is readable. The RVC can comprise a physical code (PHC) and/or an augmented reality code (ARC). Examples of the RVC and methods of use thereof are provided in, for example, International Patent Application No. PCT/US2020/019122, which is entirely incorporated herein by reference.

In some embodiments, the methods and systems as disclosed herein can allow the user to direct data (e.g., text, image, video, etc.) to be transferred a third party, such as supervisors, other pharmacies, pharmaceutical companies, medication manufacturers, distributors, reverse distributors, an individual or a company that is managing the device comprising the receptacle(s) as disclosed herein. Such device can comprise one or more physical buttons or one or more digital buttons (e.g., on GUI of a display of the device or of a user device operatively coupled to the device) to send such data to the third party. In some cases, the device can comprise a "call" button, which, when activated (e.g., selected by the user), sends (e.g., automatically sends) data to the third party, and the data can comprise an alert information about any anomaly (e.g., odor, malfunctioning, misuse, etc.) of the device that requires further attention. For example, wasted medications can react with one or more neutralizing agents and create an odor, and a user (e.g., same user who wasted the medications, or subsequent users) can report such odor.

In some embodiments, the methods and systems disclosed herein can record and generate a digital recording (e.g., a visual transactional receipt, such as one or more images and/or videos) of the user's actual medication wasting transaction. The digital recording can serve as a virtual witness of the user's wasting of medications into a receptacle of the system as disclosed herein. The digital recording can be stored, easily transferable, and duplicates can be generated (e.g., automatically) for records keeping, accountability, tracking, reverse tracking, etc. The digital recording can be more informative, more accurate, and/or complimentary to the user's attestation of information about the medications (e.g., waste data) provided via hand-written documents and/or the GUI as disclosed herein.

In some embodiments, the methods and systems disclosed herein can provide one or more benefits to a third party (e.g., pharmaceutical companies, medication manufacturers, etc.), such as (i) obtaining data for tracking the medications (e.g., visibility to product counts, such as vaccines), (ii) reduced storage space and/or fees (e.g., eliminated storages fees for storing recalled medications), (iii) reduced transportation costs (e.g., for not having to physically collect recalled medications), (iv) decommissioning ability (e.g. meeting one or more requirements of relevant statues, such as the Drug Supply Chain Security Act (DSCSA) of the Drug Quality and Security Act (DQSA)), (v) reduced chargebacks, (vi) easily and/or readily report medication recalls to pharmacies, (vii) obtaining data for errors in tracking wasted medications (e.g., errors automatically flagged by the systems as disclosed herein, such as a discrepancy between an amount of the medications detected by the device vs an amount of the medications entered by the user), (viii) loss prevention analysis tool(s), (ix) quantification of future returns (e.g., automatically calculated amount/number of medications that have not been wasted into the systems disclosed herein, collected amount/number of medications by the systems disclosed herein, etc.), and/or (x) a new platform to provide/transfer incentives and/or refunds to the pharmacies. In some cases, the methods and systems as disclosed herein can meet the need for a platform for pharmaceutical companies or medication manufacturers to issue credit (e.g., monetary credit) to the pharmacies, and/or improve the process of medication return by the pharmacies.

In some examples, the methods and systems disclosed herein can allow the third party (e.g., pharmaceutical companies, medication manufacturers, etc.) to obtain data (e.g., visual data) indicative of an amount (e.g., count) of medications at a particular pharmacy, e.g., (i) without a middleman, (ii) at a faster rate than having to physically visit and/or discuss with the particular pharmacy, and/or (ii) at a higher frequency with a lower cost.

In some examples, a pharmaceutical chargeback can occur when a wholesaler buys drugs from a pharmaceutical company according to a pharmaceutical contract price, then sells the drugs to consumers (e.g., pharmacies) according to a consumer contract price. When the consumer contract price is lower than the pharmaceutical contract price, the wholesaler can avoid losses by charging the pharmaceutical company for the difference, and such charging can be referred to as a pharmaceutical chargeback. Alternatively or in addition to, the pharmaceutical chargeback can be the result of a failed transaction, in which the entire payment must be returned to the consumer.

Figure 21:
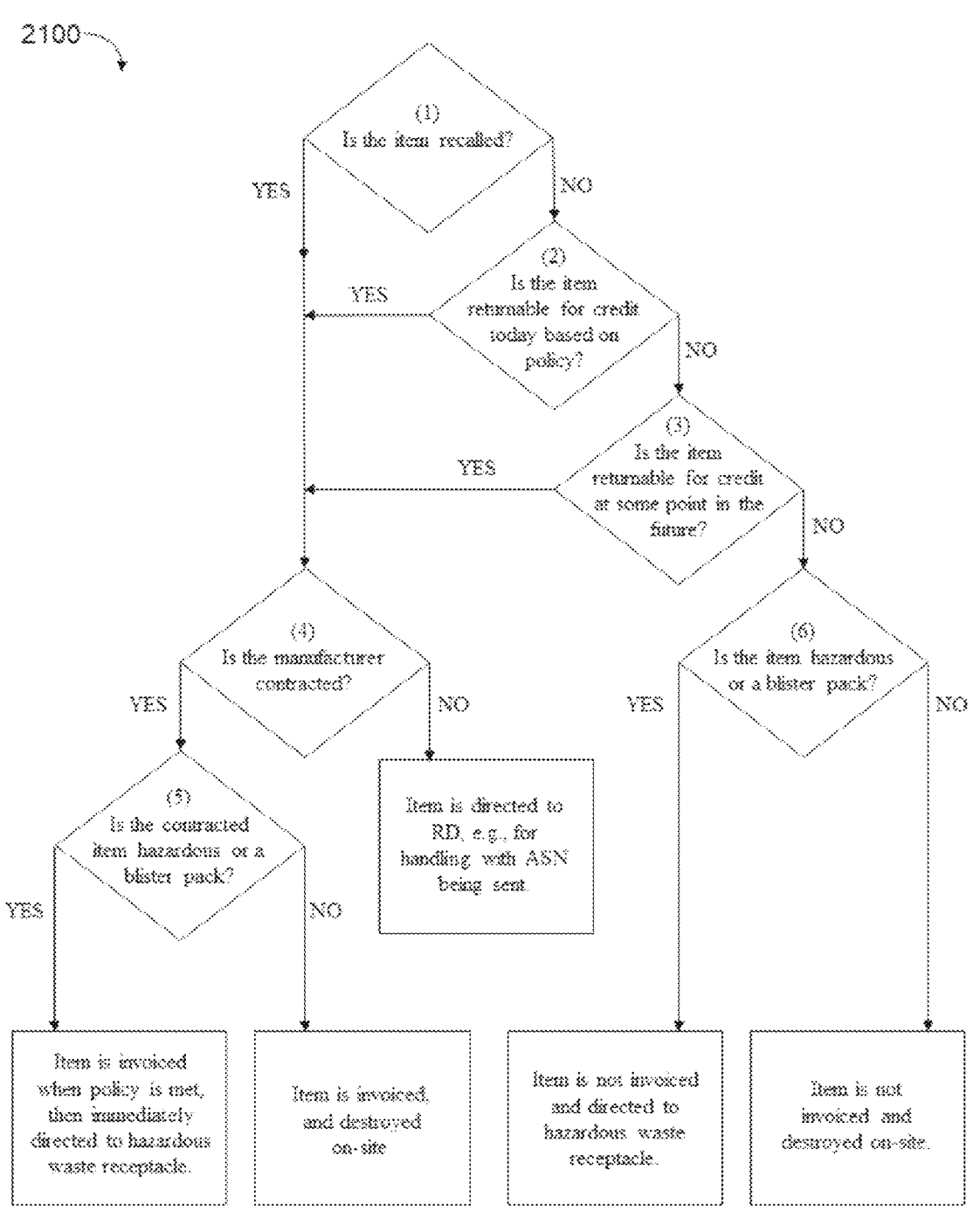
FIG. 21 shows an example flowchart for invoicing for a wasted and/or returned medications in accordance with the systems and methods of the present disclosure.

The methods and systems disclosed herein for monitoring medications (e.g., for a pharmacy to dispose medications, such as per the flowchart 2100 of FIG. 21) can utilize a GUI of a display (e.g., a display of a user device) to receive and/or send digital data to the user (e.g., a pharmacist). In some cases, the GUI of the methods and systems may be readily accessible without requiring a security data (e.g., log-in identification information and/or password). Alternatively, the GUI can require the user to provide such security data to utilize the GUI. For example, the user may need to "sign on" to access the GUI. Various information about the user, the user's site (e.g., the pharmacy's name, location, etc.), and/or drug (e.g., name, dosage, pharmaceutical company responsible for the drug, manufacturer of the drug, etc.) can be obtained via the user's use of the GUI. For example, such information can be automatically retrieved when the user logs into the GUI, e.g., from a database that is digitally and/or operatively coupled to the user. In another example, such information can be provided by the user via the GUI, e.g., after logging into the GUI. The user may log in to the GUI by providing a username and/or a password. Alternatively or in addition to, the user may log into the GUI by scanning a user identifier (e.g., identification card, badge, etc.). The log in requirement may impose a limitation or protection on managing the controlled substances. In some cases, a registered pharmacist (RPh) may be required to dispose, waste, or serve as witness to the disposal or waste of a controlled drug or substance.

In some cases, the information can include data about the pharmaceutical company responsible for the medication, such as (i) a return goods policy (RGP) for the medication (e.g., published or negotiated RGP), (ii) address, DEA number, and/or accounts payable (AP) number of a wholesaler, and/or (iii) address or AP number of the pharmaceutical company's corporate office. The information can include data about the site that the user is located in.

In some cases, the information can include data about the pharmacy, such as (address and/or DEA number of the pharmacy. Alternatively or in addition to, the information can include one or more rules (e.g., one or more established or pre-determined rules) for entry/disposal of medications. For example, the one or more rules can be for a quantity of medications that can be disposed in accordance with the methods and systems disclosed herein. In accordance with the rule, the pharmacy (or the retail site), may flag or not allow entry of full/sealed exceed an expected quantity of the medication. In some cases, methods and systems disclosed herein may detect errors often in quantity entry. For example, a manufacturer's bottle may have an expected full package size of 100, but an erroneous entry may be entered that exceeds 100. In some cases, detecting an error may trigger to an audit. In some cases, certain medications and/or packaging may be given exceptions when it the expected quantity of medication is uncertain (e.g., an amber vial). In accordance with the rule, a wholesaler (e.g., only a wholesaler) may be allowed to dispose medication case packs (e.g., blister packs).

In some cases, the information can include data about the location of the user, such as city and/or state where the user is located in. Alternatively or in addition to, the location may be the city and/or state information on the site of the user (e.g., pharmacy). State-specific or mandated hazardous waste regulations may be obtained. State-specific or mandated requirement for providing incentives (e.g., credits, such as monetary credits) for the disposed medications may be obtained. For example, certain states (e.g., Georgia, Mississippi, North Carolina, etc.) may mandate providing monetary credits to pharmacies for partial and/or whole returns.

The methods and systems as disclosed herein can allow a user (e.g., a user at a pharmacy, such as a pharmacist) to provide information (e.g., data entry) for medication management, e.g., dispose medications. The system can comprise a device (e.g., a user device) comprising a display, and the user can provide such data via the GUI presented on the display. Alternatively our in addition not, the system can comprise a sensor (e.g., a user's cell phone or tablet can comprise a camera) to scan an identifier of the user and/or of the medication (e.g., an identifier on the medications, or on a container of the medications) to retrieve information about the medications, as provided herein. For example, the user may scan each medication or each medication container, one at a time, to proceed with disposal of the medications (e.g., due to recall of the medications). Alternatively, the user can manually provide (e.g., type in) the identifier via the GUI. Non-limiting examples of the identifier of the medication as disclosed herein can include a barcode (e.g., a linear barcode, a two-dimensional (2D) barcode, a three-dimensional (3D) barcode, etc.), stock keeping unit (SKU), national drug code (NDC, e.g., 9 digits, 11 digits, etc.), and universal product code (UPC). The GUI may be operatively coupled to a centralized database as disclosed herein, to search for the obtained medication identifier to receive/extract relevant information about the medication.

In some cases, the user (e.g., the pharmacist) can use the sensor of the user device to scan a 2D barcode of the medications. Subsequently, the scanned 2D barcode can be used to populate information, such as dug rug name, strength, NDC, drug class, package size, image, lot number, expiration date, recall information, etc. The user can also provide information (e.g., digital data via the GUI) about quality, quantity, condition (e.g., whether the medication container has been opened, is closed, is sealed, etc.). For example, the GUI may provide a plurality of options for the user to select and/or provide input via the GUI: (i) full and sealed (e.g., allow entry of 1 only by the user), (ii) full and opened (e.g., allow the user to enter exact count of the medications), and/or (iii) partial (e.g., allow the user to enter exact count of the medications).

In some cases, the user (e.g., the pharmacist) can use the sensor of the user device to scan a UPC barcode of the medications. Subsequently, the scanned UPC barcode can be used to populate information about the medications, as disclosed herein. For example, the GUI may provide a plurality of options for the user to select and/or provide input via the GUI: (i) full and sealed (e.g., allow entry of 1 only by the user), (ii) full and opened (e.g., allow the user to enter exact count of the medications), (iii) partial (e.g., allow the user to enter exact count of the medications), (iv) enter expiration date (e.g., automatically populate most recently entered lot number for that expiration date; if none, leave blank), and/or (v) confirm lot number or allow the user to change or correct the lot number if different.

In some cases, the user (e.g., the pharmacist) can manually enter the NDC via the GUI, such that the system can retrieve additional information, e.g., population drug information from the centralized database. In an example, the user can enter an 11-digit NDC. In another example, the user can enter a portion of the NDC (e.g., first 9 digits of a longer NDC, first 5 digits of a longer NDC, etc.). Following, the system may provide one or more different NDCs that are each longer than 9 digits and different, and the user can select the correct and full NDC from the provided options. Alternatively or in addition to, the user can utilize the GUI to provide/record one or more conditions of the medications being managed (e.g., disposed). For medications in a manufacturer's medication container (e.g., pills in a bottle), the user can enter or confirm lot number, enter or confirm expiration date, and/or enter quantity of the medications (e.g., full/sealed, full/opened, and/or partial, as disclosed herein). For medications in a vial (e.g., an amber vial), the GUI can allow the user to enter the lot number, the expiration date (e.g., if not automatically retrieved from a database), and/or quantity of the medications as disclosed herein.

In some cases, the user (e.g., the pharmacist) can manually enter the medication's name or the name of the medication's company or manufacturer via the GUI, such that the system can retrieve additional information, e.g., population drug information from the centralized database. Alternatively or in addition to, the user can utilize the GUI to provide/record one or more conditions of the medications being managed (e.g., disposed), as disclosed throughout the present disclosure (e.g., same or different protocols for a manufacturer bottle and an amber vial).

For any of the information about the medications that can be provided by the user via the GUI of the system, as disclosed herein, the system can allow the user to omit provision of such information (e.g., when the user does not know the necessary information).

The system as disclosed herein can be capable of distinguishing between (i) unit of use and (ii) non-unit of use items, to prevent selection of partial and/or amber vial. The system can be capable of distinguishing between different types of medications (e.g., different forms of medications, different classes of medications such as controlled and non-controlled, different doses of medications, etc.).

Once items (e.g., medications to be disposed, returned, recalled, etc.) are scanned and registered as disclosed herein, the system can be configured to generate an invoice. For example, the invoice can be from a pharmacy to a third part, such as a contracted manufacturer or a pharmaceutical company, such that the pharmacy can be compensated for the disposed medications (e.g., expired medications, recalled medications, etc.). In some cases, when the disposed items (e.g., medications) are within a policy (e.g., a published policy by the contracted manufacturer or the pharmaceutical company), either immediately after induction (e.g., after disposal of the medication in accordance with the methods and systems disclosed herein) or at some point in the future thereof ((e.g., at least 1 day, 2 days, 3 days, 4 days, 5 days, 6 days, 7 days, 2 weeks, 3 weeks, 4 weeks, 2 months, 3 months, 4 months, 5 months, 6 months, 7 months, 8 months, 9 months, 10 months, 11 months, 12 months, or more), the disposed items can be listed on an invoice (e.g., debit memo, debit note) to initiate a payment process. Such payment process may be an example of an incentive provided to the user for managing the items (e.g., disposing the medications).

In some cases, disposed items (e.g., medications) from a single third party (e.g., a contracted manufacturer or a pharmaceutical company) can be grouped into a single invoice or a plurality of invoices (e.g., at least 1, 2, 3, 4, 5, 6, 7, 8, 9, 10, or more invoices). For each invoice, the third party can determine the type of information to be included in the invoice. For example, non-limiting examples of the information to be added to the invoice for medication management and wasting can include medication name, medication dosage (or strength), NDC, medication class (e.g., controlled, non-controlled), condition of the medication, lot number, expiration date, quantity, unit cost, extended credit amount or due date, Global Trade Item Number (GTIN), etc. When a plurality of invoices are required by the third party, the different invoices can be grouped by, for example, one or more members of the information to be added to the invoice, as provided herein. In addition, the invoice can further comprise the third party's information (e.g., returning company's information). For example, the third party can dictate or determine how they want products electronically consolidated, either by NDC, lot number, or GTIN. For a direct return to the third party, the third party's information to be provided in the invoice can include company address, AP vendor number, etc. For an indirect return to the third party, the third party's information to be provided in the invoice can include company address, wholesaler address, DEA vendor number, AP vendor number, etc. Each invoice as disclosed herein can comprise a unique prefix (e.g., as determined or instructed by the third party), followed by sequential numbers (e.g., date, day, time, etc.).

In accordance with the methods and systems disclosed herein, an invoice for the managed medications (e.g., disposed or discarded medications), can be generated once every 5 minutes, 10 minutes, 15 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 11 hours, 12 hours, 16 hours, 20 hours, 24 hours, 2 days, 3 days, 4 days, 5 days, 6 days, 7 days, 2 weeks, 3 weeks, 4 weeks, 2 months, 3 months, 4 months, 5 months, 6 months, 7 months, 8 months, 9 months, 10 months, 11 months, 12 months, or more. For example, a large pharmaceutical company or a large medication manufacturing company can require invoices to be generated and/or sent (e.g., stored in a database) on a weekly basis. In another example, a relatively smaller pharmaceutical company or medication manufacturing company can require an invoice to be generated and/or sent (e.g., stored in a database) on a quarterly basis. The invoice(s) can be reviewed (e.g., automatically by the systems disclosed herein, by the user or the third party) to maximize the return credit. The invoice(s) can be sent to the third party digitally.

For medication management as disclosed herein, a return goods policy (RGP) for the medications can have one or more requirements (e.g., determined by the manufacturer, the pharmaceutical company, via negotiations, etc.). For example, the RGP can be specific to a labeler code or NDC of the medications. Non-limiting examples of items (e.g., requirements or qualifications) in such policy can include (i) allowed returns (e.g., specific list of medications that qualify for return), (ii) vendor-owned inventory (VOI) (e.g., VOI vendor, VOI NDC), (iii) time with respect to expiration (e.g., months prior to and/or after the expiration date), (iv) whether a portion of the medication (e.g., the medication dosage or package) is accepted, (v) what is a minimum threshold for accepting a portion of the medication, (vi) whether an exact amount (e.g., count, volume, etc.) of the medication is required, (vii) whether repacked medications are accepted, (viii) whether lot number is required, (ix) whether the medication must be sealed, (x) whether prescription vial is accepted, and/or (xi) whether there is a credit discount.

Figure 18:
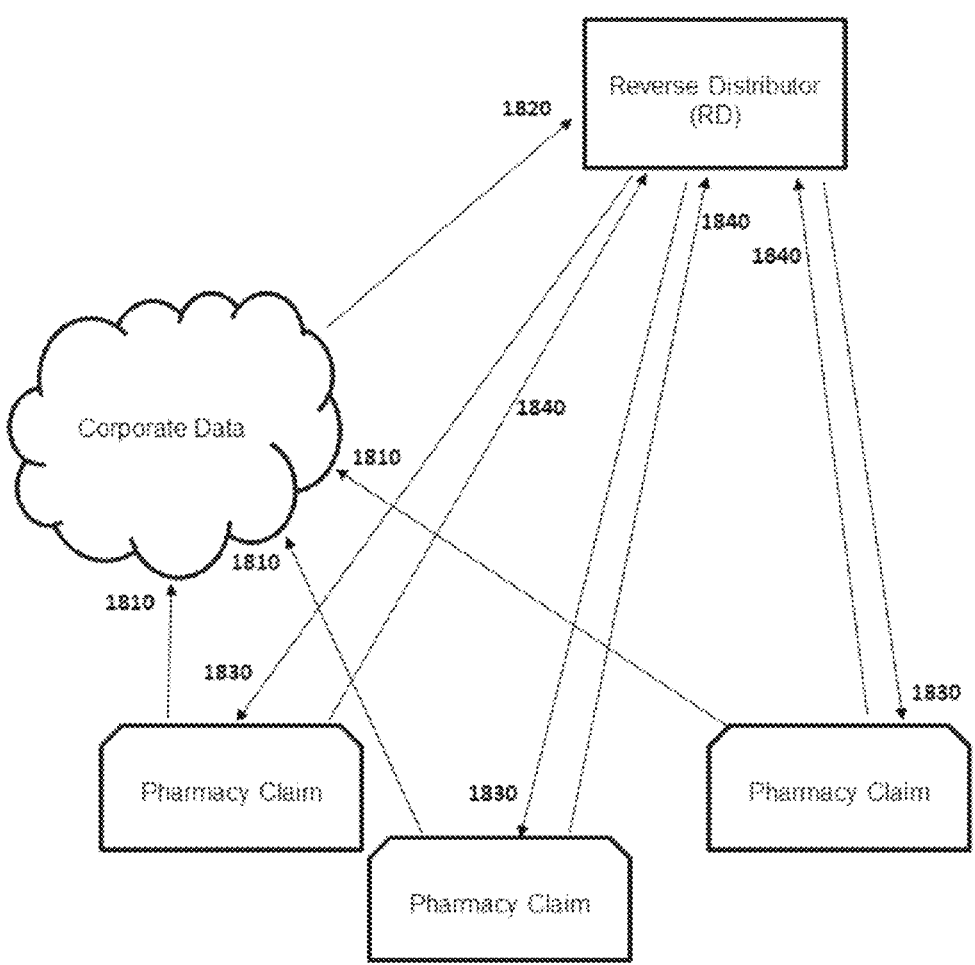
FIG. 18 illustrates an example flow chart of a process of returning a product for credit through a reverse distributor.

In some embodiments, as disclosed herein, manufacturers (e.g., medication manufacturers) can have a published return goods policy or a company specific (e.g., negotiated) return goods policy. Such policy can provide tails of the conditions that may be or must be met in order to receive credit. For example, a product (e.g., medications) can be eligible for credit when the product is returned with greater than a threshold amount (e.g., 25% by count or weight) product remaining, returned within a defined time period (e.g., 6 months prior and 12 months after the expiration date, etc.). In another example, certain manufacturers may only issue credit for sealed products (e.g., no opened products, no products with partial medication remainder, etc.). All products are inducted to determine if they are eligible for credit today or at some point in the future. If eligible for credit, the policy will provide guidance on the credit amount. These flows walk you through that entire process FIG. 18 schematically illustrates the process for returning a physical product from a pharmacy (e.g., a chain pharmacy) to a reverse distributor (RD). The process may comprise requesting such return. The process can start at a pharmacy chain. The staff at the pharmacy chain can pull the product (e.g., medication) that may needed to be returned (e.g., involving a manual process where the staff read the expiration dates on the pharmaceutical bottles to determine what needs to be returned). Subsequently, the pharmacy can create a claim on their internal system which will decrement their inventory on hand by National Drug Code (NDC). Claim details can include data such as the returning pharmacy information, the RD information, and/or the product details (e.g., NDC, drug class, drug name, drug description, drug quantity, etc.). Such pharmacy claims ("Pharmacy Claim") can be consolidated at the corporate office of the pharmacies, e.g., by sharing data electronically (flow indicated by arrows 1810). The corporate office can send the consolidated pharmacy claim data to the RD (flow indicated by arrow 1820). RD can in turn send the claim specific shipping label(s) to the returning pharmacy (flow indicated by arrows 1830). Generation and shipping of the shipping labels from RD to pharmacies can take at least one day or a plurality of days. However, this can take even longer (e.g., between 5 days and 15 days, or longer) depending on the type of products being returned. For example, in order to return a Schedule II controlled substance, the pharmacy may need to ship the product along with a specific form generated by the RD (e.g., a 222 form required by the DEA for the movement of Schedule II controlled substances). Pharmacy can then return the physical product to the RD along with the shipping label and other additional required documents (e.g., the 222 form) (flow indicated by arrows 1840), which process can take up to between about 5 days and 10 days, or longer.

Figure 19:
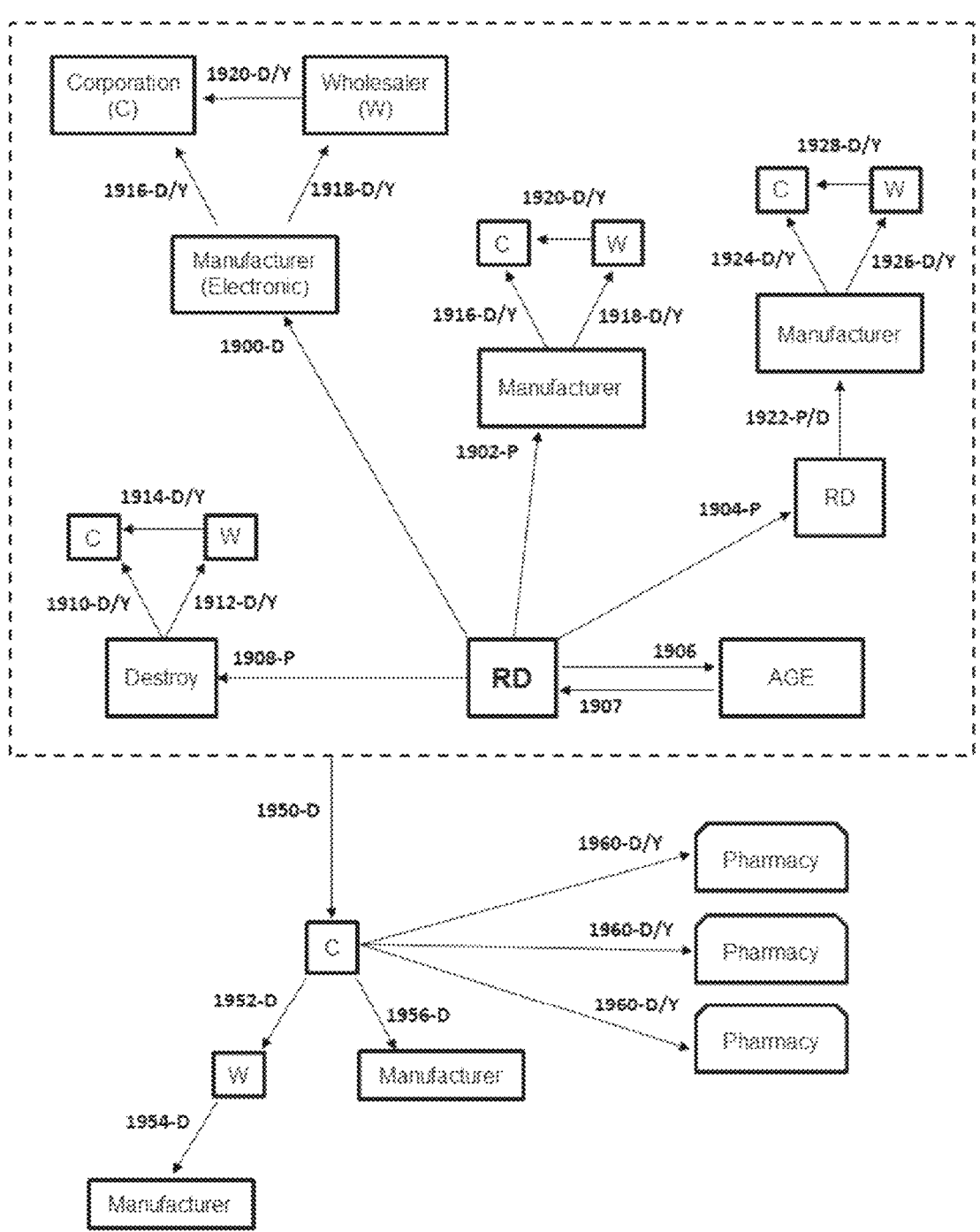
FIG. 19 illustrates another example flow chart of a process of returning a product for credit through a reverse distributor.

FIG. 19 schematically illustrates the process once the RD receives the returned products (e.g., as described in FIG. 18). The process may illustrate the flow of the products and their credits. Referring to FIG. 19, the RD can admit or "induct" the returned products that are returned from pharmacies (e.g., in the form of a box that contains multiple pharmaceutical bottles), e.g., in order of receipt of the products. This induction process can take up to about two weeks, or more. Induction can be a process of entering information from each individual returned product (e.g., medication bottle) into a system (e.g., a computerized system), which can compare, cross-examine, request verification of, or bounce such information against the manufacturer's return goods policy (as disclosed elsewhere herein), to determine disposition methods of the returned products (e.g., in accordance with the flow chart in FIG. 21). When the returned products are returnable for an immediate credit, such products can be consolidated and/or destroyed. For example, the returned products can be electronically returned (e.g., data of the returned products) to the manufacturer (arrow 1900-D, wherein "D" denotes an electronic transfer of data throughout FIG. 19) and/or physically returned to the manufacturer (arrow 1902-P, wherein "P" denotes a physical product movement throughout FIG. 19), shipped to a second RD (arrow 1904-P) (e.g., another RD responsible for a subset of medications, such as specific medication products), or set aside into "AGING" where the product(s) (e.g., medication(s)) can be held until the product(s) reach the allowable expiration date and become eligible for credit (arrow 1906), after which the product(s) can be go back to the RD induction process (arrow 1907) for other dispositions as described herein (e.g., arrows 1902-P, 1904-P, etc.). Alternatively, the product(s) can be sent out for destruction (arrow 1908-P), and credits can be issued (e.g., to pharmacies) when the RD provides proof of destruction. Credit(s) as disclosed herein can be sent electronically either directly to the corporate office of the retail pharmacies ("C") (arrow 1910-D/Y, wherein "Y" denotes a transfer of credit throughout FIG. 19), or to the wholesaler ("W") (arrow 1912-D/Y). The wholesaler can subsequently send credits to the corporate office (arrow 1914-D/Y). The products sent either physically (1902-P) or electronically (1900-D) to the manufacturer can be analyzed by the manufacturer who will issue credit electronically directly to the corporate office (arrow 1916-D/Y), or to the wholesaler (arrow 1918-D/Y) and then to the corporate office (arrow 1920-D/Y). The products sent to the second RD (1904-P) can go through the entire induction process again, e.g., wherein the products and/or data can be sent to a manufacturer (arrow 1922-P/D), with credit sent electronically to the corporate office (arrow 1924-D/Y), or to the wholesaler (arrow 1926-D/Y) then to the corporate offices (arrow 1928-D/Y). Induction information or invoice details of any one of the transactions described in FIG. 19 (e.g., any one of process indicated by arrows 1900-1928, such as arrows 1900-D, 1902-P, 1904-P, and/or 1908-P) can be transmitted electronically to the corporate office (arrow 1950-D). The Invoice information can include, for example, the invoice number, manufacturer name, invoice amount, and associated fees. The invoice information can comprise debit memos. This information can be transmitted electronically to the wholesaler (arrow 1952-D) then to the manufacturer (arrow 1954-D), or directly to the manufacturer (arrow 1956-D). The induction information as disclosed herein (e.g., sent via arrow 1950-D) can recap the returning site, what product was sent, whether the returned product is determined to be eligible for credit, how much credit is expected, etc. Such credit can be passed to the returning site, such as the pharmacies (arrow 1960-D/Y). As disclosed in FIG. 19, the transfers indicated by the arrows 1900-D, 1902-P, 1904-P, and/or 1908-P can indicate or comprise return authorization.

Referring to "AGE" in FIG. 19, manufacturers can state the conditions that must be met in order to receive credit (e.g., per the NDC level or requirement). This can include the date range, such as 6 months prior and 12 months after expiration date. For example, if the product (e.g., medication) is not within such date range, the product has to be held "aged" until it falls within that window and is therefore eligible for credit within the policy.

Referring to FIG. 19, induction by the RD can be a manual process of entering information about the returned product, e.g., entering information from the physical medication bottle returned into the processing system. Such information can include, for example, the NDC, lot number, expiration date, condition, and quantity of the medications.

Figure 20:
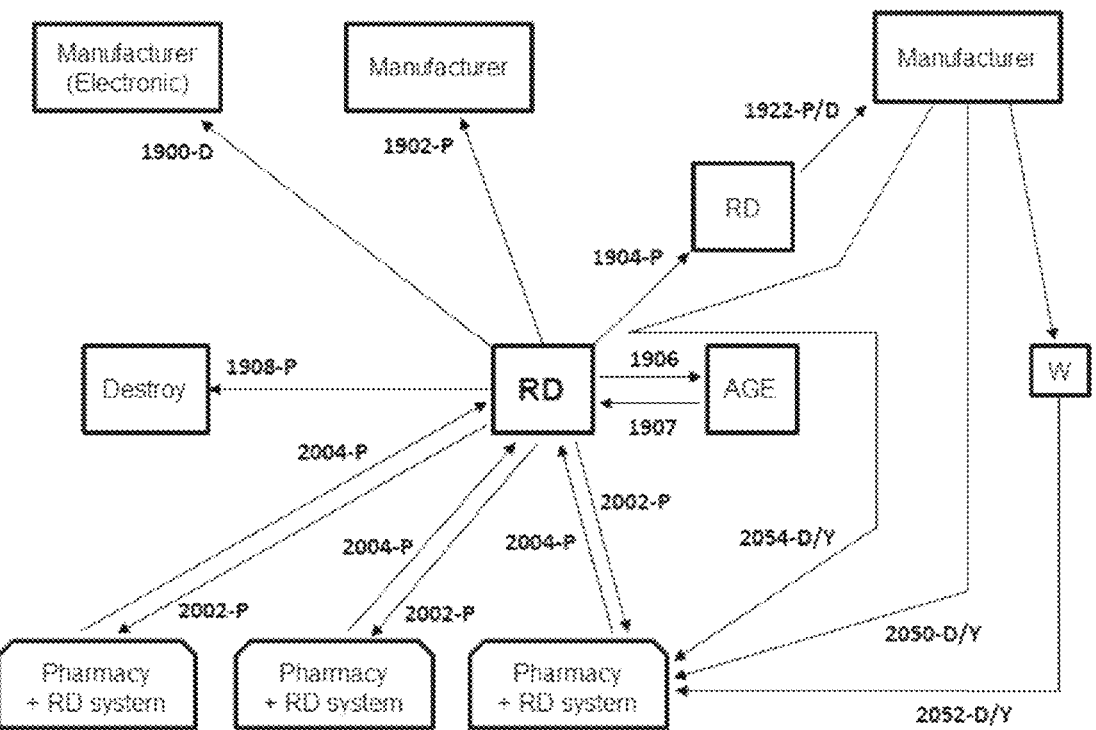
FIG. 20 illustrates a different example flow chart of a process of returning a product for credit through a reverse distributor.

FIG. 20 schematically illustrates the reverse distribution process at a smaller setting or in a smaller scale. The process may illustrate the flow of the products and their credits. This flow can start at the pharmacy which can use the RD's system (e.g., the RD's website) to initiate a return. The pharmacy staff can log into the RD's system and enter (e.g., manually), for example, the NDC, lot number, expiration date, and/or quantity of medications being wasted. Once the pharmacy staff enter all the medications bottles needing to be returned, the pharmacy staff can close the collection box of the RD's system and print out the shipping label and/or a manifest detailing what is being returned. In case the medications are Schedule II controlled substances, it may be necessary for the pharmacy to wait to receive the 222 form via mail from the RD (process 2002-P, wherein "P" denotes a physical product movement throughout FIG. 20). Once all paperwork is received (e.g., digitally and/or physically), the box can be physically shipped to the RD (process 2004-P). The returned products and information thereof can flow through the same dispositions as stated previously, e.g., as demonstrated in FIG. 18 or 19. For example, once the products and/or data can are sent to a manufacturer from the second RD (arrow 1922-P/D), the manufacturer can send credit to the pharmacy directly (arrow 2050-D/Y) or via the wholesaler (arrow 2052-D/Y). The difference here in FIG. 20, for example, can be that the credit may be collected by the RD who takes a cut of the credits (e.g., monetary credit) and sends the remaining portion to the pharmacy (arrow 2054-D/Y). Throughout FIG. 20, "D" denotes an electronic transfer of data and "Y" denotes a transfer of credit. As disclosed in FIG. 20, the transfers indicated by the arrows 1900-D, 1902-P, 1904-P, and/or 1908-P can occur at least or up to about 4 times per year.

Use of the methods and systems as disclosed herein (e.g., methods and systems for medication monitoring as above-mentioned) can (1) provide new ways to share data among parties, (2) enhance methods of such data transfer, (3) decrease the amount of time it takes for such data to be transferred, and (4) decrease the time it takes for the pharmacies to receive the credits. The methods and systems as disclosed herein can, for example, allow a user at the pharmacy to send the necessary information digitally and also receive the shipping label (and/or other forms such as the 222 form) digitally from the RD. The methods and systems as disclosed herein can void packing multiple products for return, mixing of different products being returned, mixing of product labels for the return, and decrease the overall turnaround time. The methods and systems as disclosed herein can create an audit opportunity for the RD, the manufacturers, or the corporate office of the pharmacies to, for example, watch each pharmacy waste the medications (e.g., in real-time) for accountability and/or a faster invoice return, as compared to having to wait for the RD to receive the medications and recount or reassess the returned medications to process induction and credits. In another example, the methods and systems disclosed herein can minimize the involvement of the RD in giving back the credit to the pharmacy, e.g., providing the manufacturer and/or the wholesaler an easier and faster means of giving back the credit without having to go through the RD.

Figure 22:
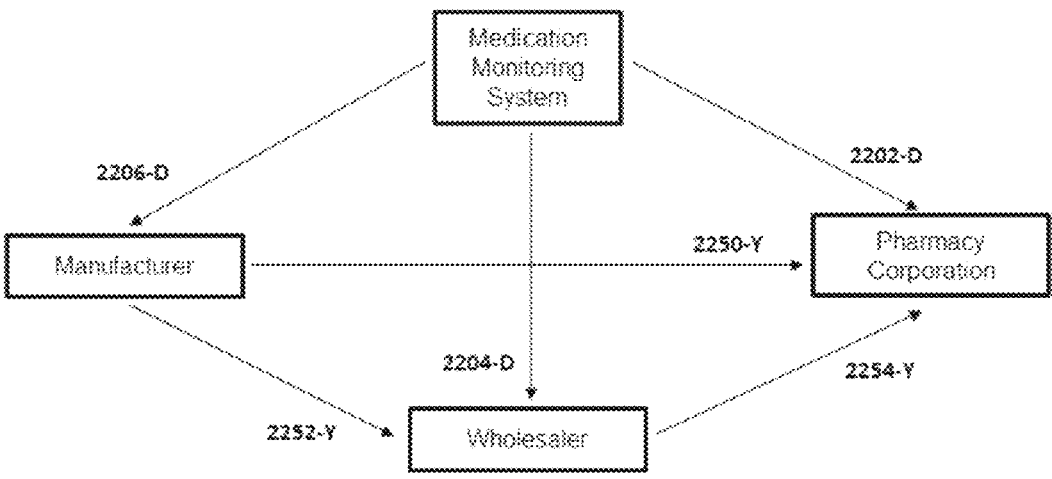
FIG. 22 illustrates an example flow chart of a process of returning a product for credit through the systems and methods of the present disclosure.

FIG. 22 schematically illustrates a financial flow of the methods and systems disclosed herein (e.g., methods and systems for medication monitoring as above mentioned) for a chain pharmacy (e.g., a retail pharmacy). In this flow, physical movement or shipment of a product (e.g., medication) may not and need not be required. Instead, electronic transfer of data (e.g., digital data related to the medications as disclosed herein) to the corporate office or "corporation" of the chain pharmacy (arrow 2202-D), to the wholesaler (arrow 2204-D), and/or the manufacturer (arrow 2206-D) may be sufficient for the pharmacy to receive credit. The manufacturer can issue the credit memo directly to the corporation (arrow 2250-Y) or to the wholesaler (arrow 2252-Y) then onto the corporation (arrow 2254-Y). If necessary, the corporation can distribute the received credits back to the retail pharmacies, e.g., via the systems of the present disclosure.

Figure 23:
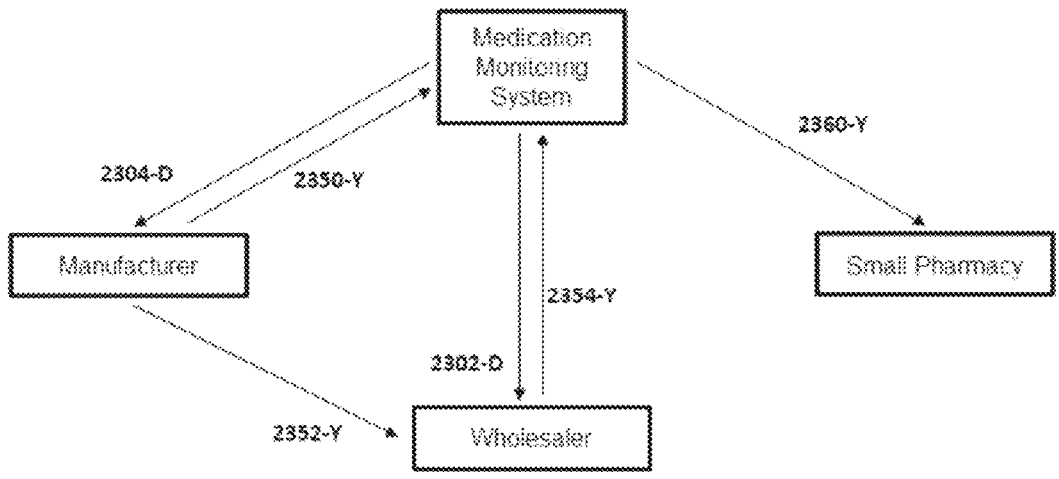
FIG. 23 illustrates another example flow chart of a process of returning a product for credit through the systems and methods of the present disclosure.

FIG. 23 schematically illustrates a financial flow of the methods and systems disclosed herein (e.g., methods and systems for medication monitoring as above mentioned) for a small pharmacy (e.g., an independent pharmacy or a hospital pharmacy). In this flow, physical movement or shipment of a product (e.g., medication) may not and need not be required. Instead, electronic transfer of data (e.g., digital data related to the medications as disclosed herein) to the wholesaler (arrow 2302-D) and/or the manufacturer (arrow 2304-D) may be sufficient for the small pharmacy to receive credit. The manufacturer can issue the credit memo directly to the medication monitoring system (arrow 2350-Y), or to the wholesaler (arrow 2352-Y) then onto the corporation (arrow 2354-Y). The medication monitoring system can take a portion of the credit and issue the rest of the credit (e.g., a percentage of the credit) to the small pharmacy (arrow 2360-Y). The medication monitoring system can take at least or up to about 1%, at least or up to about 2%, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, at least or up to about 50%, at least or up to about 60%, or more of the credit received from the manufacturer and/or the wholesaler.

Throughout FIGS. 22 and 23, "D" denotes an electronic transfer of data and "Y" denotes a transfer of credit. Throughout FIGS. 22 and 23, any data transactions indicated by "D" can utilize any formal documents, such as EDI 812 debit/credit adjustment document.

II. Other Applications

It is recognized herein that the methods and systems of the present disclosure may be used in monitoring or tracking of various other items beyond medication. Some embodiments of the methods and systems as provided herein, e.g., methods and systems for medication monitoring as abovementioned, may be usable for non-medication applications, such as, for example, monitoring or tracking unused items, expired items, excess items, recalled items, or returned items for in regulated and/or non-regulated industries. Such items can include raw materials, non-commercial or commercial products, confidential materials (e.g., documents), foods (e.g., raw ingredients, finished products, packaged foods, expired foods, etc.), etc. Some embodiments of the methods and systems disclosed herein may be used to monitor or track contraband (e.g., weapons, ammunition, illicit drugs, commercial chemicals).

The methods and systems disclosed herein can be used to verify the number of items being returned, handling of the items, shipping of the items, and storage of the items that have been returned, and the financial chargebacks incurred for returning such items.

In some embodiments, an item monitoring module (e.g., a variation of the medication monitoring module as disclosed herein) can be in digital communication with other item monitoring modules operated in other user devices and/or with other databases for data stream or exchange. Such data can represent information relevant to the disposal, return, collection, and/or retrieval of one or more items. In some cases, such data can be transmitted to a centralized database or a centralized analysis module to retrieve the items returned prior to collection of the items to a centralized location. Thus, identity and/or a quantity of the items can be verified, confirmed, or rewarded in real-time or near real-time prior to physical verification of the disposed items by a third party.

In some embodiments, the centralized database or analysis module can be operatively linked to, for example, (i) an inventory system of a retailer, (ii) a return authorization of a manufacturer, (iii) an electronic data interchange (EDI) stream for return-to-vendor (RTV), or (iv) a government system for, e.g., identifying items that need to be recalled.

FIG. 8 illustrates an example flowchart 800 of a method of monitoring item(s) handling (e.g., transport, return, storage, etc.). The method can comprise generating a digital communication between an item(s) monitoring module and at least one sensor of a user device (process 810). For example, the item(s) monitoring module can be a software (e.g., a mobile application) that can be installed on the user device (e.g., a mobile phone), and the software can be turned on to generate such digital communication. The digital communication can allow the software to control one or more components (e.g., one or more sensors, such as one or more cameras) of the user device. The method can further comprise directing, by the item(s) monitoring module, at least one sensor of the user device to record handling (e.g., drop-off) of the item(s) to an item(s) collection unit by a user (e.g., by a subject who is returning the item(s), by a subject who is storing the item(s)) (process 820). The item(s) collection unit may not be a part of the user device. The method can further comprise directing, by the item(s) monitoring module, the at least one sensor of the user device to record the user prior to, during, or subsequent to the monitored handling of the item(s) by the user (process 830). The method can further comprise generating a plurality of digital data representative of the handling and the user (process 840). The plurality of digital data can be stored for access for monitoring handling of the item(s) into the item(s) collection unit by the user. At least a portion of the plurality of digital data can be stored in a database of the user device, a centralized database operatively coupled to the user device or the item(s) monitoring module, or both.

Figure 9:
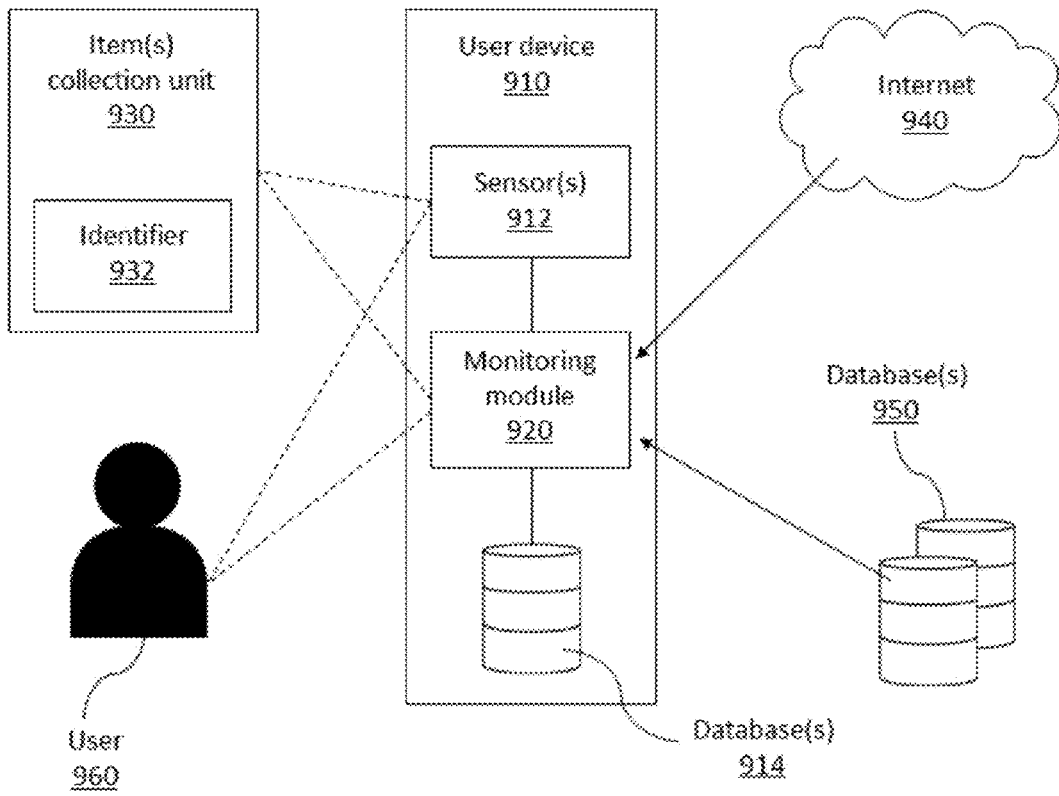
FIG. 9 schematically illustrates an exemplary ecosystem comprising an item(s) monitoring module.

FIG. 9 schematically illustrates an exemplary ecosystem comprising an item(s) monitoring module. The item(s) monitoring module can be configured to perform any of the methods disclosed herein (e.g., as described in FIG. 8). The ecosystem can comprise a user device 910, such as, for example, a mobile phone of a user 960, or that of a facility that manages the item(s). The user device 910 can comprise one or more sensors 912, such as, for example, one or more cameras. In some cases, the user device 910 can comprise (i)

a first camera 912-a disposed on a first surface of the user device 910 (e.g., a "front" facing camera) and (ii) a second camera 912-b disposed on a second and different surface of the user device 910 (e.g., a "back" facing camera), such that the first camera 912-a can capture one or more images/videos of the user 960 (e.g., the user's face) and the second camera 912-b can capture one or more images/videos of the item(s) and/or the item(s) collection unit 930 prior to, during, or subsequent to handling of the item(s) into the item(s) collection unit 930. In an example, the first camera 912-a can record a face of the user 960 while (or at the same time) the second camera 912-b can capture the user's hand, the item(s), and the item(s) collection unit 930 to record the handling of the item(s). The item(s) monitoring module 920 can be installed as a software (e.g., a mobile application) on the user device, and the item(s) monitoring module 920 can be granted access to control the sensor(s) 912 of the user device 910, the database(s) 914 of the user device 910, or both. The item(s) monitoring module 920 can direct the sensor(s) 912 to scan or capture an identifier 932 (e.g., a MRC, such as a barcode or RVC) prior to, during, or subsequent to handling of the item(s) into the item(s) collection unit 930. In some cases, the item(s) monitoring module 920 can be operatively coupled to the internet 940 to retrieve information about the user 960, the user device 910, the item(s) collection unit 930, the identifier 932 of the item(s) collection unit 930, the item(s), purchase order or return order of the item(s), original packaging of the item(s), etc. In some cases, the item(s) monitoring module 920 can be operatively coupled to one or more centralized database(s) 950, as disclosed herein, to transmit digital data to or from the database(s) 950.

In some embodiments of any one of the methods and systems disclosed herein, the term "medication monitoring module" can be used generally as a "monitoring module" to monitor management (e.g., transfer, purchase, return, disposal, wasting, storage, etc.) of objects other than medications (e.g., contraband, weapons, ammunition, illicit drugs, commercial chemicals, expired goods, unsold goods, etc.). Thus, any aspects of the methods and systems disclosed herein for a medication monitoring module may be applied to any other variants of a monitoring module, as disclosed herein. For example, various aspects of a "medication waste unit" or a "medication storage unit," as disclosed herein, can be used generally as a "waste unit" or a "storage unit" to receive and retain such objects other than medications.

III. Computer Systems

Figure 10:
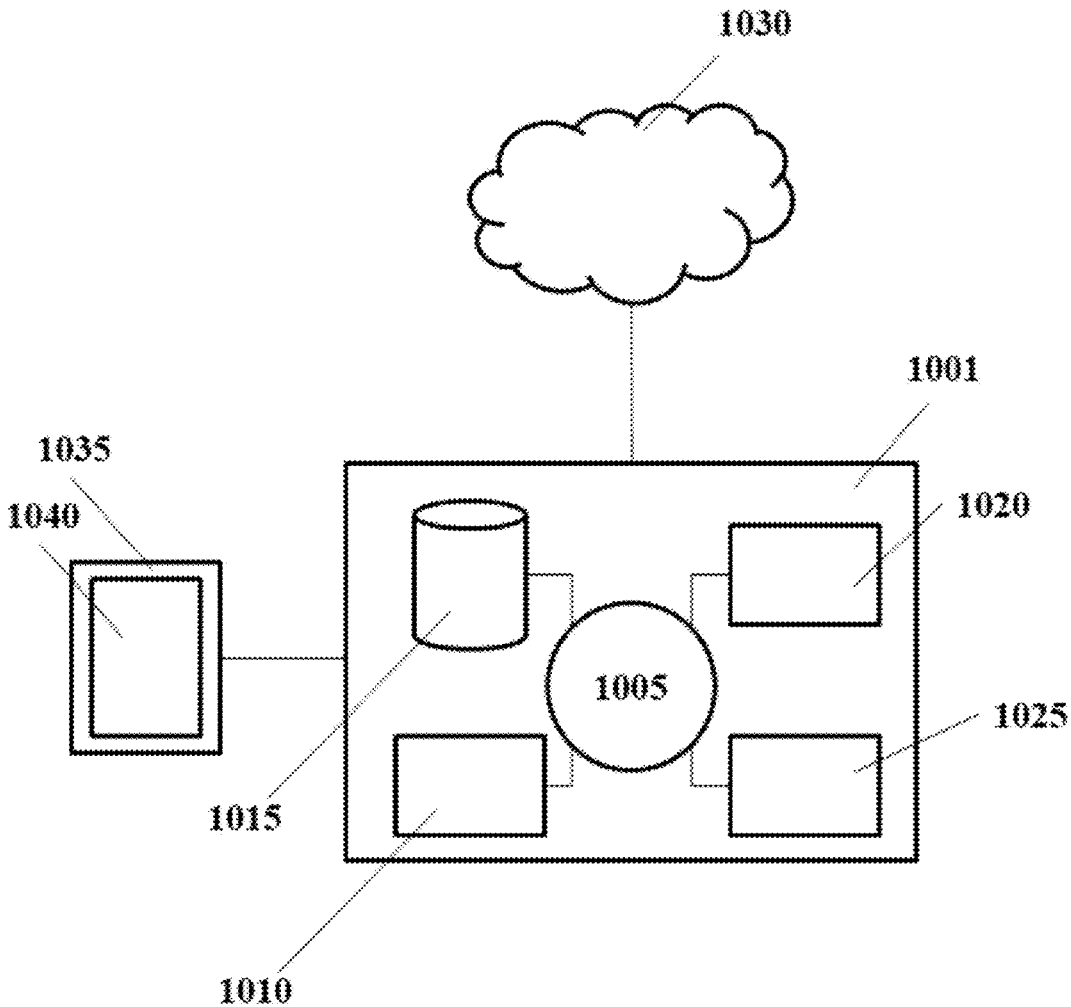
FIG. 10 shows an exemplary computer system that is programmed or otherwise configured to implement methods provided herein.

The present disclosure provides computer systems that are programmed to implement methods of the disclosure. FIG. 10 shows a computer system 1001 that is programmed or otherwise configured to tracking use of one or more items (e.g., medications). The computer system 1001 can regulate various aspects of (i) the medication monitoring module and the ecosystem thereof and/or (ii) the item(s) monitoring module and the ecosystem thereof. The computer system 1001 can be an electronic device of a user or a computer system that is remotely located with respect to the electronic device. The electronic device can be a mobile electronic device.

The computer system 1001 includes a central processing unit (CPU, also "processor" and "computer processor" herein) 1005, which can be a single core or multi core processor, or a plurality of processors for parallel processing. The computer system 1001 also includes memory or memory location 1010 (e.g., random-access memory, read-only memory, flash memory), electronic storage unit 1015 (e.g., hard disk), communication interface 1020 (e.g., network adapter) for communicating with one or more other systems, and peripheral devices 1025, such as cache, other memory, data storage and/or electronic display adapters. The memory 1010, storage unit 1015, interface 1020 and peripheral devices 1025 are in communication with the CPU 1005 through a communication bus (solid lines), such as a motherboard. The storage unit 1015 can be a data storage unit (or data repository) for storing data. The computer system 1001 can be operatively coupled to a computer network ("network") 1030 with the aid of the communication interface 1020. The network 1030 can be the Internet, an internet and/or extranet, or an intranet and/or extranet that is in communication with the Internet. The network 1030 in some cases is a telecommunication and/or data network. The network 1030 can include one or more computer servers, which can enable distributed computing, such as cloud computing. The network 1030, in some cases with the aid of the computer system 1001, can implement a peer-to-peer network, which may enable devices coupled to the computer system 1001 to behave as a client or a server.

The CPU 1005 can execute a sequence of machine-readable instructions, which can be embodied in a program or software. The instructions may be stored in a memory location, such as the memory 1010. The instructions can be directed to the CPU 1005, which can subsequently program or otherwise configure the CPU 1005 to implement methods of the present disclosure. Examples of operations performed by the CPU 1005 can include fetch, decode, execute, and writeback.

The CPU 1005 can be part of a circuit, such as an integrated circuit. One or more other components of the system 1001 can be included in the circuit. In some cases, the circuit is an application specific integrated circuit (ASIC).

The storage unit 1015 can store files, such as drivers, libraries and saved programs. The storage unit 1015 can store user data, e.g., user preferences and user programs. The computer system 1001 in some cases can include one or more additional data storage units that are external to the computer system 1001, such as located on a remote server that is in communication with the computer system 1001 through an intranet or the Internet.

The computer system 1001 can communicate with one or more remote computer systems through the network 1030. For instance, the computer system 1001 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iphone, Android-enabled device, Blackberry®), or personal digital assistants. The user can access the computer system 1001 via the network 1030.

Methods as described herein can be implemented by way of machine (e.g., computer processor) executable code stored on an electronic storage location of the computer system 1001, such as, for example, on the memory 1010 or electronic storage unit 1015. The machine executable or machine readable code can be provided in the form of software. During use, the code can be executed by the processor 1005. In some cases, the code can be retrieved from the storage unit 1015 and stored on the memory 1010 for ready access by the processor 1005. In some situations, the electronic storage unit 1015 can be precluded, and machine-executable instructions are stored on memory 1010.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1001 can include or be in communication with an electronic display 1035 that comprises a user interface (UI) 1040 for providing, for example, a UI on a display of the user device. Examples of UI's include, without limitation, a graphical user interface (GUI) and web-based user interface. In some embodiments, the electronic display may comprise a touch screen.

Methods and systems of the present disclosure can be implemented by way of one or more algorithms. An algorithm can be implemented by way of software upon execution by the central processing unit 1005. The algorithm can, for example, (i) determine a probability of item(s) mismanagement (e.g., diversion of medications) by a user (e.g., a healthcare provider) and/or (ii) determine utilization and/or compliance of particular item(s) for a user.

IV. Augmented Reality

In some embodiments of the methods or systems of the present disclosure, an augmented reality system may be used. At least one advantage of using the augmented reality system can be that it can reduce or eliminate the need for medical professionals to make physical contact with a system of the present disclosure. Reduced or eliminated contact can create a cleaner medical environment.

In some embodiments, the augmented reality system may comprise a screen for displaying augmented reality objects. In some embodiments, the screen may be integrated within a mobile device, such as a smart phone or a tablet. In some embodiments, the screen may be integrated into a headset. In some embodiments, the screen may be integrated into glasses.

In some embodiments, the augmented reality system may be used to display one or more GUIs of the present disclosure. In some embodiments, the augmented reality system may be used to register one or more user inputs. In some embodiments, the augmented reality system may be used to provide one or more verbal instructions to a user. In some embodiments, the augmented reality system may be used to receive one or more verbal instructions from a user.

In some embodiments, the augmented reality system may comprise a gesture detector. In some embodiments, the gesture detector may comprise a glove. In some embodiments, the gesture detector may be a thimble. In some embodiments, the gesture detector may be an optical sensor configured to detect a gesture from a hand. In some embodiments, the optical sensor may be a camera.

V. Block Chains

In some embodiments of the methods or systems of the present disclosure, one or more blockchains may be used to track or monitor items. In some cases, a blockchain may refer to a shared and immutable ledger for recording transactions and tracking assets. In some embodiments, a blockchain may be used to record transactions regarding medications. In some embodiments, a transaction may be between any two entities disclosed herein. In some embodiments, a transaction may comprise a trade of an item for currency. In some embodiments, a transaction may comprise destruction or waste of an item in exchange for currency. In some embodiments, the item may be a medication. In some embodiments, the item may be a contraband. In some embodiments, the item may be a good rendered unfit for sale to a consumer. In some embodiments, the currency may be cryptocurrency.

In some embodiments, a transaction record may comprise an amount of the item and the currency that was traded. In some embodiments, a transaction record may comprise an amount of the item that was destroyed. In some embodiments, a transaction record may comprise an amount of the item that was destroyed in exchange for currency. In some embodiments, a transaction record may comprise a proof of destruction of the item. In some embodiments, a transaction record may comprise a record of the type of item. In some embodiments, a transaction record may comprise identifiers of the entities involved in the transaction. In some embodiments, a transaction record may comprise a signature of one or more entities involved in the transaction. In some embodiments, a transaction record may comprise a signature of a witness involved in the transaction.

In some embodiments, a blockchain may be used to record transactions regarding various items (e.g., contraband, weapons, ammunition, illicit drugs, commercial chemicals, expired goods, unsold goods, etc.). In some embodiments, a transaction may be between any two entities disclosed herein. In some embodiments, a transaction may comprise a trade of one or more items for currency. In some embodiments, the currency may be cryptocurrency. In some embodiments, a transaction may comprise destruction or waste of an item in exchange for currency.

In some embodiments, a transaction record may comprise an amount of item and currency that was traded. In some embodiments, a transaction record may comprise an amount of item that was destroyed. In some embodiments, a transaction record may comprise an amount of item that was destroyed in exchange for currency. In some embodiments, a transaction record may comprise a proof of destruction of an item. In some embodiments, a transaction record may comprise a record of the type of item. In some embodiments, a transaction record may comprise identifiers of the entities involved in the trade. In some embodiments, a transaction record may comprise a signature of one or more entities involved in the trade.

VI. Autonomous Systems

In some embodiments of the methods or systems of the present disclosure, a coupling unit may comprise one or more robots. In some embodiments, the one or more robots may be at least partially autonomous. In some embodiments, the one or more robots are fully autonomous.

In some embodiments, the one or more robots may be capable of navigating an environment autonomously. In some embodiments, the one or more robots may be capable of summoning the coupling unit to a location in an environment. In some embodiments, a user may summon the coupling unit. In some embodiments, the user may be a medical professional (e.g., a doctor, a nurse, a pharmacist, or a patient). In some embodiments, the user may summon the coupling unit through an app. In some embodiments, the user may summon the coupling unit through a voice command. In some embodiments, the user may summon the coupling unit through augmented reality. In some embodiments, the user may summon the coupling unit through a gesture. In some embodiments, the one or more robots may be configured to move the coupling unit away from the location once a task has been completed.

In some embodiments, the one or more robots may comprise one or more wheels. In some embodiments, the one or more robots may comprise one or more legs. In some embodiments, the one or more robots may comprise a location tracker (e.g., a GPS). In some embodiments, the location tracker may be configured to communicate with a wireless device, wherein the communication may be associated with a location of the one or more robots. For example, a communication between the location tracker and a wireless device in a surgical room may indicate that the one or more robots is in the surgical room. In some embodiments, the one or more robots may be configured to remain in a zone within a boundary. In some embodiments, the one or more robots may be configured to remain in a zone outside a boundary. In some embodiments, the one or more robots may be configured to seize (e.g., lock the wheels or the legs) when it leaves the zone.

In some embodiments, the one or more robots may be capable of setting off an alarm. In some embodiments, the one or more robots may be configured to set off the alarm when an unauthorized user attempts to access the contents of the coupling units. In some embodiments, the one or more robots may be configured to set off the alarm when an unauthorized user attempts to access a computer or a process of the coupling unit or the one or more robots.

In some embodiments, the one or more robots may be configured with a fail-safe mode. In some embodiments, a fail-safe mode may be locking one or more wheels or legs of the one or more robots. In some embodiments, a fail-safe mode may be closing and locking all internal access points of the coupling units. In some embodiments, a fail-safe mode may be turning off the power of the one or more robot and/or the coupling unit. In some embodiments, a fail-safe mode may be capturing and transmitting a video and/or audio in real-time to a database.

In some embodiments, the fail-safe mode may activate when an unauthorized user attempts to access the contents of the coupling units. In some embodiments, the fail-safe mode may activate when an unauthorized user attempts to access a computer or a process of the coupling unit or the one or more robots.

In some embodiments, the one or more robots may be capable of detecting how full a container is in the coupling unit. In some embodiments, the container may be a waste container. In some embodiments, the one or more robots may be capable autonomously of discarding waste when a waste container is partially or completely full.

VII. Artificial Intelligence

In some embodiments of the methods or systems of the present disclosure, an artificial intelligence (AI) system may be used. In some embodiments, the AI may identify a type of an item. In some embodiments, the AI may identify an amount of an item.

For example, an AI may be trained on data comprising images of medicine, and labels for the type of medicine. In some embodiments, the AI may be trained to output, given an image of a pill or tablet, a logical output (e.g., True/False), a categorical output (e.g., categories of medicine), or a probability output (e.g., probability that an image corresponds to a picture of a type of medicine). In some embodiments, the AI may be trained to output a number of pills and/or tablets in an image. In some embodiments, the AI may be trained to output a volume of the medicine present in an IV bag or a syringe. In some embodiments, the AI may be trained with a supervised learning algorithm. In some embodiments, the AI may be trained with a self-supervised learning algorithm. In some embodiments, the AI may be trained with an unsupervised learning algorithm.

In some embodiments, the AI segment an image comprising a plurality of medicines. In some embodiments, the AI may segment individual unit doses in the image comprising a plurality of medicines. In some embodiments, the AI may identify a medicine in each segment of the image. In some embodiments, the AI may count the number for a given type of medicine in the image. In some embodiments, the AI may determine an amount of medicine in the image. In some embodiments, the plurality of medicines may comprise at least one of: pills, tablets, syringes, IV bags, patches, eye drops, ear drops, a container thereof, or any combination thereof.

48

EXAMPLES

Example 1: Medication Waste Monitoring

Figure 7:
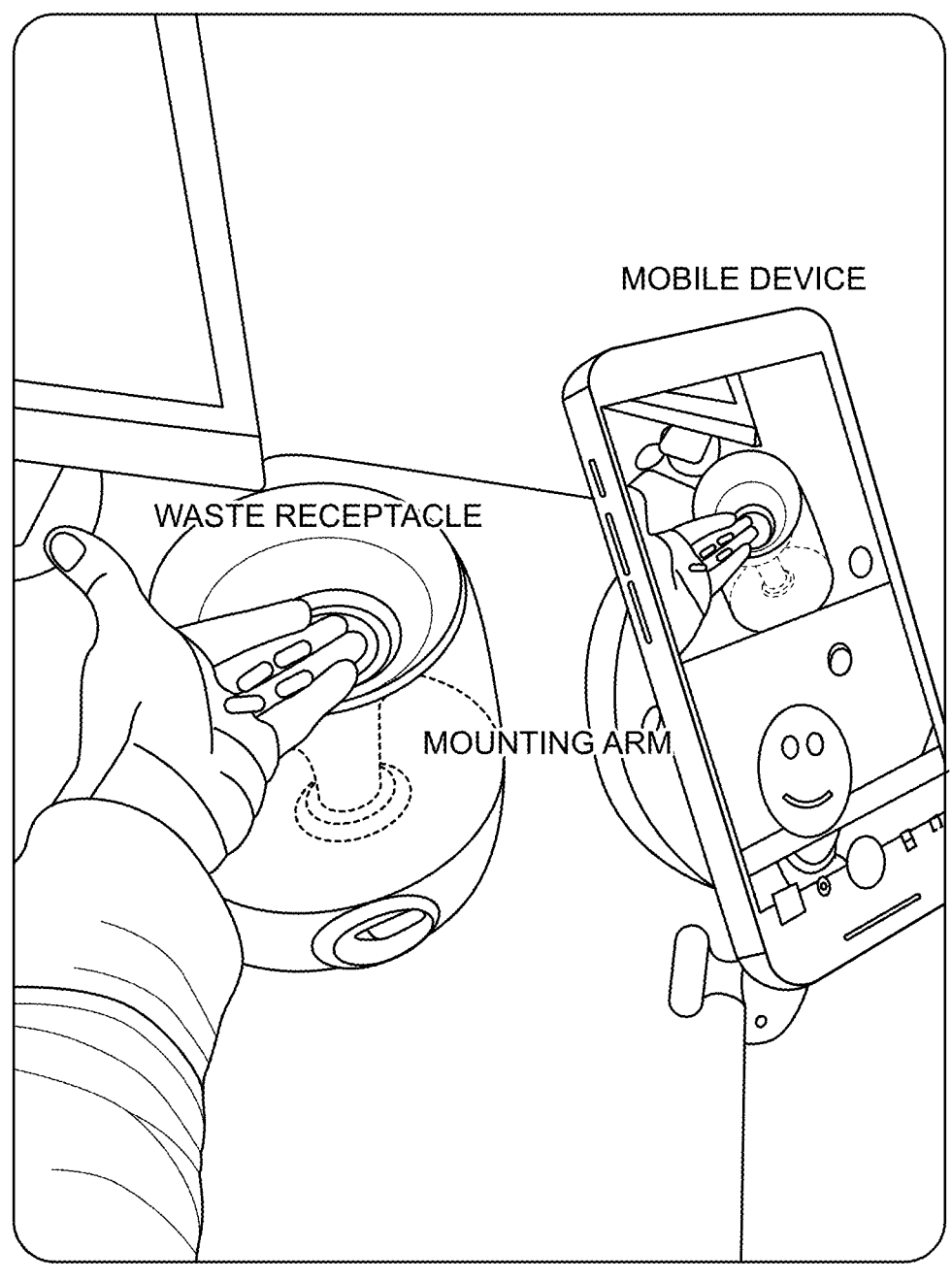
FIG. 7 schematically illustrates an exemplary application of a medication monitoring module.

The medication monitoring module and an ecosystem thereof (e.g., as illustrated in FIG. 3) can be used to capture medication wasting or dispensing events (e.g., per patient order, physical order, notification from manufacturers, etc.). As illustrated in FIG. 7, the medication monitoring module can be a mobile application that can be installed on a mobile device (e.g., a smart phone). The mobile device can comprise one or more cameras, or alternatively, the mobile device can be in digital communication (e.g., wireless communication) with a different camera that is not a part of the mobile device (e.g., a video surveillance camera). In the example shown in FIG. 7, the mobile device has a front-facing camera and back-facing camera. A medication waste unit (e.g., a waste receptacle) can be placed on top of a table. A coupling unit can be a mobile device mount or other camera/screen apparatus can be mounted to the table, and one end of the coupling unit can hold the mobile device. The coupling unit can maintain a relative distance between the medication waste unit and the mobile device substantially constant during monitoring of the medication wasting.

For medication monitoring, a user logs into the medication monitoring module via a graphical user interface (GUI) of the medication monitoring module on the mobile device. For example, the user logs into the module via providing a password or pattern, or via facial recognition. Afterwards, the medication monitoring module directs (i) the front-facing camera to view the user and (ii) the back-facing camera to view the medication and/or the medication waste unit, thereby to confirm that the user, the medication, and the medication waste unit are in frame relative to the cameras. The user then discards the medication into the medication waste unit, while the camera(s) capture one or more images/videos of the medication wasting and the user. Data comprising such images/videos is then transmitted to a database operatively coupled to the medication monitoring module and/or stored in a database of the mobile device. This procedure can be performed at a authorized facility (e.g., a medical institution, such as a hospital) or at home.

In some examples, the mobile device as disclosed herein can be any handheld or wearable device with a dual-camera recording system. The dual-camera recording system can capture: (1) medication being dispensed or wasted using, real-time video, slow motion video, and/or still image bursts; (2) positive identification of medication wasting via facial recognition of the user and the act of medication wasting; (3) other information, such as initial order, prescription details, waste details, patient information, time stamp, etc.; or (4) identifier (e.g., barcodes, RVC) of, for example, the medication waste unit.

Example 2: Medication Management

The methods and systems for medication monitoring as disclosed herein can be used for managing medications in pharmacies. In some examples, the methods and systems can be used for pharmacies to (i) communicate or interact with (e.g., directly or indirectly) a third party (e.g., pharmaceutical companies, pharmaceutical manufacturers, etc.) for discarding or returning medications that are expired, soon to be expired (e.g., within a range of expiration date), returned, or unused medications, (ii) monitor or record the discarding or returning of such medications, (iii) determine whether a particular drug should be discarded or returned in a particular way (e.g., as recommended or mandated by the third party), (iv) determine whether a particular drug is required to be discarded or returned (e.g., recalled by the pharmaceutical companies, pharmaceutical manufacturers, etc.), and/or (v) receive payback and/or incentives (e.g., from the third party as disclosed herein) for properly handling the medications.

FIG. 21 illustrates an example flowchart 2100, for a pharmacy to dispose a medication. The flowchart 2100 can present an example of a collection of rules for medication disposition for a pharmacy. For example, such flow chart can be a basis for a user of the pharmacy (e.g., a pharmacist) to follow on a GUI of a display of a device (e.g., a user device) of the system as disclosed herein.

Referring to the flowchart 2100, step (1) comprises determining (or receiving such information) whether the item in question (e.g., a medication) has been recalled, e.g., by the pharmaceutical company, the manufacturer, or the government (e.g., DEA, FDA, etc.). An image of the item can be analyzed and/or identified (e.g., by the system), then processed against a database in digital communication with the system, in order to determine whether the item has been recalled. Alternatively or in addition to, identification of the medication (e.g., medication name, National Drug Code (NDC), manufacturer's Lot number or Advanced Ship Notice (ASN), Global Trade Item Number (GTIN), etc.) can be provided by the user (e.g., typed into the GUI, scanned using a sensor of the system, etc.) to the system. In step (1), if YES, then the flow chart can proceed to step (4). Either in step (1), step (4), and/or there between, store level details can be sold to cover Drug Response Form. For example, the FDA can require the manufacturer to collect business response forms from pharmacies, but the pharmacy may not be required to fill these out. The recalling manufacturer may pay another entity (e.g., a contracted vendor) to chase down the pharmacies for information needed to fulfill such forms. In this scenario, the data collected from processing could be sold to the manufacturer. The contracted vendor may sell such data. Alternatively or in addition to, a non-contracted vendor may sell such data. In step (1), if NO, then the flow chart can proceed to step (2).

For example, the contracted vendor can be the system as disclosed herein (e.g., medication monitoring system). The manufacturer of the medications can enter into an agreement with the system as disclosed herein, e.g., to process their pharmaceuticals, collection, wasting, returns, and distributing credits thereof.

Referring to the flowchart 2100, step (2) comprises determining (or receiving such information) whether the item in question (e.g., the medication) is returnable for an incentive (e.g., a monetary credit) today based on a policy. The policy can be based on a negotiated policy between the user (e.g., the pharmacy) and a third party (e.g., the pharmaceutical company or the manufacturer). Alternatively or in addition not, the policy can be based on the third party's published returned goods policy. In step (2), if YES, then the flow chart can proceed to step (4). In step (2), if NO, then the flow chart can proceed to step (3).

Referring to the flowchart 2100, step (3) comprises determining (or receiving such information) whether the item in question (e.g., the medication) is returnable for such incentive as disclosed herein at some point in the future (e.g., at least 1 day, 2 days, 3 days, 4 days, 5 days, 6 days, 7 days, 2 weeks, 3 weeks, 4 weeks, 2 months, 3 months, 4 months, 5 months, 6 months, 7 months, 8 months, 9 months, 10 months, 11 months, 12 months, 2 years, 3 years, 4 years, 5 years, or more after). In step (3), if YES, then the flow chart can proceed to step (4). For example, the item may be stored (or "aged") and invoiced until the policy's stated time period for granting the incentive is reached. In step (3), if NO, then the flow chart can proceed to step (6).

Referring to the flowchart 2100, step (4) comprises determining (or receiving such information) whether the manufacturer of the item in question (e.g., medication manufacturer) has been contacted. In step (4), if YES, then the flow chart can proceed to step (5). In step (4), if NO, then the item may be directed to a third party (e.g., a reverse distributor, or RD), e.g., for handling the deposited medications. For example, data of the identification of the medication (e.g., Advanced Ship Notice (ASN) of the medication) can be provided to the reverse distributor, such that the reverse distributor can handle the disposed medications. Alternatively or in addition to, the disposed medications can go to a sorter (e.g., directly to a sorter) and may not require induction. For example, an unknown substance or an unknown combination of known substances may not require induction. In some cases, the sorter may sort an unknown combination of medications (e.g., a mix of pills and/or tablets) into separate piles, wherein each pile is inducted.

Referring to the flowchart 2100, step (5) comprises determining (or receiving such information) whether the item in question (e.g., the contracted medication) is (i) hazardous and/or (ii) a blister pack. For example, a medication blister pack may be a card that packages a plurality of doses of medication within small, clear, and/or light-resistant bubbles (e.g., plastic bubbles). In step (5), if YES, then the item can be invoiced in accordance with the policy (e.g., if some or all requirements of the policy are met), and the item can be directed to a hazardous waste unit. For example, the medications can be invoiced (e.g., incentive processed), and the user can direct the medications to the hazardous waste unit. In some cases, the hazardous waste unit can be returned to a reverse distributor. The user can direct the medications to the hazardous waste unit immediately, or after at least 1 minute, 5 minutes, 10 minutes, 20 minutes, 30 minutes, 1 hour, 2 hours, 3 hours, 4 hours, 6 hours, 12 hours, 18 hours, 24 hours, 2 days, 3 days, 4 days, 5 days, 6 days, 7 days, 2 weeks, 3 weeks, 4 weeks, etc., upon being notified that the disposed medications are being invoiced. Alternatively, monitoring of the user's disposal of the medications to the hazardous waste unit (e.g., by the systems and methods as disclosed herein) can be required to ensure that the user will receive the invoice. In such case, the user may need to provide (e.g., record), a proof of destruction (POD) of the medications to receive the invoice. In step (5), if NO, then the item can be invoiced in accordance with the policy, and can be destroyed on site. In some cases, the item destroyed onsite can be disposed via common garbage disposal routes (e.g., into a garbage can or a sink).

Referring to the flowchart 2100, step (6) comprises determining (or receiving such information) whether the item in question (e.g., the contracted medication) is (i) hazardous and/or (ii) a blister pack. In step (6), if YES, then the item may not be invoiced in accordance with the policy, and the item can be directed to a hazardous waste unit, as disclosed herein. In step (6), if NO, then the item may not be invoiced in accordance with the policy, and can be destroyed on site.

Example 3: Graphical User Interface (GUI) for Medication Management

The methods and systems disclosed herein can be used for a pharmacy (e.g., a pharmacist) to manage medications (e.g., disposed medications). For example, a pharmacist can utilize a user device (e.g., a cellular device, a tablet, etc.) to log into a GUI of an application that digitally connects the pharmacy to a third party (e.g., a medication manufacturer, a pharmaceutical company, etc.). The GUI can be used to record the medications that are to be disposed (e.g., wasted, returned, etc.) and receive an incentive (e.g., monetary credit) for the disposed medications that could not be sold.

Figure 21Q:
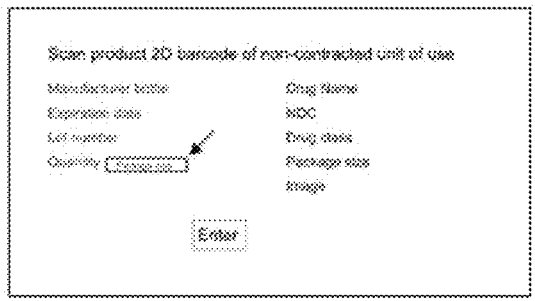
FIGS. 21A-21XX show example graphical user interfaces (GUIs) of an application in accordance with the systems and methods of the present disclosure.
Figure 21U:
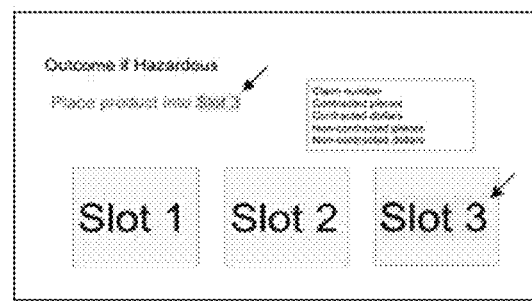
Figure 21R:
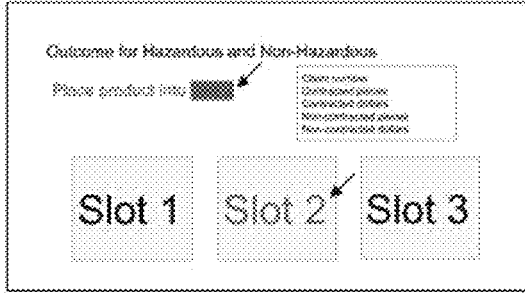
Figure 21V:
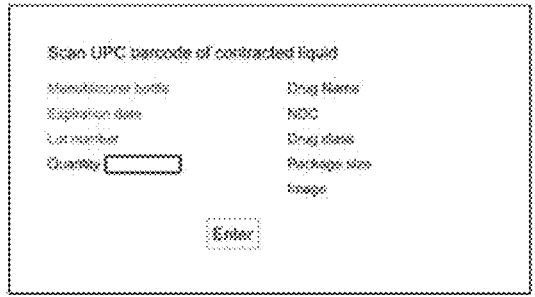
Figure 21S:
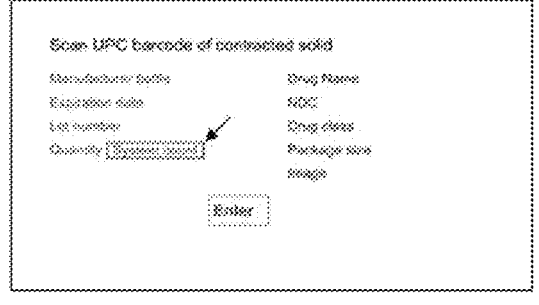
Figure 21W:
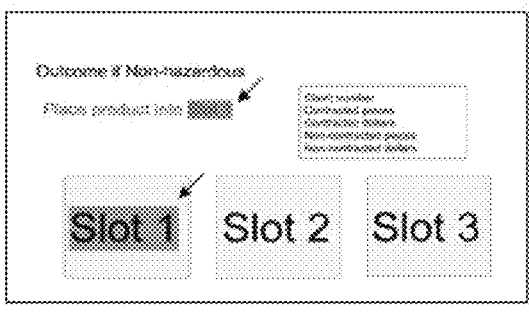
Figure 21T:
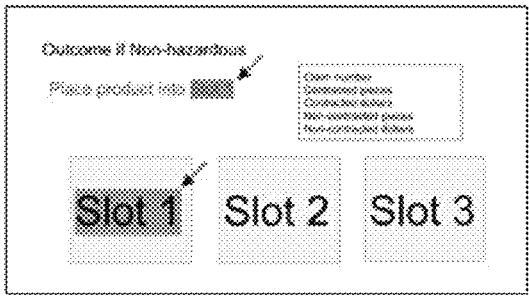
Figure 21X:
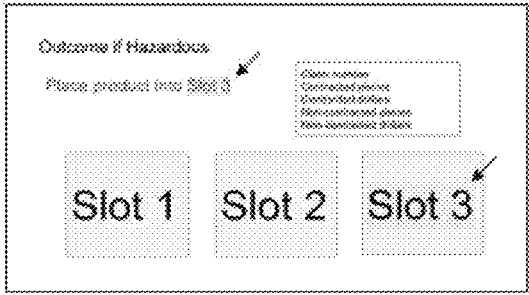

FIGS. 21A-21XX illustrate example GUIs displayed for displaying and/or receiving medication information from the user, to process disposal of the medications for credit. Referring to FIG. 21A, the user can provide (e.g., type in) a username and password to log into the application for medication management/disposal. Referring to FIG. 21B, once the user is logged in, the application can allow the user to (i) process a new claim for medication disposal or return, (ii) review claims that have already been processed, or (iii) check for credit status for previously disposed medications. For example, the user can select "Process New Claim," as indicated by the arrow.

Referring to FIG. 21C, the GUI can instruct the user to scan an identifier of the medication to be returned, e.g., by displaying a message, "Scan product 2D barcode of contracted solid (medications)." The user can have an option to manually provide the quantity of the medication or ask the system to automatically count the medications being disposed. Here, for example, the user can select "System count" as indicated by the arrow, thus not having to manually provide the medication count. Once the 2D barcode is scanned, information about the medication can be retrieved from a centralized database. For example, referring to FIG. 21D, the system can determine that the medication is hazardous, and the system can display on the GUI which slot (or receptacle) of the plurality of medication disposal slots of the system should be used for the user to dispose the medication (e.g., slot 3 as indicated by the arrow). In another example, referring to FIG. 21E, the system can determine that the medication is not hazardous, and the system can display on the GUI which slot (or receptacle) of the plurality of medication disposal slots of the system should be used for the user to dispose the medication (e.g., slot 1 as indicated by the arrow).

Figure 21G:
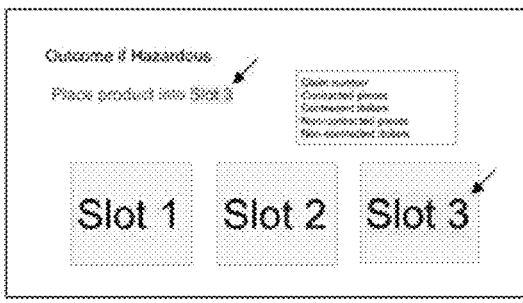
Figure 21K:
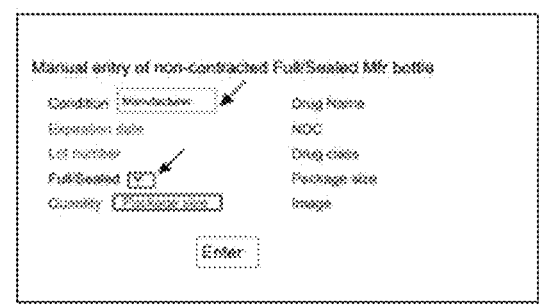
Figure 21H:
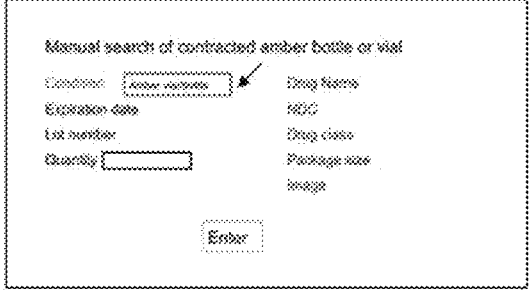

FIGS. 21F-21H illustrate GUIs for instructing the user how to discard contracted liquid medications, similar to the process as described in FIGS. 21C-21E. FIGS. 21H and 21J illustrate GUIs for instructing the user how to discard contracted unit of use (e.g., unit dosages other than solid forms or liquid forms), similar to the process as described in FIGS. 21C and 21E.

Figure 21L:
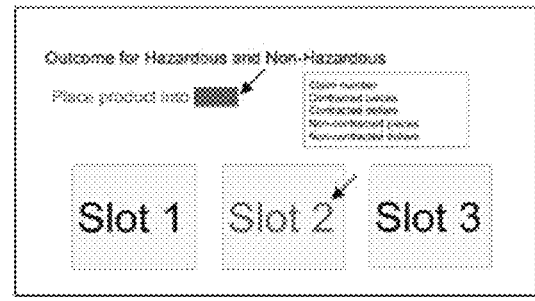
Figure 21I:
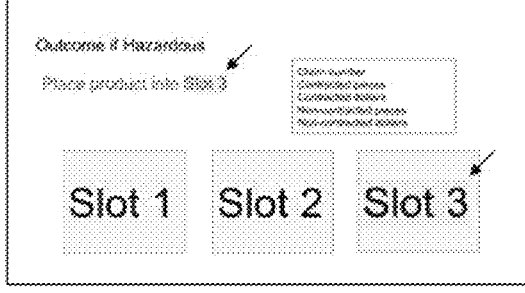

Referring to FIGS. 21K and 21L, the GUI can instruct the user to scan an identifier of the medication to be returned, e.g., by displaying a message, "Scan product 2D barcode of non-contracted Full/Sealed solid (medications)." The user can provide, via the GUI, that the medication container is full and/or sealed, as indicated by the arrow. For example, if the user selects or confirms YES (Y) to indicate that the medication is full and/or sealed (FIG. 21K, see arrow), then the system can display on the GUI which slot (or receptacle) of the plurality of medication disposal slots of the system should be used for the user to dispose the medication (e.g., slot 2 as indicated by the arrow).

Figure 21M:
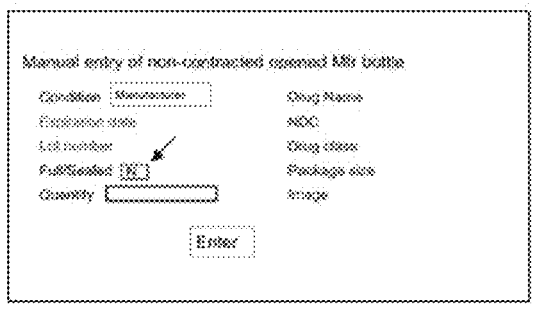
Figure 21J:
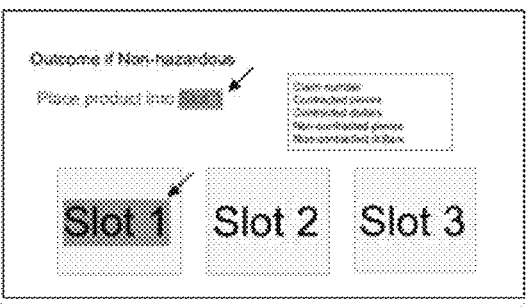
Figure 21N:
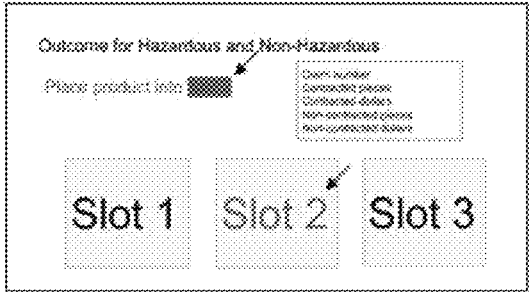

FIGS. 21M and 21N illustrate GUIs for instructing the user how to discard non-contracted opened solid, similar to the process as described in FIGS. 21K and 21L. Here, the user can select or confirm NO (N) to indicate that the medication is not full and/or sealed (FIG. 21M, see arrow).

Figure 21O:
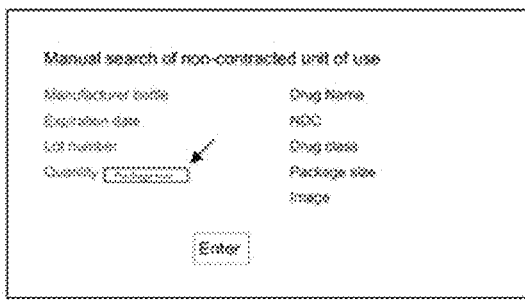
Figure 21S:
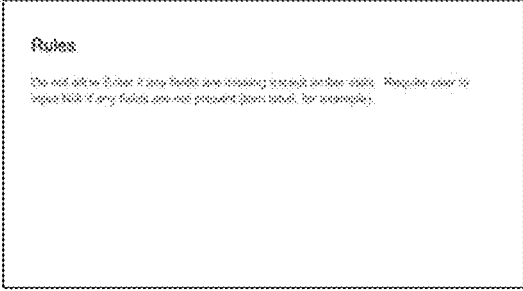
Figure 21P:
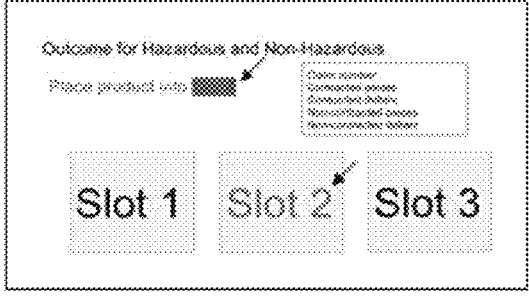
Figure 21T:
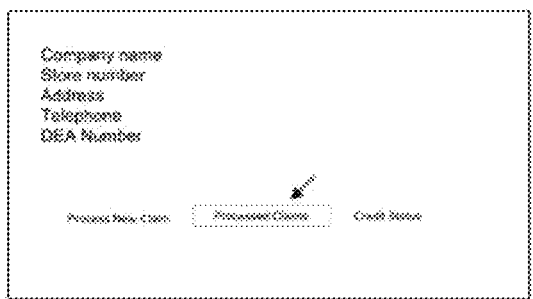
Figure 21Q:
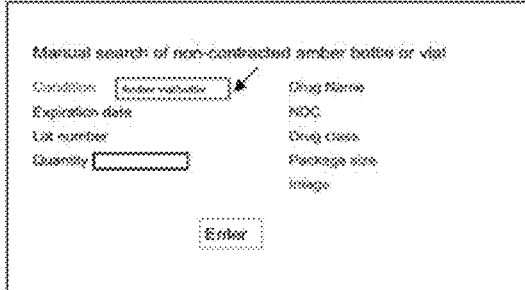
Figure 21R:
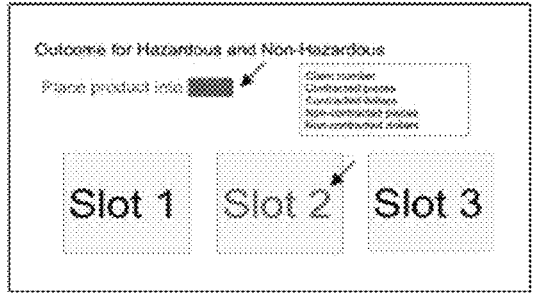

FIGS. 21O and 21P illustrate GUIs for instructing the user how to discard a contracted medication based on an expected volume of the contracted medication.

FIGS. 21Q and 21R illustrate GUIs for instructing the user how to discard non-contracted unit of use, similar to the process as described in FIGS. 21K and 21L. Here, the user can provide, select, or confirm the package size of the medication (FIG. 21Q, see arrow).

FIGS. 21S-21U illustrate GUIs for instructing the user how to discard contracted solid medications, similar to the process as described in FIGS. 21C-21E or FIGS. 21K and 21L. Here, the GUI can instruct the user to scan UPC barcode, instead of a product 2D barcode. Here, the user can select or confirm that the quantity of the medication may be determined automatically by the system, e.g., "system count" (FIG. 21S, see arrow).

FIGS. 21V-21X illustrate GUIs for instructing the user how to discard contracted liquid medications, similar to the process as described in FIGS. 21S-21U.

In some cases, the user may not have or may not know an identifier (e.g., a barcode) of the medication. In such cases, the user may be required or asked by the GUI to search for the medication from a centralized database or manually provide the medication identifier information via the GUI. Referring to FIG. 21Y, the user can provide NDC, name. and/or manufacturer of the medication to be discarded. Following, the provided information can be used by the application (e.g., automatically by the application) to obtain more information about the medication.

Referring to FIGS. 21Z-21BB, once the medication information is provided, the medication can be determined to be a contracted manufacturer bottle solid medication, and relevant information about the medication can be displaced on the GUI, including the manufacturer of the medication (FIG. 21Z, see arrow). Depending on whether the medication is non-hazardous or hazardous, then the system can display on the GUI which slot (or receptacle) of the plurality of medication disposal slots of the system should be used for the user to dispose the medication (FIGS. 21AA and 21BB, respectively).

Referring to FIGS. 21CC and 21DD, once the medication information is provided, the medication can be determined to be a contracted unit of use medication, and relevant information about the medication can be displaced on the GUI, including the package size (FIG. 21CC). Depending on whether the medication is non-hazardous or hazardous, the system can display on the GUI which slot (or receptacle) of the plurality of medication disposal slots of the system should be used for the user to dispose the medication (e.g., FIG. 21DD).

FIGS. 21EE-21GG illustrate GUIs for instructing the user how to discard contracted manufacturer liquid medications, similar to the process as described in FIGS. 21Z-21BB.

FIGS. 21HH-21JJ illustrate GUIs for instructing the user how to discard contracted amber bottle or vial medications, similar to the process as described in FIGS. 21Z-21BB. For example, the GUI can display to the user that this process is under the condition that the medication is in amber vial or bottle (FIG. 21HH, see arrow). Depending on whether the contracted amber bottle or vial medications are hazardous or non-hazardous, different slots of the plurality of medication disposal slots can be used (see FIGS. 21II and 21JJ, respectively).

Referring to FIGS. 21KK and 21LL, once the medication information is provided, the medication can be determined to be a non-contracted full/sealed manufacturer (Mfr) bottle medication, and relevant information about the medication can be displaced on the GUI, including the manufacturer information and whether the medication is full and/or sealed (FIG. 21KK, see arrows). Depending on whether the medication is non-hazardous or hazardous, the system can display on the GUI which slot (or receptacle) of the plurality of medication disposal slots of the system should be used for the user to dispose the medication (e.g., FIG. 21LL).

FIGS. 21MM and 21NN illustrate GUIs for instructing the user how to discard non-contracted, opened manufacturer (Mfr) bottle medications, similar to the process as described in FIGS. 21KK and 21LL.

Referring to FIGS. 21OO and 21PP, once the medication information is provided, the medication can be determined to be a non-contracted unit of use medication, and relevant information about the medication can be displaced on the GUI, including the quantity of the medication, such as the medication package size (FIG. 21OO, see arrow). Depending on whether the medication is non-hazardous or hazardous, the system can display on the GUI which slot (or receptacle) of the plurality of medication disposal slots of the system should be used for the user to dispose the medication (e.g., FIG. 21PP).

FIGS. 21QQ and 21RR illustrate GUIs for instructing the user how to discard amber bottle or vial medications, similar to the process as described in FIGS. 21OO and 21PP.

In some cases, the application may inform the user that there has been an error. For example, the application may not allow the user to proceed with discarding the medication to one of the plurality of medication waste receptacles. FIG. 21SS shows an example of when the application shows an error message to the user via the GUI. Referring to FIG. 21SS, the GUI can indicate that the user may not proceed with medication disposal and invoice request if one or more fields in the medication information are missing, e.g., except for amber vials. Thus, the GUI can require the user to input the missing information (e.g., actual information, or not applicable (N/A)) to proceed.

As disclosed herein, the user can use the application review claims that have already been processed (FIG. 21TT, see arrow). The GUI can subsequently display a table showing a list of one or more claim accessible to the user (FIG. 21UU). The table may have a plurality of columns for claim number, claim date, user (e.g., username or ID), contracted pieces (e.g., medications disposed for return or waste), contracted dollars (e.g., invoice amount), non-contracted pieces, and/or non-contracted dollars. The one or more claims may have been processed by the user. Alternatively or in addition to, the one or more claims shown may have been processed at the pharmacy of the user. Alternatively or in addition not, the one or more claims shown may have been processed by a plurality of pharmacies. The user may have access to view additional details of all claims shown. Alternatively, the user may have selective access to only some of the claims shown. If given access, the user can select (e.g., on the GUI) a specific claim number from the table, and the application can direct the user to another GUI screen showing additional details about the selected claim number (FIG. 21VV). Referring to FIG. 21VV, the new table can show the selected claim number, claim date, and the user responsible for the claim, as well as one or more of the following information about the medication that was wasted and/or returned: medication identifier (e.g., 2D barcode, assigned number, NDC, lot number, etc.), condition, full/sealed, expiration date, quantity, unit cost, extended credit, reason code for not being eligible for credit, contracted, ASN, EDI, whether credit is received or not, etc. If needed, the application can also display a table of the reason code for not being eligible for credit (FIG. 21WW). One or more reasons can be: (1) manufacturer does not take returns, (2) manufacturer does not take NDC, (3) manufacturer does not take partials, (4) partial minimum not met, (5) amber vial/amber bottles not accepted, (6) manufacturer seal required, (7) vendor off invoice allowance, (8) lot number not eligible for credit, (9) consignment item, and/or (10) past expiration policy and/or returned too late.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method comprising:
(a) generating a digital communication between a medication monitoring software module and at least one sensor;
(b) directing, by the medication monitoring software module, the at least one sensor to capture a plurality of images or videos of a user's disposal of a medication to a medication waste unit;
(c) storing in a database, by the medication monitoring software module, a digital data representative of the disposal of the medication by the user based at least in part on the plurality of images or videos, wherein the digital data from the database is accessible for monitoring or confirming proper wasting of the medication into the medication waste unit by the user;
(d) analyzing the digital data to one or more of (i) identify the medication disposed, or (ii) track proper disposal of the medication by the user; and
(e) transferring proof of the analyzed digital data, by the medication monitoring software module, to a third party to facilitate financial payback or incentive by the third party for the proper wasting of the medication.

2. The method of claim 1, wherein the at least one sensor comprises a plurality of sensors comprising a plurality of different optical axes, wherein the plurality of images or videos are captured from the plurality of different optical axes, and wherein:
(i) an angle between two optical axes of the plurality of different optical axes is at least 90 degrees; or
(ii) wherein the plurality of sensors comprise different cameras disposed on different surfaces, wherein the at least one sensor comprises a front-facing camera and a back-facing camera.

3. The method of claim 1, further comprising displaying, by the medication monitoring software module, the plurality of images or videos on a display.

4. The method of claim 1, further comprising directing, by the medication monitoring software module, the at least one sensor to capture an additional plurality of images or videos of the user's dispensing of the medication prior to the disposal, wherein the additional plurality of images or videos are stored for access for monitoring the dispensing by the user, wherein the at least one sensor is for tracking movement of the user.

5. The method of claim 1, further comprising:

(i) using an artificial intelligence algorithm to analyze the plurality of images or videos, to identify the user;

(ii) directing, by the medication monitoring software module, the at least one sensor or an additional sensor to scan an identifier of a packaging holding the medication prior to the user's disposal of the medication to the medication waste unit; or iii) directing, by the medication monitoring software module, the at least one sensor or an additional sensor to scan an identifier of the user.

6. A system comprising:

at least one sensor;

a database configured to store digital data; and a medication monitoring software module in digital communication with the at least one sensor and configured to:

(a) direct the at least one sensor to capture a plurality of images or videos of a user's disposal of a medication to a medication waste unit; and (b) store, in a database, a digital data representative of the disposal of the medication by the user based at least in part on the plurality of images or videos, wherein the digital data from the database is accessible for monitoring or confirming proper wasting of the medication into the medication waste unit by the user;

(c) analyze the digital data to one or more of (i) identify the medication disposed, or (ii) track proper disposal of the medication by the user; and (d) transfer proof of the analyzed digital data to a third party to facilitate financial payback or incentive by the third party for the proper wasting of the medication.

7. The system of claim 6, wherein the at least one sensor comprises a plurality of different optical axes, wherein the plurality of images or videos are captured from the plurality of different optical axes, wherein an angle between two optical axes of the plurality of different optical axes is at least 90 degrees.

8. The system of claim 6, wherein the at least one sensor comprises different cameras disposed on different surfaces, wherein the at least one sensor comprises a front-facing camera and a back-facing camera.

9. The system of claim 6, further comprising a display, wherein the medication monitoring software module is further configured to display the plurality of images or videos on the display.

10. The system of claim 6, wherein the medication monitoring software module is further configured to (i) direct the at least one sensor to capture an additional plurality of images or videos of the user's dispensing of the medication prior to the disposal, and (ii) store an additional digital data representative of the additional plurality of images or videos in the database, wherein the additional digital data from the database is accessible for monitoring the dispensing by the user and tracking movement of the user.

11. The system of claim 6, wherein (i) the medication monitoring software module comprises an artificial intelligence algorithm to analyze the plurality of images or videos to identify the user, or (ii) the medication monitoring software module is further configured to direct the at least one sensor or an additional sensor to scan an identifier of a packaging holding the medication.

12. The method of claim 1, further comprising:

(i) directing, by the medication monitoring software module, the at least one sensor or an additional sensor to measure an amount of the medication that is disposed to the medication waste unit; and (ii) comparing, by the medication monitoring software module, the measured amount and an expected amount of the medication to be disposed, thereby determining mismanagement of the medication by the user.

13. The method of claim 1, wherein the third party comprises a reverse distributor, a manufacturer of the medication, or a seller of the medication.

14. The method of claim 1, wherein the proper wasting is compliant to a means of wasting that is provided by the third party or a government agency.

15. The method of claim 1, further comprising transferring at least a portion of the financial payback or incentive to a pharmacy or a hospital.

16. The method of claim 1, wherein the plurality of images or videos captures a destruction of the medication by the user.

17. The method of claim 16, wherein the digital data is representative of the destruction of the medication.

18. The method of claim 1, wherein transferring proof of the analyzed digital data is sufficient to facilitate the financial payback or incentive by the third party.

19. The system of claim 6, wherein the third party comprises a reverse distributor, a manufacturer of the medication, or a seller of the medication.

20. The system of claim 6, wherein the proper wasting is compliant to a means of wasting that is provided by the third party or a government agency.

21. The system of claim 6, wherein the plurality of images or videos captures a destruction of the medication by the user.

22. The system of claim 21, wherein the digital data is representative of the destruction of the medication.

23. The system of claim 6, wherein transferring proof of the analyzed digital data is sufficient to facilitate the financial payback or incentive by the third party.

* * * * *